United States Patent
Ashman et al.

(10) Patent No.: US 10,808,040 B2
(45) Date of Patent: Oct. 20, 2020

(54) MODIFIED PROTEINS AND PEPTIDES

(75) Inventors: Claire Ashman, Stevenage (GB); Mary Birchler, King of Prussia, PA (US); Rudolf M. T. De Wildt, Stevenage (GB); Claire Holland, King of Prussia, PA (US); Alan Peter Lewis, Stevenage (GB); Peter Morley, Stevenage (GB); Thomas Sandal, Stevenage (GB); Michael Steward, Stevenage (GB)

(73) Assignee: Glaxo Group Limited, Brentford, Middlesex ( * ) Notice: Subject to any disclaimer, the term of this patent is extended or adjusted under 35 U.S.C. 154(b) by 254 days.

(21) Appl. No.: 14/239,196

(22) PCT Filed: Aug. 13, 2012

(86) PCT No.: PCT/EP2012/065782
§ 371 (c)(1),
(2), (4) Date: Apr. 22, 2014

(87) PCT Pub. No.: WO2013/024059
PCT Pub. Date: Feb. 21, 2013

(65) Prior Publication Data
US 2014/0227259 A1 Aug. 14, 2014

Related U.S. Application Data

(60) Provisional application No. 61/524,488, filed on Aug. 17, 2011.

(30) Foreign Application Priority Data

Dec. 12, 2011 (GB) .................................. 1121226.3
Dec. 12, 2011 (GB) .................................. 1121233.9
Dec. 12, 2011 (GB) .................................. 1121236.2
Jul. 25, 2012 (WO) ................. PCT/EP2012/064632

(51) Int. Cl.
| | |
|---|---|
| *C07K 16/00* | (2006.01) |
| *A61K 39/395* | (2006.01) |
| *C07K 16/42* | (2006.01) |
| *C07K 16/28* | (2006.01) |
| *C07K 16/22* | (2006.01) |

(52) U.S. Cl.
CPC .............. *C07K 16/42* (2013.01); *C07K 16/00* (2013.01); *C07K 16/22* (2013.01); *C07K 16/2878* (2013.01); *C07K 2317/40* (2013.01); *C07K 2317/567* (2013.01); *C07K 2317/569* (2013.01); *C07K 2317/60* (2013.01); *C07K 2317/64* (2013.01); *C07K 2319/00* (2013.01)

(58) Field of Classification Search
None
See application file for complete search history.

(56) References Cited

U.S. PATENT DOCUMENTS

2005/0271663 A1 12/2005 Ignatovich et al.

FOREIGN PATENT DOCUMENTS

| | | |
|---|---|---|
| JP | 20078925 A | 1/2007 |
| JP | 2009517069 A | 4/2009 |
| JP | 2010528645 A | 8/2010 |
| JP | 2011504740 A | 2/2011 |
| WO | WO1992/03918 A1 | 3/1992 |
| WO | WO2000/29004 A1 | 5/2000 |
| WO | 2003080672 A1 | 10/2003 |
| WO | WO 2004/003019 A2 | 1/2004 |
| WO | WO2006/003388 A2 | 1/2006 |
| WO | WO2006/030220 A1 | 3/2006 |
| WO | WO2006/129843 A2 | 12/2006 |
| WO | 2007035092 A2 | 3/2007 |
| WO | WO2007/049017 A2 | 5/2007 |
| WO | WO2007/063308 A2 | 6/2007 |
| WO | WO2007/063311 A2 | 6/2007 |
| WO | WO2007/085814 A1 | 8/2007 |
| WO | 2008020079 A1 | 2/2008 |
| WO | WO2008/076257 A2 | 6/2008 |
| WO | 2008143954 A2 | 11/2008 |
| WO | WO2008/149147 A2 | 12/2008 |
| WO | WO2008/149148 A2 | 12/2008 |
| WO | WO20081149143 A2 | 12/2008 |
| WO | WO20081149144 A2 | 12/2008 |
| WO | 2009074634 A2 | 6/2009 |
| WO | WO2009/068627 A2 | 6/2009 |
| WO | 2010017595 A1 | 2/2010 |
| WO | 2011036460 A1 | 3/2011 |

(Continued)

OTHER PUBLICATIONS

Paul, W.E. Fundamental Immunology, 3rd Edition, 1993, pp. 292-295.*

(Continued)

*Primary Examiner* — Michael D Pak
(74) *Attorney, Agent, or Firm* — Fish & Richardson P.C.

(57) ABSTRACT

The present disclosure relates to modified proteins and peptides that have reduced ability to bind to pre-existing antibodies. Such modified protein/peptide molecules can comprise C-terminal additions, extensions or tags and/or certain amino acid substitutions. Such modified molecules (e.g., fusions and conjugates) comprise proteins, peptides, antigen binding molecules, antibodies or antibody fragments such as single variable domains. The disclosure further relates to uses and formulations of compositions comprising such modified C-terminally extended and/or amino acid substituted molecules and also to methods of production and expression of these.

6 Claims, 25 Drawing Sheets
Specification includes a Sequence Listing.

(56) References Cited

FOREIGN PATENT DOCUMENTS

| WO | WO2012/042026 A1 | 4/2012 |
|----|------------------|--------|
| WO | 2012175741 A2 | 12/2012 |
| WO | WO2013/024059 A2 | 2/2013 |
| WO | 2014111550 A1 | 7/2014 |

OTHER PUBLICATIONS

MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
Wesolowski et al. (Med Microbiol Immunol,198:157-174, 2009.*
Vincke et al., Introduction to heavy chain antibodies and derived Nanobodies. Methods in Molecular Biology, vol. 911:15-26, 2012.*
Eshhar, et al., Monoclonal anti-$V_H$ antibodies recognize a common $V_H$ determinant expressed on immunoglobulin heavy chains from various species. Eur. J. Immunol., vol. 13, No. 7, Jul. 1, 1983, pp. 533-540.
Harding, et al., The immunogenicity of humanized and fully human antibodies, Residual immunogenicity resides in the CDR regions, mAbs vol. 2, No. 3, Jun. 1, 2010, pp. 256-265.
Holt, et al., Domain antibodies: proteins for therapy, Trends in Biotechnology, vol. 21, No. 11, Nov. 1, 2003, pp. 484-490.
Kupper, et al., Generation of human antibody fragments against *Streptococcus mutans* using a phage display chain shuffling approach, BMC Biotechnology, vol. 5, No. 1, Jan. 25, 2005, p. 4.
Routledge, et al., Reshaping antibodies for therapy, Jan. 1, 1996, retrieved from the internet. http://www.path.cam.ac.uk/~mrc7/reshaping/.
Skottrup, et al., Diagnostic evaluation of a nanobody with picomolar affinity toward the protease RgpB from Porphyromorms gingivalis, Analytical Biochemistry, vol. 415, No. 2, Apr. 11, 2011, pp. 158-167.

Tatusova, et al., FEMS Microbiol. 174 (1999) 247-250.
Ward, et al., Binding activities of a repertoire of single variable domains secreted from *Escherichia coli*, Nature, vol. 341, No. 6242, Oct. 12, 1989, pp. 544-546.
Davies et al., Affinity improvement of single antibody VH domains: residues in all three hypervariable regions affect antigen binding. Immunotechnology. Sep. 1996;2(3):169-79.
Holland et al., Autoantibodies to variable heavy (VH) chain Ig sequences in humans impact the safety and clinical pharmacology of a VH domain antibody antagonist of TNF-α receptor 1. J Clin Immunol. Oct. 2013;33(7):1192-203.
Jefferis, Posttranslational Modifications and the Immunogenicity of Biotherapeutics. J Immunol Res. 2016;2016:5358272.
Holt, et al., *Trends in Biotechnology*, 21(11):484-490 (2003).
Reiter, et al., *J. Mol. Biology*, 290:685-698 (1999).
Barrett, et al, Pre-clinical model of eradication of B cell leukemia with lentiviral transduced anti-CD19 chimeric immunoreceptor-modified T cells [abstract] In Proceedings of the 101st Annual Meeting of the American Association for Cancer Research, Apr. 17-21, 2010, Washington, DC Philadelphia (PA) AACR, *Cancer Res*, 70(8 Suppl):Abstract nr 2933 (2010).
Moon, et al., A PD1-CD28 "Switch Receptor" is Able to Augment Mesothelin-Directed Chimeric Antigen Receptor T Cell Therapy in a Resistant In Vivo Model of Human Tumor [abstract] In Proceedings of the 17th Annual Meeting of the American Society of Gene and Cell Therapy (ASGCT), May 21-24, 2014, Washington, DC, USA, *Molecular Therapy*, 22(Suppl 1):Abstract nr 520 (2014).
Coppieters, et al., Formatted anti-tumor necrosis factor alpha VHH proteins derived from camelids show superior potency and targeting to inflamed joints in a murine model of collagen-induced arthritis, *Arthritis & Rheumatism*, 54(6):1856-1866 (2006).
Cordy, et al., Specificity of human anti-variable heavy (VH) chain autoantibodies and impact on the design and clinical testing of a V H domain antibody antagonist of tumour necrosis factor-[alpha] receptor 1, *Clinical and Experimental Immunology*, 182(2):139-148 (2015).
Rudikoff, et al., Single amino acid substitution altering antigen-binding specificity, *Proc. Natl. Acad. Sci. USA*, 79:1979-1983 (1982).
O'Brien, S. et al. Humanization of monoclonal antibodies by CDR grafting. Methods Mol Biol. 2003;207:81-100.
Tamura et al., J Immunol., vol. 164, p. 1432-41, Feb. 2000 (Feb. 2000).

* cited by examiner

Figure 1: Frequency of pre-existing anti-drug antibodies in sera of healthy subjects
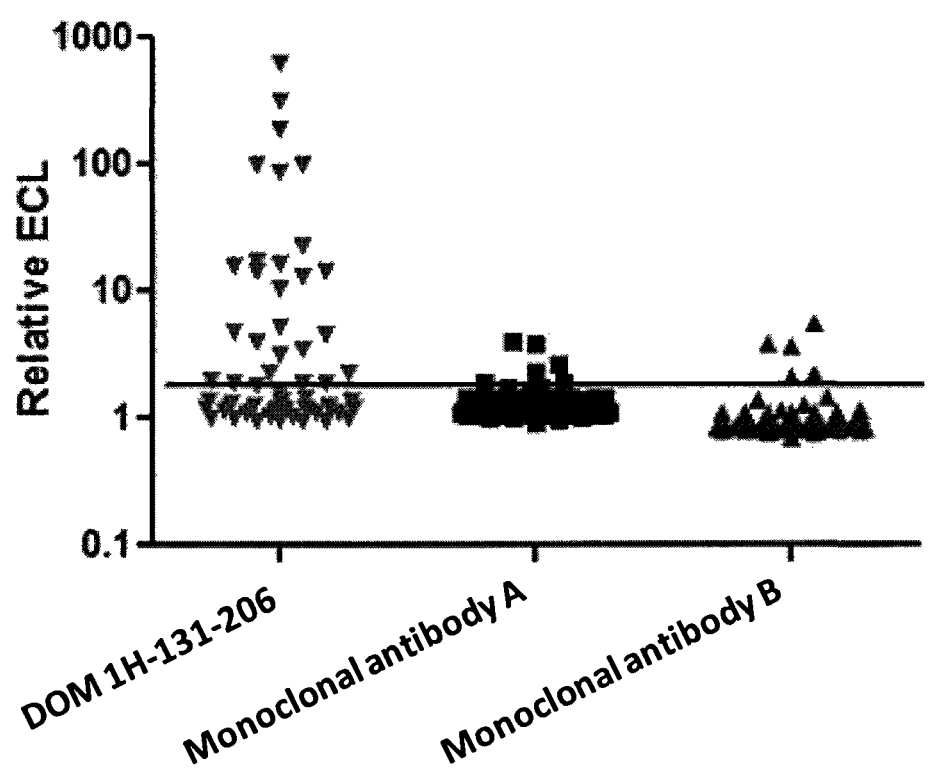

Figure 2: amino acid sequences of:

(a) Unmodified dAb DOM 1H-131-206 (anti-TNFR1)

EVQLLESGGGLVQPGGSLRLSCAASGFTFAHETMVWVRQAPGKGLEWVSHIPPDGQDPFYADSVK
GRFTISRDNSKNTLYLQMNSLRAEDTAVYHCALLPKRGPWFDYWGQGTLVTVSS (SEQ ID NO 1)

(b) Unmodified dAb DOM 1H-131-511 (anti-TNFR1)
EVQLLESGGGLVQPGGSLRLSCAASGFTFAHETMVWVRQAPGKGLEWVSHIPPVGQDPFYADSVK
GRFTISRDNSKNTLYLQMNSLRAEDTAVYYCALLPKRGPWFDYWGQGTLVTVSS (SEQ ID NO 2)

(c) Unmodified dAb DOM 1H-131-202 (anti-TNFR1)
EVQLLESGGGLVQPGGSLRLSCAASGFTFAHETMVWVRQAPGKGLEWVSHIPPDGQDPFYADSVK
GRFTISRDNSKNTLYLQMNSLRAEDTAVYYCALLPKRGPWFDYWGQGTLVTVSS (SEQ ID NO 3)

(d) Clone VHH2(d) is a bispecific format, having an IL6R binding module linked by GGGGSGGGS to a human serum albumin binding module as described in WO2010100135:
EVQLVESGGGLVQPGGSLRLSCAASGSVFKINVMAWYRQAPGKGRELVAGIISGGSTSYADSVKGR
FTISRDNAKNTLYLQMNSLRPEDTAVYYCAFITTESDYDLGRRYWGQGTLVTVSSGGGGSGGGSE
VQLVESGGGLVQPGNSLRLSCAASGFTFSSFGMSWVRQAPGKGLEWVSSISGSGSDTLYADSVKG
RFTISRDNAKTTLYLQMNSLRPEDTAVYYCTIGGSLSRSSQGTLVTVSS
(SEQ ID NO 4)

(e) Clone VHH2(e) is a bispecific format, having TNF binding module linked to a serum albumin binding module in turn linked to a TNF binding module, using GGGGSGGGS as linker as described in WO2010077422:
EVQLVESGGGLVQPGGSLRLSCAASGFTFSDYWMYWVRQAPGKGLEWVSEINTNGLITKYPDSVK
GRFTISRDNAKNTLYLQMNSLRPEDTAVYYCARSPSGFNRGQGTLVTVSSGGGGSGGGSEVQLVE
SGGGLVQPGNSLRLSCAASGFTFSSFGMSWVRQAPGKGLEWVSSISGSGSDTLYADSVKGRFTISR
DNAKTTLYLQMNSLRPEDTAVYYCTIGGSLSRSSQGTLVTVSSGGGGSGGGSEVQLVESGGGLVQ
PGGSLRLSCAASGFTFSDYWMYWVRQAPGKGLEWVSEINTNGLITKYPDSVKGRFTISRDNAKNT
LYLQMNSLRPEDTAVYYCARSPSGFNRGQGTLVTVSS
(SEQ ID NO 5)

Figure 2 continued:

(f) Clone VHH2(f) is a bivalent mono-specific format comprising two identical modules linked by an Ala-Ala-Ala linker, each module is a dAb which can bind the A1 domain of the Von-Willebrand factor, as shown in WO2009115614:

EVQLVESGGGLVQPGGSLRLSCAASGRTFSYNPMGWFRQAPGKGRELVAAISRTGGSTYYPDSVE
GRFTISRDNAKRMVYLQMNSLRAEDTAVYYCAAAGVRAEDGRVRTLPSEYTFWGQGTQVTVSSAA
AEVQLVESGGGLVQPGGSLRLSCAASGRTFSYNPMGWFRQAPGKGRELVAAISRTGGSTYYPDSV
EGRFTISRDNAKRMVYLQMNSLRAEDTAVYYCAAAGVRAEDGRVRTLPSEYTFWGQGTQVTVSS
(SEQ ID NO 6)

(g) Clone VHH2(d) is a bispecific format, having an IL6R binding module linked by GGGGSGGGS to a human serum albumin binding module as described in WO2010100135 with an alanine extension:

EVQLVESGGGLVQPGGSLRLSCAASGSVFKINVMAWYRQAPGKGRELVAGIISGGSTSYADSVKGR
FTISRDNAKNTLYLQMNSLRPEDTAVYYCAFITTESDYDLGRRYWGQGTLVTVSSGGGGSGGGSE
VQLVESGGGLVQPGNSLRLSCAASGFTFSSFGMSWVRQAPGKGLEWVSSISGSGSDTLYADSVKG
RFTISRDNAKTTLYLQMNSLRPEDTAVYYCTIGGSLSRSSQGTLVTVSSA
(SEQ ID NO 7)

(h) Clone VHH2(e) is a bispecific format, having TNF binding module linked to a serum albumin binding module in turn linked to a TNF binding module, using GGGGSGGGS as linker as described in WO2010077422 with an alanine extension:

EVQLVESGGGLVQPGGSLRLSCAASGFTFSDYWMYWVRQAPGKGLEWVSEINTNGLITKYPDSVK
GRFTISRDNAKNTLYLQMNSLRPEDTAVYYCARSPSGFNRGQGTLVTVSSGGGGSGGGSEVQLVE
SGGGLVQPGNSLRLSCAASGFTFSSFGMSWVRQAPGKGLEWVSSISGSGSDTLYADSVKGRFTISR
DNAKTTLYLQMNSLRPEDTAVYYCTIGGSLSRSSQGTLVTVSSGGGGSGGGSEVQLVESGGGLVQ
PGGSLRLSCAASGFTFSDYWMYWVRQAPGKGLEWVSEINTNGLITKYPDSVKGRFTISRDNAKNT
LYLQMNSLRPEDTAVYYCARSPSGFNRGQGTLVTVSSA
(SEQ ID NO 8)

(i) Clone VHH2(f) is a bivalent mono-specific format comprising two identical modules linked by an Ala-Ala-Ala linker, each module is a dAb which can bind the A1 domain of the Von-Willebrand factor, as shown in WO2009115614 with an alanine extension:

EVQLVESGGGLVQPGGSLRLSCAASGRTFSYNPMGWFRQAPGKGRELVAAISRTGGSTYYPDSVE
GRFTISRDNAKRMVYLQMNSLRAEDTAVYYCAAAGVRAEDGRVRTLPSEYTFWGQGTQVTVSSAA
AEVQLVESGGGLVQPGGSLRLSCAASGRTFSYNPMGWFRQAPGKGRELVAAISRTGGSTYYPDSV
EGRFTISRDNAKRMVYLQMNSLRAEDTAVYYCAAAGVRAEDGRVRTLPSEYTFWGQGTQVTVSSA
(SEQ ID NO 9)

Figure 2 continued:

(j) DOM 1H-574-208

EVQLLESGGGLVQPGGSLRLSCAASGFTFDKYSMGWVRQAPGKGLEWVSQISDTADRTYYAHAV
KGRFTISRDNSKNTLYLQMNSLRAEDTAVYYCAIYTGRWVPFEYWGQGTLVTVSS

(SEQ ID NO 10)

(k) DOM 1H-574-208-VL fusion:

EVQLLESGGGLVQPGGSLRLSCAASGFTFDKYSMGWVRQAPGKGLEWVSQISDTADRTYYAHAV
KGRFTISRDNSKNTLYLQMNSLRAEDTAVYYCAIYTGRWVPFEYWGQGTLVTVSSASTDIQMTQS
PSSLSASVGDRVTITCRASRPIGTTLSWYQQKPGKAPKLLILWNSRLQSGVPSRFSGSGSGTDFTLT
ISSLQPEDFATYYCAQAGTHPTTFGQGTKVEIKR

(SEQ ID NO 11)

(l) DT04-H-033 (parental IL-13 dAb):

EVQLLESGGGLVQPGGSLRLSCAASGFTFADYGMAWVRQAPGKGLEWVSTISYNGLYTYYADSVK
GRTISRDNSKNTLYLQMNSLRAEDTAVYYCAKYEYSPESDFDYWGQGTLVTVSS
(SEQ ID NO 12)

(m) DOM10H-53-567

GVQLLESGGGLVQPGGSLRLSCAASGFVFAWYDMGWVRQAPGKGLEWVSSIDWHGEVTYYADS
VKGRFTISRDNSKNTLYLQMNSLRAEDTAVYYCATAEDEPGYDYWGQGTLVTVSS

(SEQ ID NO 13)

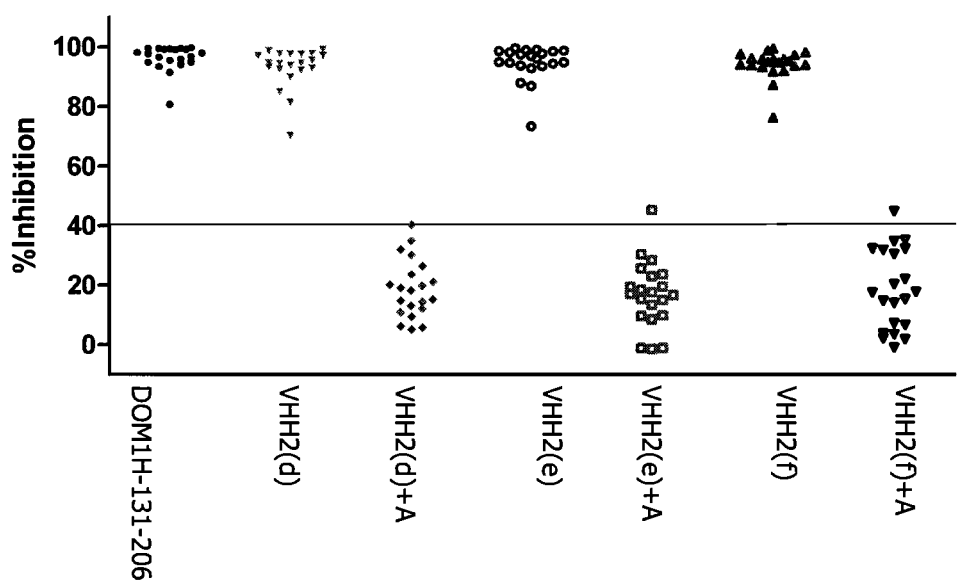
Figure 4: Impact of single alanine extensions on VHH clones

Figure 5: Incidence of binding to ADAs: Dom131-206 below refers to the Dom1h-131-206 dAb
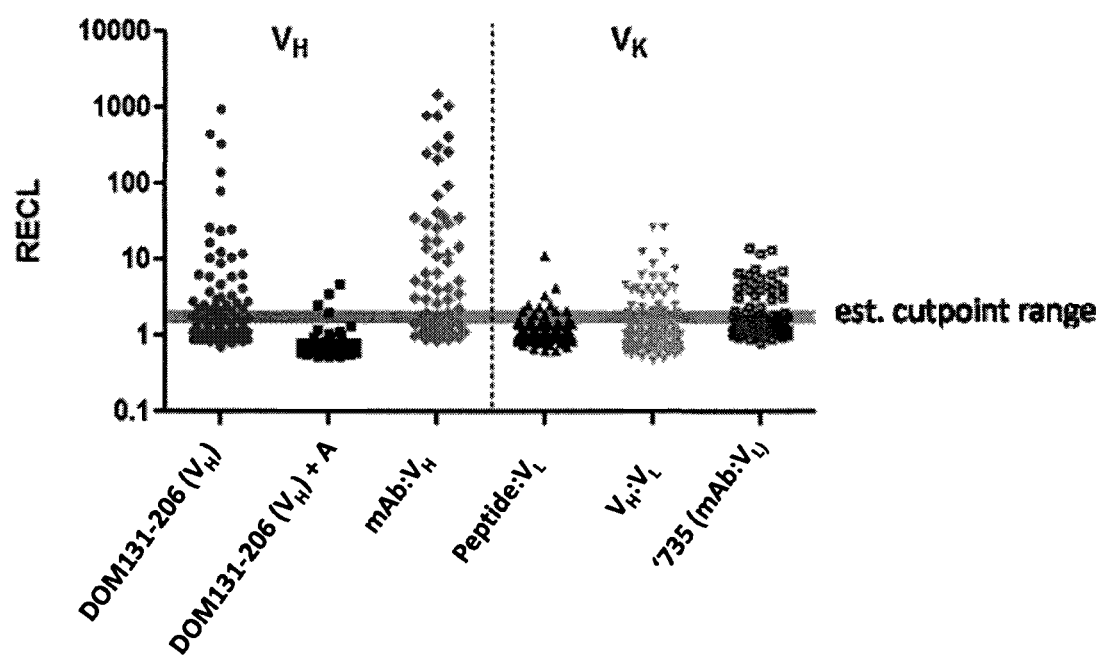

Figure 6a and 6b: The light and heavy chain variable sequences of anti-VH mAb M2.3G10.1G06 (CDR regions are underlined):

(a) Light Chain

DIVMTQSQKFMSPTVGDRVSITC<u>KASQNVGTAVA</u>WYQQKPGQSPKLLIY<u>SASNRYT</u>GVPDRFTGSGSGTDF
TLTINNMQSEDLADYFC<u>QQYGSYPLT</u>FGGGTKLEIK

(SEQ ID NO 14)

(b) Heavy Chain

EVQLQQSGPVLVKPGASVKMSCKASGYTLT<u>ESYMH</u>WVKQSHGKSLEWIG<u>VISPYNGGTSYNQKFKD</u>KATLT
VDKSSSTAYMELNSLTSEDSAVYYCTR<u>RGIYYDPSWFAY</u>WGQGTLVTVSA

(SEQ ID NO 15)

Figure 7: Competition between pre-existing anti-VH ADA and mAb M2.3G10.1G06
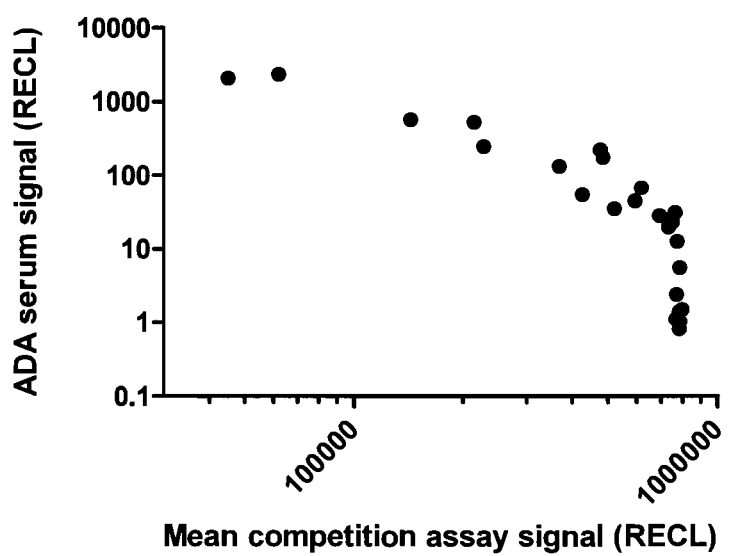

Figure 8: shows the amino acid sequences of modified anti-TNFR1 dAbs:

(a) DOM1h-131-206 dAb with an extension of a single alanine:

EVQLLESGGGLVQPGGSLRLSCAASGFTFAHETMVWVRQAPGKGLEWVSHIPPDGQDPFYADSVKGRFTIS
RDNSKNTLYLQMNSLRAEDTAVYHCALLPKRGPWFDYWGQGTLVTVSSA
(SEQ ID NO 16)

(b) DOM1h-131-206 dAb with an extension of a single alanine and a P14A framework mutation EVQLLESGGGLVQAGGSLRLSCAASGFTFAHETMVWVRQAPGKGLEWVSHIPPDGQDPFYADSVKGRFTIS
RDNSKNTLYLQMNSLRAEDTAVYHCALLPKRGPWFDYWGQGTLVTVSSA
(SEQ ID NO 17)

(c) DOM1h-131-206 dAb with a P14A framework mutation

EVQLLESGGGLVQAGGSLRLSCAASGFTFAHETMVWVRQAPGKGLEWVSHIPPDGQDPFYADSVKGRFTIS
RDNSKNTLYLQMNSLRAEDTAVYHCALLPKRGPWFDYWGQGTLVTVSS
(SEQ ID NO 18)

(d) DOM1h-131-206 dAb with an ASTKG C terminus extension

EVQLLESGGGLVQPGGSLRLSCAASGFTFAHETMVWVRQAPGKGLEWVSHIPPDGQDPFYADSVKGRFTIS
RDNSKNTLYLQMNSLRAEDTAVYHCALLPKRGPWFDYWGQGTLVTVSSASTKG
(SEQ ID NO 19)

(e) DOM1h-131-206 dAb with an ASTKG C terminus extension and a P14A framework mutation EVQLLESGGGLVQAGGSLRLSCAASGFTFAHETMVWVRQAPGKGLEWVSHIPPDGQDPFYADSVKGRFTIS
RDNSKNTLYLQMNSLRAEDTAVYHCALLPKRGPWFDYWGQGTLVTVSSASTKG
(SEQ ID NO 20)

Figure 9: shows the nucleic acid sequences of TNFR1 dAbs (a) DOM1h-131-206 dAb

GAAGTACAACTGCTGGAGAGCGGTGGCGGCCTGGTTCAACCGGGTGGTTCCCTGCGCCTGTCCTGTGCG
GCATCTGGTTTCACCTTCGCACACGAAACGATGGTGTGGGTTCGCCAAGCTCCGGGCAAAGGCCTGGAA
TGGGTAAGCCACATTCCTCCAGATGGCCAGGACCCATTCTATGCGGATTCCGTTAAGGGTCGCTTTACCA
TTTCTCGTGATAACTCCAAAAACACCCTGTACCTGCAGATGAACTCCCTGCGCGCCGAGGATACTGCGGT
GTACCATTGTGCGCTGCTGCCTAAACGTGGCCCGTGGTTCGATTACTGGGGTCAGGGTACTCTGGTCAC
CGTAAGCAGC
    (SEQ ID NO 21)

(b) Dom1h-131-206 with an extension of a single alanine
GAAGTACAACTGCTGGAGAGCGGTGGCGGCCTGGTTCAACCGGGTGGTTCCCTGCGCCTGTCCTGTGCG
GCATCTGGTTTCACCTTCGCACACGAAACGATGGTGTGGGTTCGCCAAGCTCCGGGCAAAGGCCTGGAA
TGGGTAAGCCACATTCCTCCAGATGGCCAGGACCCATTCTATGCGGATTCCGTTAAGGGTCGCTTTACCA
TTTCTCGTGATAACTCCAAAAACACCCTGTACCTGCAGATGAACTCCCTGCGCGCCGAGGATACTGCGGT
GTACCATTGTGCGCTGCTGCCTAAACGTGGCCCGTGGTTCGATTACTGGGGTCAGGGTACTCTGGTCAC
CGTAAGCAGCGCG
    (SEQ ID NO 22)

(c) Dom1h-131-206 with an ASTKG C terminus extension
GAAGTACAACTGCTGGAGAGCGGTGGCGGCCTGGTTCAACCGGGTGGTTCCCTGCGCCTGTCCTGTGCG
GCATCTGGTTTCACCTTCGCACACGAAACGATGGTGTGGGTTCGCCAAGCTCCGGGCAAAGGCCTGGAA
TGGGTAAGCCACATTCCTCCAGATGGCCAGGACCCATTCTATGCGGATTCCGTTAAGGGTCGCTTTACCA
TTTCTCGTGATAACTCCAAAAACACCCTGTACCTGCAGATGAACTCCCTGCGCGCCGAGGATACTGCGGT
GTACCATTGTGCGCTGCTGCCTAAACGTGGCCCGTGGTTCGATTACTGGGGTCAGGGTACTCTGGTCAC
CGTAAGCAGCGCGTCTACCAAAGGT
    (SEQ ID NO 23)

Figure 10: shows the nucleic acid sequences of VHH molecules:

(a) anti-IL6 VHH

GAAGTGCAGCTGGTTGAATCTGGCGGTGGTCTGGTTCAGCCGGGTGGTTCTCTGCGTCTGTCTTGCGCA
GCGTCTGGTAGCGTTTTCAAAATCAACGTGATGGCGTGGTATCGTCAGGCTCCGGGTAAAGGTCGTGAA
CTGGTTGCGGGTATCATTTCTGGCGGTAGCACTTCCTACGCGGACTCCGTTAAAGGTCGTTTCACCATCA
GCCGCGACAACGCGAAAAACACCCTGTACCTGCAGATGAACTCTCTGCGTCCGGAAGATACCGCGGTTTA
CTATTGCGCGTTCATCACCACCGAATCTGACTACGACCTGGGTCGTCGTTATTGGGGTCAGGGTACTCTG
GTAACCGTATCCTCTGGTGGTGGTGGTTCTGGTGGTGGTTCCGAAGTACAGCTGGTGGAATCTGGCGGT
GGTCTGGTACAGCCGGGTAACTCTCTGCGTCTGTCTTGTGCGGCTTCTGGTTTCACCTTCTCCAGCTTCG
GTATGTCTTGGGTTCGTCAGGCACCGGGTAAAGGTCTGGAATGGGTGTCTAGCATCTCTGGCAGCGGTT
CTGATACCCTGTACGCTGACTCCGTGAAAGGTCGTTTCACTATCTCCCGCGACAACGCGAAAACCACCCT
GTACCTGCAGATGAACTCTCTGCGTCCGGAAGACACCGCTGTTTACTACTGCACCATCGGTGGTAGCCTG
TCCCGTTCTTCTCAGGGTACCCTGGTTACTGTGAGCTCT
        (SEQ ID NO 24)

(b) anti-TNF alpha VHH
GAAGTGCAGCTGGTAGAATCTGGCGGTGGTCTGGTACAGCCGGGTGGTTCTCTGCGTCTGTCTTGCGCA
GCTTCTGGCTTCACCTTCTCCGACTACTGGATGTATTGGGTTCGTCAGGCGCCGGGTAAAGGTCTGGAA
TGGGTGTCTGAAATCAACACCAACGGCCTGATCACCAAATACCCGGACTCCGTGAAAGGTCGTTTCACCA
TCTCCCGCGACAACGCGAAAAACACCCTGTACCTGCAGATGAACTCTCTGCGTCCGGAAGATACCGCGGT
TTACTATTGTGCGCGTTCTCCGTCTGGTTTCAACCGTGGTCAGGGTACTCTGGTTACCGTAAGCTCTGGT
GGTGGTGGATCCGGCGGTGGTTCTGAAGTTCAGCTGGTTGAAAGCGGTGGTGGTCTGGTACAGCCGGG
TAACTCTCTGCGTCTGTCTTGTGCGGCTTCTGGCTTCACCTTCTCCTCTTTCGGTATGTCTTGGGTTCGT
CAGGCACCGGGTAAAGGCCTGGAATGGGTTTCCTCTATCTCTGGTAGCGGTTCTGACACCCTGTACGCT
GACTCTGTTAAAGGCCGCTTCACCATCTCCCGTGACAACGCGAAAACCACCCTGTATCTGCAGATGAACT
CCCTGCGTCCGGAAGATACCGCTGTATACTACTGCACCATCGGTGGCTCTCTGTCTCGTTCTTCTCAGGG
TACCCTGGTTACCGTATCTAGCGGTGGTGGTGGATCCGGTGGCGGTAGCGAAGTTCAGCTGGTTGAATC
TGGCGGTGGTCTGGTTCAGCCGGGTGGTTCTCTGCGTCTGTCTTGTGCAGCGTCTGGCTTCACCTTCAG
CGATTACTGGATGTACTGGGTTCGTCAGGCACCGGGTAAAGGTCTGGAATGGGTGTCTGAAATCAACAC
CAACGGTCTGATCACCAAATACCCGGACAGCGTGAAAGGTCGTTTCACCATCAGCCGTGACAACGCGAAA
AACACCCTGTACCTGCAGATGAACTCTCTGCGTCCGGAAGACACTGCGGTTTATTACTGCGCACGTTCTC
CGTCTGGTTTCAACCGTGGTCAGGGTACCCTGGTTACTGTATCCTCT
        (SEQ ID NO 25)

(c) anti-Von Willebrand VHH

GAGGTACAGCTGGTGGAAAGCGGTGGTGGTCTGGTTCAGCCGGGTGGTTCTCTGCGTCTGTCTTGCGC

AGCTTCTGGCCGTACCTTCAGCTACAACCCGATGGGTTGGTTCCGTCAGGCTCCGGGTAAAGGTCGTGA

ACTGGTTGCGGCGATCTCTCGTACCGGTGGCTCTACCTACTATCCGGACTCCGTGGAAGGTCGTTTCAC

CATCTCCCGCGACAACGCGAAACGTATGGTATACCTGCAGATGAACAGCCTGCGCGCTGAAGACACCGC

GGTTTACTATTGTGCTGCAGCGGGTGTTCGTGCTGAAGACGGTCGTGTTCGTACCCTGCCGTCCGAATA

CACCTTCTGGGGTCAGGGTACCCAGGTTACCGTTTCTTCTGCAGCGGCGGAAGTGCAGCTGGTTGAATC

TGGCGGTGGTCTGGTACAGCCGGGTGGTTCTCTGCGTCTGTCTTGTGCTGCGTCTGGTCGCACCTTCTC

CTACAACCCGATGGGTTGGTTCCGTCAGGCACCGGGTAAAGGTCGTGAACTGGTAGCGGCAATCTCTCG

CACTGGTGGCTCTACCTACTACCCGGACTCTGTTAAGGCCGCTTCACCATCTCTCGTGACAACGCGAAA

CGTATGGTGTACCTGCAGATGAACTCCCTGCGTGCGGAAGACACCGCAGTTTATTACTGCGCGGCAGCT

GGTGTTCGTGCAGAAGACGGTCGTGTTCGTACCCTGCCGAGCGAATACACCTTCTGGGGTCAGGGTACC

CAGGTAACCGTATCTTCT

(SEQ ID NO 26)

Figure 10 continued:

(d) anti-IL6 VHH with an extension of a single alanine

GAAGTGCAGCTGGTTGAATCTGGCGGTGGTCTGGTTCAGCCGGGTGGTTCTCTGCGTCTGTCT
TGCGCAGCGTCTGGTAGCGTTTTCAAAATCAACGTGATGGCGTGGTATCGTCAGGCTCCGGGTAAAGGT
CGTGAACTGGTTGCGGGTATCATTTCTGGCGGTAGCACTTCCTACGCGGACTCCGTTAAAGGTCGTTTC
ACCATCAGCCGCGACAACGCGAAAAACACCCTGTACCTGCAGATGAACTCTCTGCGTCCGGAAGATACCG
CGGTTTACTATTGCGCGTTCATCACCACCGAATCTGACTACGACCTGGGTCGTCGTTATTGGGGTCAGG
GTACTCTGGTAACCGTATCCTCTGGTGGTGGTGGTTCTGGTGGTGGTTCCGAAGTACAGCTGGTGGAAT
CTGGCGGTGGTCTGGTACAGCCGGGTAACTCTCTGCGTCTGTCTTGTGCGGCTTCTGGTTTCACCTTCT
CCAGCTTCGGTATGTCTTGGGTTCGTCAGGCACCGGGTAAAGGTCTGGAATGGGTGTCTAGCATCTCTG
GCAGCGGTTCTGATACCCTGTACGCTGACTCCGTGAAAGGTCGTTTCACTATCTCCCGCGACAACGCGAA
AACCACCCTGTACCTGCAGATGAACTCTCTGCGTCCGGAAGACACCGCTGTTTACTACTGCACCATCGGT
GGTAGCCTGTCCCGTTCTTCTCAGGGTACCCTGGTTACTGTGAGCTCTGCG
     (SEQ ID NO 27)

(e) anti-TNF alpha VHH with an extension of a single alanine

GAAGTGCAGCTGGTAGAATCTGGCGGTGGTCTGGTACAGCCGGGTGGTTCTCTGCGTCTGTCT
TGCGCAGCTTCTGGCTTCACCTTCTCCGACTACTGGATGTATTGGGTTCGTCAGGCGCCGGGTAAAGGT
CTGGAATGGGTGTCTGAAATCAACACCAACGGCCTGATCACCAAATACCCGGACTCCGTGAAAGGTCGTT
TCACCATCTCCCGCGACAACGCGAAAAACACCCTGTACCTGCAGATGAACTCTCTGCGTCCGGAAGATAC
CGCGGTTTACTATTGTGCGCGTTCTCCGTCTGGTTTCAACCGTGGTCAGGGTACTCTGGTTACCGTAAG
CTCTGGTGGTGGTGGATCCGGCGGTGGTTCTGAAGTTCAGCTGGTTGAAAGCGGTGGTGGTCTGGTAC
AGCCGGGTAACTCTCTGCGTCTGTCTTGTGCGGCTTCTGGCTTCACCTTCTCCTCTTTCGGTATGTCTTG
GGTTCGTCAGGCACCGGGTAAAGGCCTGGAATGGGTTTCCTCTATCTCTGGTAGCGGTTCTGACACCCT
GTACGCTGACTCTGTTAAAGGCCGCTTCACCATCTCCCGTGACAACGCGAAAACCACCCTGTATCTGCAG
ATGAACTCCCTGCGTCCGGAAGATACCGCTGTATACTACTGCACCATCGGTGGCTCTCTGTCTCGTTCTT
CTCAGGGTACCCTGGTTACCGTATCTAGCGGTGGTGGTGGATCCGGTGGCGGTAGCGAAGTTCAGCTGG
TTGAATCTGGCGGTGGTCTGGTTCAGCCGGGTGGTTCTCTGCGTCTGTCTTGTGCAGCGTCTGGCTTCA
CCTTCAGCGATTACTGGATGTACTGGGTTCGTCAGGCACCGGGTAAAGGTCTGGAATGGGTGTCTGAAA
TCAACACCAACGGTCTGATCACCAAATACCCGGACAGCGTGAAAGGTCGTTTCACCATCAGCCGTGACAA
CGCGAAAAACACCCTGTACCTGCAGATGAACTCTCTGCGTCCGGAAGACACTGCGGTTTATTACTGCGCA
CGTTCTCCGTCTGGTTTCAACCGTGGTCAGGGTACCCTGGTTACTGTATCCTCTGCG
     (SEQ ID NO 28)

(f) anti-Von Willebrand VHH with an extension of a single alanine

GAGGTACAGCTGGTGGAAAGCGGTGGTGGTCTGGTTCAGCCGGGTGGTTCTCTGCGTCTGTCTTGCGC
AGCTTCTGGCCGTACCTTCAGCTACAACCCGATGGGTTGGTTCCGTCAGGCTCCGGGTAAAGGTCGTGA
ACTGGTTGCGGCGATCTCTCGTACCGGTGGCTCTACCTACTATCCGGACTCCGTGGAAGGTCGTTTCAC
CATCTCCCGCGACAACGCGAAACGTATGGTATACCTGCAGATGAACAGCCTGCGCGCTGAAGACACCGC
GGTTTACTATTGTGCTGCAGCGGGTGTTCGTGCTGAAGACGGTCGTGTTCGTACCCTGCCGTCCGAATA
CACCTTCTGGGGTCAGGGTACCCAGGTTACCGTTTCTTCTGCAGCGGCGGAAGTGCAGCTGGTTGAATC
TGGCGGTGGTCTGGTACAGCCGGGTGGTTCTCTGCGTCTGTCTTGTGCTGCGTCTGGTCGCACCTTCTC
CTACAACCCGATGGGTTGGTTCCGTCAGGCACCGGGTAAAGGTCGTGAACTGGTAGCGGCAATCTCTCG
CACTGGTGGCTCTACCTACTACCCGGACTCTGTTAAGGCCGCTTCACCATCTCTCGTGACAACGCGAAA
CGTATGGTGTACCTGCAGATGAACTCCCTGCGTGCGGAAGACACCGCAGTTTATTACTGCGCGGCAGCT
GGTGTTCGTGCAGAAGACGGTCGTGTTCGTACCCTGCCGAGCGAATACACCTTCTGGGGTCAGGGTACC
CAGGTAACCGTATCTTCTGCG
     (SEQ ID NO 29)

Figure 11: amino acid sequences of mAb:VL dAbs (a) mAb-VL '735 molecule (IL-13mAb: IL-4Vkappa dAb):

(i) '735 molecule Heavy chain sequence

QVQLVQSGAEVKKPGSSVKVSCKASGFYIKDTYMHWVRQAPGQGLEWMGTIDPANGNTKYVPKFQGRVTI
TADESTSTAYMELSSLRSEDTAVYYCARSIYDDYHVDDYYAMDYWGQGTLVTVSSASTKGPSVFPLAPSSKS
TSGGTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGN
VFSCSVMHEALHNHYTQKSLSLSPGKGSTVAAPSGSTVAAPSGSDIQMTQSPSSLSASVGDRVTITCRASRP
ISDWLHWYQQKPGKAPKLLIAWASSLQGGVPSRFSGSGSGTDFTLTISSLQPEDFATYY
CQQEGWGPPTFGQGTKVEIKR

(SEQ ID NO 30)

(ii) '735 molecule Light chain sequence

DIVMTQSPLSLPVTPGEPASISCRSSQNIVHINGNTYLEWYLQKPGQSPRLLIYKISDRFSGVPDRFSGSGSGTD
FTLKISRVEADDVGIYYCFQGSHVPWTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

(SEQ ID NO 31)

(b) mAb-VL 15014

(i) 15014 molecule Heavy chain sequence

QVTLRESGPALVKPTQTLTLTCTFSGFSLSTSGMGVSWIRQPPGKGLEWLAHIYWDDDKRYNPSLKSRLTIS
KDTSRNQVVLTMTNMDPVDTATYYCARRETVFYWYFDVWGRGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSC
SVMHEALHNHYTQKSLSLSPGKGSTVAAPSTDIQMTQSPSSLSASVGDRVTITCRASRPISDWLHWYQQKP
GKAPKLLIAWASSLQGGVPSRFSGSGSGTDFTLTISSLQP EDFATYYCQQEGWGPPTFGQGTKVEIKRAAA

(SEQ ID NO 32)

(ii) 15014 molecule Light chain sequence

DIVLTQSPSSLSASVGDRVTITCKASQSVDYDGDSYMNWYQQKPGKAPKLLIYAASNLESGIPSRFSGSGSGTDF
TFTISSLQPEDIATYYCQQSNEDPPTFGQGTKVEIKRTVAAPSVFIFPPSDEQLKSGTASVVCLLNNFYPREAKVQ
WKVDNALQSGNSQESVTEQDSKDSTYSLS STLTLSKADYEKHKVYACEVTHQGLSSPVTKSFNRGEC

(SEQ ID NO 33)

Figure 11 continued:

(c) ) mAb-VL 15019

(i) Heavy chain sequence (mAb component is shown in underlined type, linker is shown in italics, VL dAb component follows the linker and is shown in bold)

<u>QVTLRESGPALVKPTQTLTLTCTFSGFSLSTSGMGVSWIRQPPGKGLEWLAHIYWDDDKRYNPSLKSRLTIS
KDTSRNQVVLTMTNMDPVDTATYYCARRETVFYWYFDVWGRGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSC
SVMHEALHNHYTQKSLSLSPGK</u>*GSTVAAPST***DIQMTQSPSSLSASVGDRVTITCRASRPISDWLHW
YQQKPGKAPKLLIAWASSLQGGVPSRFSGSGSGTDFTLTISSLQPEDFATYYCQQEGWGPPTF
GQGTKVEIKRT**

(SEQ ID NO 34)

(ii) mAb-VL 15019 L-chain sequence

DIVLTQSPSSLSASVGDRVTITCKASQSVDYDGDSYMNWYQQKPGKAPKLLIYAASNLESGIPSRFSGSGSG
TDFTFTISSLQPEDIATYYCQQSNEDPPTFGQGTKVEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGE
C

(SEQ ID NO 35)

(d) ) mAb-VL 15020

(i) Heavy chain sequence (mAb component is shown in underlined type, linker is shown in italics, VL dAb component follows the linker and is shown in bold):

<u>QVTLRESGPALVKPTQTLTLTCTFSGFSLSTSGMGVSWIRQPPGKGLEWLAHIYWDDDKRYNPSLKSRLTIS
KDTSRNQVVLTMTNMDPVDTATYYCARRETVFYWYFDVWGRGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSC
SVMHEALHNHYTQKSLSLSPGK</u>*GSTVAAPST***DIQMTQSPSSLSASVGDRVTITCRASRPISDWLHW
YQQKPGKAPKLLIAWASSLQGGVPSRFSGSGSGTDFTLTISSLQPEDFATYYCQQEGWGPPTF
GQGTKVEIKRTV**

(SEQ ID NO 36)

Figure 11 continued:

(d ii) mAb-VL 15020 L-chain sequence

DIVLTQSPSSLSASVGDRVTITCKASQSVDYDGDSYMNWYQQKPGKAPKLLIYAASNLESGIPSRFSGSGSG
TDFTFTISSLQPEDIATYYCQQSNEDPPTFGQGTKVEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGE
C

(SEQ ID NO 37)

(e) ) mAb-VL 15021

(i) Heavy chain sequence (mAb component is shown in underlined type, linker is shown in italics, VL dAb component follows the linker and is shown in bold):

<u>QVTLRESGPALVKPTQTLTLTCTFSGFSLSTSGMGVSWIRQPPGKGLEWLAHIYWDDDKRYNPSLKSRLTIS
KDTSRNQVVLTMTNMDPVDTATYYCARRETVFYWYFDVWGRGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSC
SVMHEALHNHYTQKSLSLSPGK</u>*GSTVAAPST***DIQMTQSPSSLSASVGDRVTITCRASRPISDWLHW
YQQKPGKAPKLLIAWASSLQGGVPSRFSGSGSGTDFTLTISSLQPEDFATYYCQQEGWGPPTF
GQGTKVEIK**

(SEQ ID NO 38)

(ii) mAb-VL 15021 L-chain sequence
DIVLTQSPSSLSASVGDRVTITCKASQSVDYDGDSYMNWYQQKPGKAPKLLIYAASNLESGIPSRFSGSGSGT
DFTFTISSLQPEDIATYYCQQSNEDPPTFGQGTKVEIKRTVAAPSVFIFPPSDEQLKSGTASVVCLLNNFYPRE
AKVQWKVDNALQSGNSQESVTEQDSKDSTYSLSSTLTLSKADYEKHKVYACEVTHQGLSSPVTKSFNRGEC

(SEQ ID NO 39)

Figure 12: amino acid sequences of Vh-Vk dAb-fc-dAb molecules (a) DMS30045: DOM15-26-597 dAb N-(VEPKSSDK linker) & C-terminal K-044-085 dAb ((TGLDSP)x4)

EVQLLVSGGGLVQPGGSLRLSCAASGFTFKAYPMMWVRQAPGKGLEWVSEISPSGSNTYYADSVKGRFTISRDNS
KNTLYLQMNSLRAEDTAVYYCAKDPRKLDYWGQGTLVTVSSVEPKSSDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKTGLDSPTGLDSPTGLDSPTGLDSPDIQMT
QSPSSLSASVGDRVTITCRASQWIGPELKWYQQKPGKAPKLLIYHGSILQSGVPSRFSGSGSGTDFTLTISSLQPEDF
ATYYCQQYMYYPHTFGQGTKVEIKR

(SEQ ID NO 40)

(b) DMS30046: DMS1576 with C-terminal K-044-085 dAb ((TGLDSP)x4)

EVQLLVSGGGLVQPGGSLRLSCAASGFTFKAYPMMWVRQAPGKGLEWVSEISPSGSNTYYADSVKGRFTISRDNS
KNTLYLQMNSLRAEDTAVYYCAKDPRKLDYWGQGTLVTVSSASTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGKTGLDSPTGLDSPTGLDSPTGLDSPDIQMTQSPSSLS
ASVGDRVTITCRASQWIGPELKWYQQKPGKAPKLLIYHGSILQSGVPSRFSGSGSGTDFTLTISSLQPEDFATYYCQQ
YMYYPHTFGQGTKVEIKR

(SEQ ID NO 41)

(c) DMS30047 (contains modified C terminus) : DOM15-26-597 dAb N-(VEPKSSDK linker) & C-terminal K-044-085 dAb minus C-term R ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSVEPKSSDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGKTGLDSPTGLDSPTGLDSPTGLDSP
DIQMTQSPSSLSASVGDRVTITCRASQWIGPELKWYQQKPGKAPKLLIYHGSILQSGVPSRFSGSGSGTDFTLTISSL
QPEDFATYYCQQYMYYPHTFGQGTKVEIK

(SEQ ID NO 42)

Figure 12 continued:

(d) DMS30048 (contains modified C terminus): DOM15-26-597 dAb N-(VEPKSSDK linker) & C-terminal K-044-085 dAb + A ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSVEPKSSDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGKTGLDSPTGLDSPTGLDSPTGLDSP
DIQMTQSPSSLSASVGDRVTITCRASQWIGPELKWYQQKPGKAPKLLIYHGSILQSGVPSRFSGSGSGTDFTLTISSL
QPEDFATYYCQQYMYYPHTFGQGTKVEIKRA

(SEQ ID NO 43)

(e) DMS30049 (contains modified C terminus): DOM15-26-597 dAb N-(VEPKSSDK linker) & C-terminal K-044-085 dAb +AAA ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSVEPKSSDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGKTGLDSPTGLDSPTGLDSPTGLDSP
DIQMTQSPSSLSASVGDRVTITCRASQWIGPELKWYQQKPGKAPKLLIYHGSILQSGVPSRFSGSGSGTDFTLTISSL
QPEDFATYYCQQYMYYPHTFGQGTKVEIKRAAA

(SEQ ID NO 44)

(f) DMS30050 (contains modified C terminus): DOM15-26-597 dAb N-(VEPKSSDK linker) & C-terminal K-044-085 dAb +T ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSVEPKSSDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGKTGLDSPTGLDSPTGLDSPTGLDSP
DIQMTQSPSSLSASVGDRVTITCRASQWIGPELKWYQQKPGKAPKLLIYHGSILQSGVPSRFSGSGSGTDFTLTISSL
QPEDFATYYCQQYMYYPHTFGQGTKVEIKRT

(SEQ ID NO 45)

*Figure 12 continued:*

(g) DMS30051 (contains modified C terminus): DMS1576 with C-terminal K-044-085 dAb minus C-term R ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSASTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKTGLDSPTGLDSPTGLDSPTGLDSPDIQMT
QSPSSLSASVGDRVTITCRASQWIGPELKWYQQKPGKAPKLLIYHGSILQSGVPSRFSGSGSGTDFTLTISSLQPEDF
ATYYCQQYMYYPHTFGQGTKVEIK

(SEQ ID NO 46)

(h) DMS30052 (contains modified C terminus): DMS1576 with C-terminal K-044-085 dAb +A ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSASTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKTGLDSPTGLDSPTGLDSPTGLDSPDIQMT
QSPSSLSASVGDRVTITCRASQWIGPELKWYQQKPGKAPKLLIYHGSILQSGVPSRFSGSGSGTDFTLTISSLQPEDF
ATYYCQQYMYYPHTFGQGTKVEIKRA

(SEQ ID NO 47)

(i) DMS30053 (contains modified C terminus): DMS1576 with C-terminal K-044-085 dAb +AAA ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSASTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKTGLDSPTGLDSPTGLDSPTGLDSPDIQMT
QSPSSLSASVGDRVTITCRASQWIGPELKWYQQKPGKAPKLLIYHGSILQSGVPSRFSGSGSGTDFTLTISSLQPEDF
ATYYCQQYMYYPHTFGQGTKVEIKRAAA

(SEQ ID NO 48)

Figure 12 continued:

(j) DMS30054 (contains modified C terminus): DMS1576 with C-terminal K-044-085 dAb +T ((TGLDSP)x4)

EVQLLVSGGGLVQPGGSLRLSCAASGFTFKAYPMMWVRQAPGKGLEWVSEISPSGSNTYYADSVKGRF
TISRDNSKNTLYLQMNSLRAEDTAVYYCAKDPRKLDYWGQGTLVTVSSASTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKTGLDSPTGLDSPTGLDSPTGLDSPDIQMT
QSPSSLSASVGDRVTITCRASQWIGPELKWYQQKPGKAPKLLIYHGSILQSGVPSRFSGSGSGTDFTLTISSLQPEDF
ATYYCQQYMYYPHTFGQGTKVEIKRT

(SEQ ID NO 49)

FIGURE 13

Table 10A

| Ligand | Ka (M⁻¹s⁻¹) | Kd (s⁻¹) | KC (M) |
|---|---|---|---|
| DMS30037 | 8.18E+06 | 4.34E-05 | 5.30E-12 |
| DMS30037+A | 8.25E+06 | 5.21E-05 | 6.32E-12 |
| DMS30037+AAA | 7.74E+06 | 5.37E-05 | 6.94E-12 |
| DMS30037+T | 8.03E+06 | 4.21E-05 | 5.24E-12 |

FIGURE 14

Table 10B

| Ligand | Ka(1/Ms) | Kd(s⁻¹) | KD(M) |
|---|---|---|---|
| DMS30037 | 1.04E+07 | 4.39E-05 | 4.22E-12 |
| DMS30037+R | 1.07E+07 | 4.22E-05 | 3.94E-12 |
| DMS30037+T | 1.10E+07 | 4.27E-05 | 3.90E-12 |
| DMS30038 | 1.03E+07 | 4.79E-05 | 4.64E-12 |
| DMS30038+R | 1.23E+07 | 5.31E-05 | 4.31E-12 |
| avastin | 8.39E+05 | Out of range | Out of range |

FIGURE 15

Table 10C

| Ligand | ka | kd | KD |
|---|---|---|---|
| DMS30037 | 5.60E+06 | 1.46E-04 | 2.61E-11 |
| DMS30037+T | 5.38E+06 | 1.42E-04 | 2.64E-11 |
| DMS30037-R | 6.97E+06 | 1.55E-04 | 2.22E-11 |
| DMS30038 | 5.69E+06 | 1.55E-04 | 2.73E-11 |
| DMS30038-R | 5.90E+06 | 1.58E-04 | 2.68E-11 |
| DMS30038+T | 8.28E+06 | 1.22E-04 | 1.47E-11 |
| Avastin | 1.24E+06 | Out of range | Out of range |

FIGURE 16

Table 11A

| VEGFR2 RBA | | | EC50 (g/mL) | EC50 (pM) |
|---|---|---|---|---|
| Avastin | | | 1.21E-07 | 806 |
| DMS30037 | | | 2.99E-09 | 28 |
| DMS30037 +T | | | 2.98E-09 | 28 |
| DMS30037 -R | | | 2.66E-09 | 25 |
| DMS30038 | | | 3.37E-09 | 32 |
| DMS30038 -R | | | 3.84E-09 | 37 |

FIGURE 17

Table 11B

| VEGF R2 RBA | EC50 (g/mL) | EC50 (pM) |
|---|---|---|
| Avastin | 3.4E-07 | 2266 |
| DMS30038 | 5.28E-09 | 50 |
| DMS30038 +T | 4.31E-09 | 41 |
| DMS30038 -R | 4.53E-09 | 43 |

MODIFIED PROTEINS AND PEPTIDES

This application is a US National Stage Application under 35 USC § 371 of International Application No. PCT/EP2012/065782 filed Aug. 13, 2012 which claims the benefit of U.S. Provisional Patent Application No. 61/524,488 filed on Aug. 17, 2011; Application No. PCT/EP2012/064632 filed Jul. 25, 2012; Application No. GB 1121226.3 filed Dec. 12, 2011; Application No. GB 1121233.9 filed Dec. 12, 2011; and Application No. GB 1121236.2 filed Dec. 12, 2011. The entire teachings of the above identified applications are incorporated herein by reference.

The present invention relates to modified proteins and peptides that have reduced ability to bind to pre-existing antibodies. Such modified protein/peptide molecules can comprise C-terminal additions, extensions or tags and/or certain amino acid substitutions. Such modified protein/peptide molecules (including fusions and conjugates thereof) may comprise antigen binding molecules, such as antibodies, antibody fragments, and single variable domains e.g. human immunoglobulin (antibody) single variable domains, and also single variable domains derived from non-human sources such as llama or camel, e.g. a VHH including a Nanobody™ (e.g. as described in WO 94/04678 and WO 95/04079 inter alia). The invention further relates to uses, formulations, compositions comprising such modified C-terminally extended and/or amino acid substituted molecules and also to methods of production and expression of these molecules.

BACKGROUND OF THE INVENTION

Naturally occurring autoantibodies exist in humans that can bind to proteins e.g. to host immunoglobulins or immunoglobulin fragments e.g. Rheumatoid factor (which bind epitopes in the Fc region of antibodies), anti-idiotype autoantibodies (which bind antibody variable/CDR regions) and anti-hinge autoantibodies (which bind the hinge region of the Ig constant domain in Fab fragments).

These autoantibodies may be part of a polyclonal repertoire of anti-immunoglobulin (Ig) autoantibodies with specificity to epitopes throughout the Ig molecule that are present in both humans and non-human primates. In addition to the anti-IgG autoantibodies that bind epitopes within the intact Fc domain (i.e. the rheumatoid factors (RF)), the presence of anti-idiotypic autoantibodies that bind to variable CDR regions of IgG, and anti-hinge antibodies that react with cryptic epitopes in the C terminal hinge regions of Fab or F('Ab')$_2$ fragments has also been observed. The functional role of these different anti-IgG autoantibodies remains uncertain. Rheumatoid factor and anti-hinge autoantibodies have been linked with certain pathological conditions, such as autoimmunity and certain infections while anti-idiotypic antibodies may confer protection from autoantibodies in certain autoimmune diseases. Furthermore, an immunoregulatory role for anti-IgG autoantibodies, has been proposed wherein these autoantibodies control the stimulation of autoreactive B cells and regulate immune responses to foreign antigens. Anti-hinge antibodies are anti-IgG autoantibodies that react with cleaved but not intact IgG. Their high prevalence in the normal human population implicates previous exposure to IgG fragments, possibly as a result of cleavage of IgG by bacterial or endogenous proteases.

As well as binding to endogenous proteins (present in naïve subjects) autoantibodies can also bind to proteins or peptides which are administered to a subject for treatment. Pre-existing antibodies which bind to molecules such as therapeutic proteins and peptides, administered to a subject can affect their efficacy and could result in administration reactions, hypersensitivity, altered clinical response in treated patients as well as altered bioavailability by sustaining, eliminating or neutralizing the molecule. However in some instances existence of these antibodies may be less significant during drug treatment than in other instances.

Therapeutic protein-binding autoantibodies and antibodies that are newly formed in response to drug treatment (such as administration of a therapeutic protein or peptide) are collectively termed anti-drug antibodies (ADAs). When ADAs are described throughout this document we are referring to pre-existing ADAs unless specifically stated otherwise.

VH and VL domain antibodies are derived from fully human framework sequences and although in silico predictions describe a markedly low incidence of potentially immunogenic peptides, it is possible that these domain antibodies may be immunogenic in humans i.e. they could elicit ADAs, and they could bind to pre-existing ADAs depending on both sequence dependent and sequence independent factors.

Similarly, a number of single dAbs derived from the Camelid heavy chain (VHH) are under investigation in the clinic and whilst no hypersensitivity or other immune-mediated adverse events have been reported binding to pre-existing ADAs remains a possibility.

It could thus be advantageous to provide molecules for therapy which comprise proteins, or peptides, for example antigen binding molecules, which have reduced ability to bind to pre-existing ADAs when administered to a subject, in particular a human subject)

SUMMARY OF THE INVENTION

We have demonstrated as described herein that in sera from some healthy naïve human subjects, pre-existing anti-VH autoantibodies are present that can bind both VH domain antibodies and VHH molecules, as well as anti-VL (e.g. V kappa (VK)) autoantibodies that can bind VL molecules. The pre-existing ADAs that bind VH dAbs are similar to anti-hinge antibodies in that they bind IgG fragments but not those same sequences found in situ on intact IgG.

A specific immunoassay was developed as described herein and validated to detect anti-drug antibodies to the VH dAb DOM1H-131-206 (amino acid sequence shown in SEQ ID NO 1) in humans. A panel of 60 healthy human donor serum samples was screened for background reactivity in the assay. It was determined that approximately 45% of serum samples from these subjects had detectable antibodies, which were able to bind to DOM1H-131-206. This reactivity appears specific to a neo epitope, or epitopes, within the VH dAb framework sequence, since the response was cross-reactive with the VH frameworks of dAbs binding various target antigens, but not with full human IgG. Pre-existing ADA to VL dAbs was also observed in serum samples from healthy human donors but to a lower extent than VH.

Taking a mutagenesis approach, we determined whether modifications to the VH framework could reduce the binding of these pre-existing ADAs. Using this approach we mapped an epitope to the C-terminus of the VH dAb framework, and we exemplify a number of approaches which can be used to reduce or eliminate the binding of the pre-existing antibodies to VL, VH and VHH molecules. In particular, we have shown that modifications which alter the three dimensional conformation of the dAb C-terminus, in particular the C-terminal serine residue (i.e. at Kabat position 113) in VH and VHH dAbs are important. In addition the three dimensional conformation of the dAb C-terminus can be altered by the addition of further amino add residues (C-terminal extension) and/or by substituting the amino acid residues present at one or more of positions 14, 41, 108, 110 and 112 in VH dAbs.

The present invention thus provides modified molecules that have reduced ability to bind to (pre-existing) ADAs as compared to the unmodified molecule and are suitable for administration to a subject e.g. a human subject for therapy or prophylaxis. By reduced ability to bind is meant that the molecule binds with a reduced affinity or reduced avidity to a pre-existing ADA. Such molecules comprise proteins, or peptides, for example antigen binding proteins, e.g. antibodies, antibody fragments, and single variable domains e.g. human immunoglobulin (antibody) single variable domains (VH or VL), and also single variable domains derived from non-human sources such as llama or Camelid, e.g. a Camelid VHH including a Nanobody™ (described for example in WO 94/04678 and WO 95/04079 inter alia). Said molecules comprise one or more modifications selected from: (a) a C-terminal addition, extension, deletion or tag, and/or (b) one or more amino acid framework substitutions.

Additionally, the modified molecules described herein and pharmaceutical compositions comprising these modified molecules can have an enhanced safety profile and fewer side effects than the unmodified molecules e.g. unmodified dAbs, which do not comprise a C terminal extension, addition, deletion or tag and/or other framework modification, to reduce pre-existing ADA binding. Similarly, administration of the modified molecules described herein or of pharmaceutical compositions comprising these modified molecules (which have reduced ability to bind to pre-existing ADA) can lead to modified immunogenicity and can also result in improved efficacy and an improved safety profile and e.g. can be advantageously used for repeat dosing to patients who could develop autoantibodies to the unmodified molecules e.g. dAbs.

Thus in a first aspect of the invention there is provided:
a single immunoglobulin variable domain (dAb), which comprises one or more modifications selected from: (a) a C-terminal extension which comprises an amino acid extension of from one amino acid to 5 amino acids; or (b) one or more amino acid framework substitutions wherein at least one substitution is a substitution selected from: a P14A substitution, a P41A substitution and a L108A substitution.

In one embodiment, a C-terminal extension of from one to 4 amino acids is provided. In another embodiment said C-terminal extension comprises an amino acid which is alanine, and which has reduced binding to pre-existing ADAs compared to the unmodified single immunoglobulin variable domain (dAb).

In another aspect the C terminal extension can be an extension of 1-15 amino acids e.g. 1 to 8 amino acids or 1, 1-2, 1-3, 1-4, 1-5, 1-6, 1-7 amino acids. In particular an extension of 1 to 8 amino acids, or 1, 1-2, 1-3, 1-4, 1-5, 1-6, 1-7 amino acids which comprises an alanine residue, for example a single alanine extension, or an AS, AST, ASTK, ASTKG, ASTKGP extension. In particular an extension of 1-5 amino acids is provided or an extension of 1-4 amino acids. The modified single immunoglobulin variable domain can also comprise an amino acid deletion. The single immunoglobulin variable domain (dAb) can be selected from a human VH, or human VL dAb or a Camelid VHH. The C-terminal extension can be present as a direct fusion or a conjugate with the C terminus of the dAb.

In another aspect, the invention provides a single immunoglobulin variable domain (dAb) wherein (i) said dAb is a human VH or a Camelid VHH and said C terminal extension comprises an amino acid extension selected from (a) A (b) AS, (c) AST (d) ASTK, (e) ASTKG (f) AAA or (g) T; and wherein (ii) said dAb is a human VL (such as a V kappa) and said C terminal extension comprises an amino acid extension selected from (a) AAA, (b) A (c) TV (d) T.

The invention also provides a single immunoglobulin variable domain (dAb) which monovalently binds to a target antigen, comprising:
a) three complementarity determining (CDR) regions specific for said target antigen; such that said dAb binds said antigen with a KD in the range of 5 micromolar to 1 picomolar
b) four framework (FW) regions; and
c) a C-terminal sequence consisting of the sequence VTVS(S)$_n$X or VEIK$_p$R$_q$X; and optionally
d) one or more amino acid substitutions at positions 14, 41, 108, 110, or 112 compared to a human germline framework sequence wherein:
$_n$ represents an integer independently selected from 0 or 1;
$_p$ and $_q$ each represent 0 or 1 such that when $_p$ represents 1 $_q$ may be 0 or 1 and such that when $_p$ represents 0, $_q$ also represents 0;
X may be present or absent, and if present represents an amino acid extension of 1 to 8 amino acids residues;
with the further proviso that if X is absent;
i) $_n$ is 0 and/or the dAb ending in VTVS(S)$_n$ comprises one or more of said amino acid substitutions;
ii) $_p$ and/or $_q$ is 0, and/or the dAb ending in VEIK$_p$R$_q$X comprises one or more of said amino acid substitutions.

KD refers to the equilibrium dissociation constant. A skilled person will appreciate that the smaller the KD numerical value, the stronger the binding.

In one embodiment of this aspect said dAb binds said antigen with a KD in the range of about 10 pM to about 50 nM.

In one embodiment of this aspect, said single immunoglobulin variable domain (dAb) has a lower binding affinity and/or avidity for an anti-drug antibody (ADA) than an equivalent dAb wherein said equivalent dAb has the same sequence as said single immunoglobulin variable domain except that X is absent, $_n$, $_p$ and $_q$ are 1 and there are no amino acid substitutions.

In a further embodiment, said single immunoglobulin variable domain is one wherein said C terminal sequence consists of the sequence VTVSSX.

In another embodiment said single immunoglobulin variable domain is one wherein said C terminal sequence consists of the sequence VEIKRX.

In a further embodiment, said single immunoglobulin variable domain has one or more amino acid substitutions selected from the group consisting of: a P14A substitution, a P41A substitution, a L108A substitution, a T110A substitution and a S112A substitution.

In embodiment, X is present, and is an extension of 1 to 8 amino acids or 1, 1-2, 1-3, 1-4, 1-5, 1-6, 1-7 amino acids, in particular an extension of 1 to 8 amino acids, or 1, 1-2, 1-3, 1-4, 1-5, 1-6, 1-7 amino acids which comprises an alanine residue, for example a single alanine extension, or an AS, AST, ASTK, ASTKG, ASTKGP extension.

In a further embodiment, said dAb is a VH, or VL dAb or a Camelid VHH.

In yet a further aspect the invention also provides an amino acid sequence which is any one of the unmodified single immunoglobulin variable domain (dAb) sequences described herein (for example SEQ ID NOs 1-6, 10-13) which is then modified to reduce binding to ADAs as described herein, for example an unmodified single immunoglobulin variable domain sequence described herein which is modified such that X is present, and is an extension of 1 to 8 amino acids, in particular an extension of 1 to 8 amino acids which comprises an alanine residue, for example a single alanine extension, or an AS, AST, ASTK, ASTKG, ASTKGP extension and/or said single immunoglobulin variable domain has one or more amino acid substitutions wherein said one or more amino acid substitutions are selected from the group consisting of a P14A substitution, a P41A substitution, a L108A substitution, a T110A substitution and a S112A substitution.

In one embodiment the invention provides a single immunoglobulin variable domain which is a human VH or a Camelid VHH and said C terminal extension comprises an amino acid extension selected from: (a) AS, (b) AST (c) ASTK, (d) ASTKG (e) MA or (f) T or (g) ASTKGP, and/or wherein there is an amino acid deletion from the dAb ending in VTVS(S)$_n$ and said deletion is a —S deletion.

In another embodiment the invention provides a single immunoglobulin variable domain which is a human VL e.g. V kappa, and wherein said C terminal extension comprises an amino acid extension selected from: (a) MA (b) A (c) TV and (d) T, and/or wherein there is an amino acid deletion from the dAb ending in VEIKR and said deletion is a —R deletion.

In one alternative embodiment of previous aspects of the invention when the C-terminal sequence for a VL dAb is VEIKRAAA or VEIKRT, antigen binding constructs comprising two dAbs separated by a single chain Fc region of an antibody, wherein each dAb is capable of binding to VEGF, are excluded.

In one aspect the dAbs modified to reduce binding to ADA as described herein (e.g. VH, VL such as V kappa and VHH) have a KD of binding to ADA which is 150% or more (e.g. 200%, 250%, 300%, 350%, 400%, 450%, 500%, 550%, 600%, 650% or more) of the KD of an equivalent but unmodified single immunoglobulin variable domain (dAb) sequence. Also provided by the invention is dAb modified as described herein to have reduced ADA binding and which has reduced binding to ADAs as determined using a confirmation assay as described in Example 2 and where said modified dAb has a mean % inhibition of signal which is less than 90%, e.g. less than 80%, e.g. less than 70%, e.g. less than 60%, e.g. less than 50%, e.g. less than 40%, e.g. less than 30%, e.g. less than 20%, e.g. less than 10%, in comparison with a control dAb which has around 98%-100% inhibition of signal, said control (unmodified) dAb has the same or similar sequence but is not modified to reduce ADA binding.

The present invention also provides an immunoglobulin single variable domain (dAb) of the invention for use in a method of therapy, for example for use in a method of preventing side effects. This use may be of particular benefit where the dAb is an antagonist of the target e.g. a target selected from TNFα, TNF receptor, TNF receptor 1 (TNFR1), VEGF, IL-1R, IL-6R, IL-4, IL-5, IL-13, DC-SIGN, ASGPR, albumin, and TGFβR2. In one embodiment the target is a receptor, or in particular a receptor which is polymeric or a receptor which dimerizes on activation, for example the TNF receptor. In another embodiment the dAb modified as described herein such that it has reduced binding to ADAs is to be used in a treatment regimen which involves repeated dosing.

The invention provides a single immunoglobulin variable domain (dAb) wherein the target is TNFR1, and which is dAb selected from any of the following amino acid sequences identified as: (a) DOM1h-131-206 dAb with an extension of a single alanine at the C terminus (SEQ ID NO 16); (b) DOM1h-131-206 dAb with an extension of a single alanine at the C terminus and a P14A framework mutation (SEQ ID NO 17); (c) DOM1h-131-206 dAb with a P14A framework mutation (SEQ ID NO 18); (d) DOM1h-131-206 dAb with an ASTKG C terminus extension (SEQ ID NO 19); and (e) DOM1h-131-206 dAb with an ASTKG C terminus extension and a P14A amino acid framework mutation (SEQ ID NO 20). The invention also provides an (unmodified) dAb which is selected from a sequence that is 100%, 99.5%, 99%, 98%, 97%, 96%, 95%, 90%, 85% or 80% identical to any one of the amino acid sequences identified as: DOM1h-131-206 (SEQ ID NO 1), DOM 1h-131-511 (SEQ ID NO 2), DOM 1h-131-202 (SEQ ID NO 3) and which further comprises any including e.g. any of the modifications described herein which reduce binding to ADAs, e.g. a single alanine C-terminus extension.

The dAbs of the invention include any one of the dAb amino acid sequences described herein or that are part of molecules described herein (or an amino acid sequence that is 100%, 99.5%, 99%, 98%, 97%, 96%, 95%, 90%, 85% k or 80% identical to such a dAb sequence), for example any one of the dAbs described in any of the examples herein and which e.g. comprises any of the modifications described herein to reduce binding to ADAs such as a C-terminal alanine extension. The invention also comprises any one of the molecules described herein (e.g. in the examples) comprising a dAb sequence as described above which comprises any of the modifications described herein to reduce binding to ADAs, such molecules can be for example any one of the Vh-Vk dAb-Fc-dAbs in Example 12, or any of the mAbd-Abs described herein e.g. in the examples herein.

Thus the invention provides an anti-IL13 dAb, for example a dAb with an amino acid sequence that is 100%, 99.5%, 99%, 98%, 97%, 96%, 95%, 90%, 85% k or 80% identical to any one of the amino acid sequences identified as: (a) DOM10h-53-567 (SEQ ID NO 13) or (b) DT04-H-033 (SEQ ID NO 12); and which amino acid sequence further comprises any of the modifications described herein which reduce binding to ADAs e.g. a single alanine C-terminus extension.

The invention also provides an anti-TNFR1dAb, for example a dAb with an amino acid sequence that is 100%, 99.5%, 99%, 98%, 97%, 96%, 95%, 90%, 85% or 80% identical to the amino acid sequences identified as: DOM1h-574-208 (SEQ ID NO 10); and which further comprises any of the modifications described herein which reduce binding to ADAs, e.g. a single alanine C-terminus extension.

The invention also provides an anti-TNFR1dAb-VL fusion, for example with an amino acid sequence that is 100%, 99.5%, 99%, 98%, 97%, 96%, 95%, 90%, 85% or 80% identical to the amino acid sequences identified as: DOM1h-574-208-VL fusion (SEQ ID NO 11); and which further comprises any of the modifications described herein which reduce binding to ADAs e.g. a single (or a triple) alanine extension present at the C-terminus of the fusion molecule.

The invention also provides a mAbdAb which is an anti-IL13mAb: IL-4 V kappa dAb which further comprises any of the modifications described herein which reduce binding to ADAs; for example the mAbdAb can comprise a heavy chain sequence with an amino acid sequence that is 100%, 99.5%, 99%, 98%, 97%, 96%, 95%, 90%, 85% or 80% identical to the amino acid sequences identified as: mAb-VL '735 heavy chain molecule SEQ ID NO 30; and a light chain sequence identified as '735 light chain sequence SEQ ID NO 31; and which further comprises any of the modifications described herein which reduce binding to ADAs e.g. a single (or a triple) alanine extension.

The invention also provides a mAbdAb which is an anti-IL13mAb: IL-4 V kappa dAb designated mAb-VL 15014 modified to reduce binding to ADAs as described herein, wherein the mAbdAb comprises (a) a heavy chain-linker-V kappa sequence with an amino acid sequence that is 100%, 99.5%, 99%, 98%, 97%, 96%, 95%, 90%, 85% or 80% identical to the amino acid sequences identified as SEQ ID NO 32; and (b) a light chain sequence with an amino acid sequence that is 100%, 99.5%, 99%, 98%, 97%, 96%, 95%, 90%, 85% or 80% identical to the amino acid sequences identified as SEQ ID NO 33.

The invention also provides a mAbdAb which is an anti-IL13mAb: IL-4 V kappa dAb designated mAb-VL 15019 modified to reduce binding to ADAs as described herein, wherein the mAbdAb comprises (a) a heavy chain-linker-V kappa sequence with an amino acid sequence that is 100%, 99.5%, 99%, 98%, 97%, 96%, 95%, 90%, 85% or 80% identical to the amino acid sequences identified as SEQ ID NO 34; and (b) a light chain sequence with an amino acid sequence that is 100%, 99.5%, 99%, 98%, 97%, 96%, 95%, 90%, 85% or 80% identical to the amino acid sequences identified as SEQ ID NO 35.

The invention also provides a mAbdAb which is an anti-IL13mAb: IL-4 V kappa dAb designated mAb-VL 15020 modified to reduce binding to ADAs as described herein, wherein the mAbdAb comprises (a) a heavy chain-linker-V kappa sequence with an amino acid sequence that is 100%, 99.5%, 99%, 98%, 97%, 96%, 95%, 90%, 85% or 80% identical to the amino acid sequences identified as SEQ ID NO 36; and (b) a light chain sequence with an amino acid sequence that is 100%, 99.5%, 99%, 98%, 97%, 96%, 95%, 90%, 85% or 80% identical to the amino acid sequences identified as SEQ ID NO 37.

The invention also provides a mAbdAb which is an anti-IL13mAb: IL-4 V kappa dAb designated mAb-VL 15021 modified to reduce binding to ADAs as described herein, wherein the mAbdAb comprises (a) a heavy chain-linker-V kappa sequence with an amino acid sequence that is 100%, 99.5%, 99%, 98%, 97%, 96%, 95%, 90%, 85% or 80% identical to the amino acid sequences identified as SEQ ID NO 38; and (b) a light chain sequence with an amino acid sequence that is 100%, 99.5%, 99%, 98%, 97%, 96%, 95%, 90%, 85% or 80% identical to the amino acid sequences identified as SEQ ID NO 39.

The invention also provides a VHH sequence with any one of the modifications described herein to reduce binding to ADAs, for example a VHH with an amino acid sequence that is 100%, 99.5%, 99%, 98%, 97%, 96%, 95%, 90%, 85% or 80% identical to any one of the amino acid sequences identified as SEQ ID NO 7-9.

The invention also provides nucleic acids encoding any one of the dAbs of the invention e.g. any one of the nucleic acids described herein e.g. any one of the nucleic acid sequences shown in FIG. 9 (SEQ ID NOs 21-23) or FIG. 10 (SEQ ID NOs 24-29). In one embodiment the invention provides a nucleic acid (SEQ ID NO 22) which encodes the DOM1h-131-206 dAb with an extension of a single alanine at the C-terminus, a vector comprising the nucleic add (SEQ ID NO 22) and it also provides also a host cell, e.g. an *E. coli* host cell, expressing the nucleic acid (SEQ ID NO 22), or a vector such as the Pave011 (from Fujifilm Diosynth) expressing SEQ ID NO 22. Also provided is a method of producing the DOM1h-131-206 dAb with an extension of a single alanine at the C-terminus which comprises maintaining a host cell such as *E. coli* comprising a vector such as Pave011 (or nucleic acid) encoding nucleic acid (SEQ ID NO 22) under conditions suitable for expression of the extended dAb thereby producing the polypeptide.

The dAbs of invention can also be present as fusions or conjugates with other molecules.

In other embodiments of the invention described throughout this disclosure, instead of the use of a "dAb" in a fusion of the invention, it is contemplated that the skilled addressee can use a domain that comprises the CDRs of a dAb that binds its target and which framework comprises the modifications as described herein to reduce binding to ADAs.

Also provided are pharmaceutical compositions comprising a dAb according to any aspect or embodiment of the invention e.g. in combination with a pharmaceutically or physiologically acceptable carrier(s), excipient(s) or diluents(s).

The invention further provides uses of the dAbs of the invention for therapy or medicine and uses to treat or prevent diseases or disorders. For example anti-TNFR1 dAbs with reduced ADA binding, e.g. the DOM1h-131-206 dAb modified as described herein to reduce ADA binding (e.g. those with amino acid sequences shown in FIG. 8a-8e: SEQ ID NOS 16-20).

In one aspect the invention provides use of the DOM1h-131-206 dAb with a C terminal alanine extension (SEQ ID NO 16) for use in therapy or medicine or as a medicament, e.g. to treat or prevent an inflammatory disease or disorder or a respiratory or pulmonary disease or disorder such as Acute lung injury (ALI) and Acute Respiratory Distress syndrome (ARDS) and complications thereof.

The invention also provides nucleic acids encoding the dAbs of the invention with reduced ADA binding and vectors and host cells comprising these nucleic acids. Also provided are methods of producing the dAbs of the invention comprising expressing the encoding vectors and nucleic acids in host cells e.g. microbial host cells such as *E. coli*.

In a further aspect the invention provides formulations comprising the dAbs of the invention with reduced ADA binding, for example nebulisable formulations for pulmonary delivery. Also provided are nebulisers or inhaler devices comprising the dAbs of the invention e.g. any one of the anti-TNFR1 dAbs e.g. those with amino add sequences shown in FIG. 8a-8e: SEQ ID NOS 16-20, for example the DOM1h-131-206 dAb with a C terminal alanine extension (SEQ ID NO 16).

In another aspect the invention provides the unmodified DOM1h-131-206 dAb (SEQ ID NO1) or the DOM1h-131-206 dAb modified in any of the ways described herein to reduce ADA binding e.g the DOM1h-131-206 dAb with an extension of a single alanine at the C-terminus (SEQ ID NO 16), to treat an inflammatory skin disorder e.g. psoriasis.

Another aspect of the disclosure is a method of treating psoriasis in a human comprising the steps of a) identifying a human with psoriasis; and b) administering a therapeutically effective amount of a domain antibody (e.g. the unmodified DOM1h-131-206 dAb (SEQ ID NO1) or the DOM1h-131-206 dAb modified in any of the ways described herein to reduce ADA binding e.g the DOM1h-131-206 dAb with an extension of a single alanine at the C-terminus (SEQ ID NO 16) to a psoriatic plaque on the human with psoriasis; whereby the psoriasis is treated.

Another aspect of the disclosure is a domain antibody for use in the treatment of psoriasis and also a dosage regimen for use of a domain antibody for use in the treatment of psoriasis. The domain antibody can be the unmodified DOM1h-131-206 dAb (SEQ ID NO1) or the DOM1h-131-206 dAb modified in any of the ways described herein to reduce ADA binding e.g the DOM1h-131-206 dAb with an extension of a single alanine at the C-terminus (SEQ ID NO 16).

In a further aspect the invention also provides a tool mAb (for example the tool mAb as described in Example 19 and with the amino acid sequence given in FIG. 6: SEQ ID NOs 14 and 15). The tool mAb was generated using standard mouse monoclonal antibody technology i.e. mice were immunised with DOM 1H-131-206 (SEQ ID NO1), spleens were collected and hybridoma cell lines were generated, the hybridomas expressing antibody were then cloned and the resulting antibody isolated and sequenced using standard techniques. The tool mAb is one which binds to the VH dAb framework and thereby reduces binding of the VH dAbs to ADAs. Thus the tool mAb appears to bind to a similar epitope on the VH framework to the human anti-VH ADA. Thus the tool mAb can be useful for example it can be used to test modified dAbs (VH, VHH,) and to determine which modifications to the dAb prevent or reduce binding of the dAb to the tool mAb. Modifications to the VH dAbs which prevent binding to the tool mAb will also prevent or reduce binding of VH dAbs to the ADAs. Thus the invention provides any dAbs which are modified (e.g. by any of the modifications described herein) to prevent or reduce binding to the tool mAb. The invention also provides a method of using a tool mAb (for example the tool mAb described in Example 19 and with the amino acid sequence given in Example 19 and also in FIG. 6: SEQ ID NOs 14 and 15) in an assay to test dAbs e.g. modified dAbs (e.g. (VH, VHH), e.g. any of those described herein e.g. TNFR1 dAbs such as those described herein) and to determine those with reduced binding to ADAs e.g. In one aspect the dAbs (e.g. (VH, VHH) are modified to reduce binding to the tool mAb as described herein and have a KD of binding to the tool mAb which is 150% or more (e.g. 200%, 250%, 300%, 350%, 400%, 450%, 500%, 550%, 600%, 650% or more) of the KD of an equivalent dAb sequence which has not been modified. The invention also provides any dAbs identified by this screening assay.

In a further aspect the invention also provides use of the tool mAb (for example the tool mAb described in Example 19 and with the amino acid sequence given in FIG. 6: SEQ ID NOs 14 and 15) in an assay method to quantify how much dAb (e.g. VH, VHH), is present in a tissue sample or plasma sample.

BRIEF DESCRIPTION OF THE DRAWINGS

FIG. 1: shows Frequency of pre-existing anti-drug antibodies in sera of a panel of healthy human subjects FIG. 2: shows amino acid sequences of unmodified anti-TNFR1 dAbs identified as (a) (unmodified) DOM 1H-131-206 (SEQ ID NO 1) (b) (unmodified) DOM 1H-131-511 (SEQ ID NO 2) (c) (unmodified) DOM 1H-131-202 (SEQ ID NO 3; and VHH sequences identified as (d) which is a bispecific format, having an IL6R binding module linked by GGGGSGGGS to a human serum albumin binding module as described in WO2010100135 (SEQ ID NO 4), (e) is a bispecific format, having TNF binding module linked to a serum albumin binding module in turn linked to a TNF binding module, using GGGGSGGGS as linker as described in WO2010077422 (SEQ ID NO 5), (f) is a bivalent mono-specific format comprising two identical modules linked by an Ala-Ala-Ala linker, each module is a dAb which can bind the A1 domain of the Von-Willebrand factor, as shown in WO2009115614A2 (SEQ ID NO 6), (g) Clone VHH2(d) is a bispecific format, having an IL6R binding module linked by GGGGSGGGS to a human serum albumin binding module as described in WO2010100135 with an alanine extension (SEQ ID NO 7) (h) bispecific format, having TNF binding module linked to a serum albumin binding module in turn linked to a TNF binding module, using GGGGSGGGS as linker as described in WO2010077422 with an alanine extension (SEQ ID NO 8) (i) a bivalent mono-specific format comprising two identical modules linked by an Ala-Ala-Ala linker, each module is a dAb which can bind the A1 domain of the Von-Willebrand factor, as shown in WO2009115614A2 with an alanine extension (SEQ ID NO 9) (j) DOM 1H-574-208 (SEQ ID NO 10) (k) DOM 1H-574-208-VL fusion (SEQ ID NO 11) (l) DT04-H-033 (SEQ ID NO 12); (m) Dom10h-53-567 (SEQ ID NO 13).

FIG. 4: Shows the abrogation of binding to ADAs caused by the addition of a single alanine amino acid residue extension to VHH clones 2(d), 2(e) and 2(f).

FIG. 5: shows levels of binding to ADA s and of $V_H$ dAbs or $V_L$ dAbs or molecules comprising these dAbs.

FIGS. 6a and 6b: shows the amino acid sequences of the tool mAb (M2.3G10.1G06), FIG. 6a shows the light chain sequence (SEQ ID NO 14); and FIG. 6b shows the heavy chain sequence. The CDRs are shown underlined in the figure (SEQ ID NO 15).

FIG. 7: shows competition assay signal (x-axis) in the presence of serum samples from subjects with a range of pre-existing anti-VH ADA signal. Serum from a range of human donors with pre-existing anti-VH ada competes with anti-VH mAb M2.3G10.1G06 for binding to DOM 1H-131-206 resulting in inhibition of competition assay signal.

FIG. 8: shows the amino acid sequences of modified TNFR1 dAbs identified as: (a) DOM1h-131-206 dAb with an extension of a single alanine (SEQ ID NO 16); (b) DOM1h-131-206 dAb with an extension of a single alanine and a P14A framework mutation (SEQ ID NO 17); (c) DOM1h-131-206 dAb with a P14A framework mutation (SEQ ID NO 18); (d) DOM1h-131-206 dAb with an ASTKG C terminus extension (SEQ ID NO 19); and (e) DOM1h-131-206 dAb with an ASTKG C terminus extension and a P14A framework mutation (SEQ ID NO 20).

FIG. 9: shows the nucleic acid sequences of TNFR1 dAbs (a) DOM1h-131-206 dAb (SEQ ID NO 21) (b) DOM1h-131-206 dAb with an extension of a single alanine at the C terminus (SEQ ID NO 22) (c) DOM1h-131-206 dAb with a C terminus extension of ASTKG (SEQ ID NO 23).

FIG. 10: shows the nucleic acid sequences encoding (a) VHH sequence having the amino acid sequence shown in FIG. 2d (SEQ ID NO 24) (b) VHH sequence having the amino acid sequence shown in FIG. 2e (SEQ ID NO 25); (c) VHH sequence having the amino add sequence shown in FIG. 2f (SEQ ID NO 26), (d) VHH sequence which is a bispecific format, having an IL6R binding module linked by GGGGSGGGS to a human serum albumin binding module with an extension of a single alanine (SEQ ID NO 27), (e) VHH sequence with the amino acid sequence shown in 2e further comprising an extension of a single alanine (SEQ ID NO 28), (f) VHH sequence with amino acid sequence shown in 2f further comprising an extension of a single alanine (SEQ ID NO 29).

FIG. 11: shows amino acid sequences of mAb:VL dAbs (IL-13mAb: IL-4Vkappa dAb molecules): (a) mAb-VL '735 molecule (IL-13mAb: IL-4Vkappa dAb) (SEQ ID NOs 30 and 31), (b) mAb-VL 150154 (SEQ ID NOs 32 and 33), (c) mAb-VL 15019 (SEQ ID NOs 34 and 35), (d)) mAb-VL 15020 (SEQ ID NOs 36 and 37), (e) mAb-VL 15021 (SEQ ID NOs 38 and 39).

FIG. 12: shows amino acid sequences of (a) DMS30045: DOM15-26-597 dAb N-(VEPKSSDK linker) & C-terminal K-044-085 dAb ((TGLDSP)×4) (SEQ ID NO 40), (b) DMS30046: DMS1576 with C-terminal K-044-085 dAb ((TGLDSP)×4) (SEQ ID NO 41), (c) DMS30047 (contains modified C terminus): DOM15-26-597 dAb N-(VEPKSSDK linker) & C-terminal K-044-085 dAb minus C-term R ((TGLDSP)×4) (SEQ ID NO 42), (d) DMS30048 (contains modified C terminus): DOM15-26-597 dAb N-(VEPKSSDK linker) & C-terminal K-044-085 dAb +A ((TGLDSP)×4) (SEQ ID NO 43), (e) DMS30049 (contains modified C terminus): DOM15-26-597 dAb N-(VEPKSSDK linker) & C-terminal K-044-085 dAb +AAA ((TGLDSP)×4) (SEQ ID NO 44), (f) DMS30050 (contains modified C terminus): DOM15-26-597 dAb N-(VEPKSSDK linker) & C-terminal K-044-085 dAb +T ((TGLDSP)×4) (SEQ ID NO 45), (g) DMS30051 (contains modified C terminus): DMS1576 with C-terminal K-044-085 dAb minus C-term R ((TGLDSP)×4) (SEQ ID NO 46), (h) DMS30052 (contains modified C terminus): DMS1576 with C-terminal K-044-085 dAb +A ((TGLDSP)×4) (SEQ ID NO 47), (i) DMS30053 (contains modified C terminus): DMS1576 with C-terminal K-044-085 dAb +AAA ((TGLDSP)×4) (SEQ ID NO 48), (j) DMS30054 (contains modified C terminus): DMS1576 with C-terminal K-044-085 dAb +T ((TGLDSP)×4) (SEQ ID NO 49).

FIG. 13 shows Table 10A: Binding of the anti-VEGF dAb-Fc-dAb molecule: DMS30037 with C-terminal modifications to $VEGF_6s$ and comparison to DMS30037.

FIG. 14 shows Table 10B: Binding of the anti-VEGF dAb-Fc-dAb molecules: DMS30037 and DMS30038 with 20 C-terminal modifications to $VEGF_6s$ and comparison to parental dAb-Fc-dAb and Bevacizumab(Avastin).

FIG. 15 shows Table 10C: Binding of the anti-VEGF dAb-Fc-dAb molecules: DMS30037 and DMS30038 with C-terminal modifications to VEGF165 and comparison to parental dAb-Fc-dAb and Bevacizumab(Avastin).

FIG. 16 shows Table 11A: $EC_{50}$ values of anti-VEGF dAb-Fc-dAbs with C-terminal modifications compared to Bevacizumab (Avastin) in VEGFR2 Receptor Binding Assay. Curve fitting and $EC_{50}$ calculations were performed using GraphPad Prism.

FIG. 17 shows Table 11B: $EC_{50}$ values of anti-VEGF dAb-Fc-dAbs with C-terminal modifications compared to Bevacizumab (Avastin) in VEGFR2 Receptor Binding Assay. Curve fitting and $EC_{50}$ calculations were performed using GraphPad Prism.

DETAILED DESCRIPTION OF THE INVENTION

Figure 3:
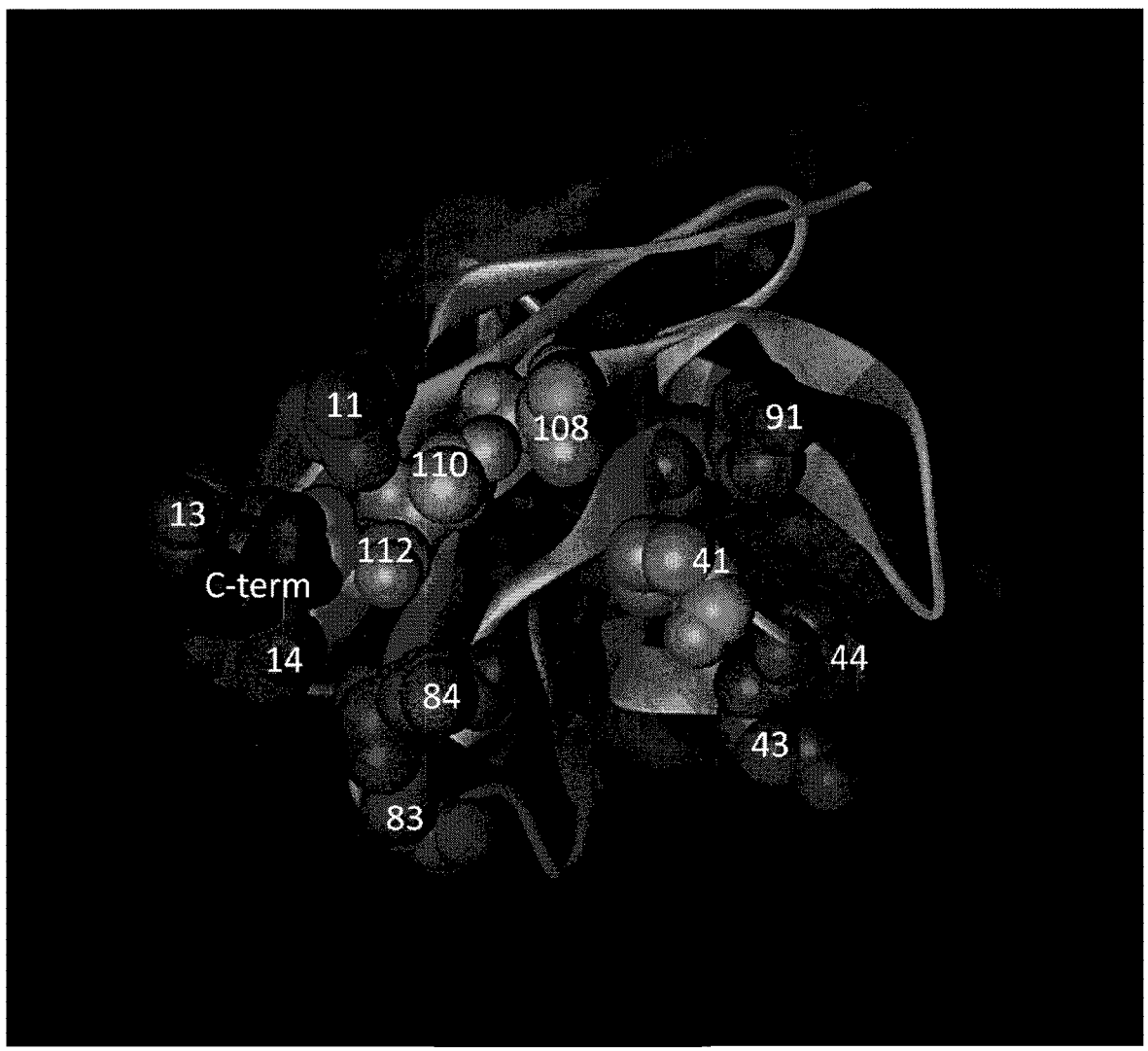
FIG. 3: shows a model crystal structure of DOM1H-131-206 with residues highlighted that impact on ADA binding when mutated. Modelling of surface residues was undertaken and the resulting mutants were screened in the ADA assay for binding to pre-existing ADAs (e.g. as described in Example 2). Residues indicated as 14 and "C term" were found to have a strong impact on ADA binding when mutated, residues indicated as 112, 110, 108 and 41 were found to have a moderate impact on ADA binding when mutated and residues indicated as 13, 11, 91, 43, 44, 83 and 84 were found to have a weak impact on ADA binding when mutated.

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al, Molecular Cloning: A Laboratory Manual, 2d ed. (1989) Cold Spring Harbor Laboratory Press, Cold Spring Harbor, N.Y. and Ausubel et al, Short Protocols in Molecular Biology (1999) $4^{th}$ Ed, John Wiley & Sons, Inc. which are incorporated herein by reference) and chemical methods.

Affinity is the strength of binding of one molecule, e.g. an antigen binding protein of the invention, to another, e.g. its target antigen, at a single binding site. The binding affinity of an antigen binding protein to its target may be determined by standard equilibrium methods (e.g. enzyme-linked immunoabsorbent assay (ELISA) or radioimmunoassay (RIA)), or kinetics (e.g. BIACORE™ analysis).

The term "epitope" as used herein refers to that portion of the antigen that makes contact with a particular binding domain of the antigen binding protein e.g. dAb. An epitope may be linear or conformational/discontinuous. A conformational or discontinuous epitope comprises amino acid residues that are separated by other sequences, i.e. not in a continuous sequence in the antigen's primary sequence. Although the residues may be from different regions of the peptide chain, they are in close proximity in the three dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography.

A dAb conjugate refers to a composition comprising a dAb to which a further molecule is chemically conjugated by means of a covalent or noncovalent linkage, preferably a covalent linkage. Such covalent linkage could be through a peptide bond or other means such as via a modified side chain. The noncovalent bonding may be direct (e.g., electrostatic interaction, hydrophobic interaction) or indirect (e.g., through noncovalent binding of complementary binding partners (e.g., biotin and avidin), wherein one partner is covalently bonded to drug and the complementary binding partner is covalently bonded to the dAb™). When complementary binding partners are employed, one of the binding partners can be covalently bonded to the drug directly or through a suitable linker moiety, and the complementary binding partner can be covalently bonded to the dAb™ directly or through a suitable linker moiety.

As used herein, a dAb fusion refers to a fusion protein that comprises a dAb and a polypeptide drug. The dAb and the polypeptide drug are present as discrete parts (moieties) of a single continuous polypeptide chain.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide.

As used herein, the term mAbdAb refers to a monoclonal antibody linked to a further binding domain, in particular a single variable domain such as a domain antibody. A mAbdAb has at least two antigen binding sites, at least one of which is from a domain antibody, and at least one is from a paired VH/VL domain. Such mAbdAbs are described for example in WO 2009/068649.

As used herein, "peptide" refers to about two to about 50 amino acids that are joined together via peptide bonds. As used herein, "polypeptide" or "protein" refers to at least about 50 amino acids that are joined together by peptide bonds. Polypeptides and proteins generally comprise tertiary structure and fold into functional domains.

As used herein, the term "single chain Fc region of an antibody" refers to a single heavy chain Fc region of an IgG, such as an IgG1, IgG2, IgG3, iGG4 or IgG4PE, or an IgA antibody. A single heavy chain Fc region may comprise one or more of the CH1, CH2 and CH3 constant region antibody domains, for example all three constant region antibody domains or just the CH2 and CH3 domains. In addition to comprising one or more of the CH1, CH2 and CH3 constant region antibody domains, the single heavy chain FC region of an antibody may further comprise a hinge region of an antibody (such a region normally found between the CH1 and CH2 domains).

As used herein, "functional" describes a polypeptide or peptide that has biological activity, such as specific binding activity. For example, the term "functional polypeptide" includes an antibody or antigen-binding fragment thereof that binds a target antigen through its antigen-binding site.

As used herein, "target ligand" refers to a ligand which is specifically or selectively bound by a polypeptide or peptide. For example, when a polypeptide is an antibody, antigen-binding fragment thereof, or immunoglobulin single variable domain, the target ligand can be any desired antigen or epitope. Binding to the target antigen is dependent upon the polypeptide or peptide being functional.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

The phrase "immunoglobulin single variable domain" refers to an antibody variable domain (VH, VHH, VL) that specifically binds an antigen or epitope independently of other V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. The VHH may be humanized. Also within the scope of the present invention are human dAbs which have been modified so as to be not fully human, for example modifications which are made to reduce aggregation, including mutation of the same residues which are Camelid motifs.

An unmodified immunoglobulin single variable domain (i.e. unmodified dAb), for example a dAb that binds a target, comprises three complementarity determining regions (CDRs) within a framework structure. Whereas in the genetics of naturally occurring immunoglobulin chains the V region terminates at the beginning of CDR3, with the remainder of CDR3 being provided by the D and 3 regions (resulting in a V-D-J fusion), for the purposes of the present invention a dAb includes all of CDR3 and terminates in framework 4 residue at its C-terminus. A VH dAb terminates in residues LVTVSS at its C-terminus. A VHH dAb terminates in residues VTVSS at its C-terminus. A VL dab terminates in VEIKR at its C terminus.

A "modified dAb" is a dAb as described herein which additionally has a modification which alters the three dimensional conformation of the dAb C-terminus. A modified dAb includes a dAb which comprises C-terminal additions, extensions or tags and/or certain amino acid substitutions as disclosed herein.

The present invention also provides a single immunoglobulin variable domain (or a molecules comprising a dAb e.g. a mAbdAB) as described above which has a lower binding affinity and/or avidity (e.g. which has a KD of binding to ADA which is 150% or more (e.g. 200%, 250%, 300%, 350%, 400%, 450%, 500%, 550%, 600%, 650% or more of the KD of an equivalent sequence) for an anti-drug antibody than an equivalent dAb (or molecule comprising the dAb) which equivalent dAb has the same sequence except that X is absent, $_n$, $_p$ and $_q$ are 1 and there are no framework mutations. By this is meant that a dAb, for example DOM 1H-131-206 (SEQ ID NO 1) when then modified such that it is extended to contain X, for example a C-terminal single alanine extension, or is modified to remove the C terminal serine, or is modified by a substitution in the framework of one or more of residues 14, 41, 108, 110 and/or 112 (or any combination of such modifications) binds to an anti-drug antibody (ADA) with a lower binding affinity and/or avidity than DOM 1H-131-206 (SEQ ID NO 1) without any such modifications. This may be determined using surface Plasmon resonance e.g. on a Biacore™ using standard techniques. The skilled person will understand that the lower the KD value the stronger the binding.

Also provided by the invention is dAb modified as described herein to have reduced ADA binding and which has reduced binding to ADAs as determined using a confirmation assay as described in Example 2 and where said modified dAb has a mean % inhibition of signal which is less than 90%, e.g. less than 80%, e.g. less than 70%, e.g. less than 60%, e.g. less than 50%, e.g. less than 40%, e.g. less than 30%, e.g. less than 20%, e.g. less than 10%, in comparison with a control dAb which has around 98%-100% inhibition of signal, said control (unmodified) dAb has the same or similar sequence but is not modified to reduce ADA binding.

A pre-existing ADA is an ADA already present in the subject to which the drug is to be administered. A pre-existing ADA may be present in a naive subject (i.e. a subject to which the drug has never been administered before).

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

As used herein, the term "dose" refers to the quantity of fusion or conjugate administered to a subject all at one time (unit dose), or in two or more administrations over a defined time interval. For example, dose can refer to the quantity of fusion or conjugate administered to a subject over the course of one day (24 hours) (daily dose), two days, one week, two weeks, three weeks or one or more months (e.g., by a single administration, or by two or more administrations). The interval between doses can be any desired amount of time.

"Monovalent" means binding to one epitope.

The phrase, "half-life," refers to the time taken for the serum or plasma concentration of the fusion or conjugate to reduce by 50%, in vivo, for example due to degradation and/or clearance or sequestration by natural mechanisms. The compositions of the invention are stabilized in vivo and their half-life increased by binding to serum albumin molecules e.g. human serum albumin (HSA) which resist degradation and/or clearance or sequestration. These serum albumin molecules are naturally occurring proteins which themselves have a long half-life in vivo. The half-life of a molecule is increased if its functional activity persists, in vivo, for a longer period than a similar molecule which is not specific for the half-life increasing molecule.

As used herein, "hydrodynamic size" refers to the apparent size of a molecule (e.g., a protein molecule, ligand) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

Calculations of "homology" or "identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes is at least 30%, or at least 40%, or at least 50%, or at least 60%, or at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences. Amino acid and nucleotide sequence alignments and homology, similarity or identity, as defined herein may be prepared and determined using the algorithm BLAST 2 Sequences, using default parameters (Tatusova, T. A. et al., *FEMS Microbiol Lett,* 174:187-188 (1999).

The invention relates to isolated and/or recombinant nucleic acids encoding the compositions of the invention that are described herein.

Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a vector (e.g., a plasmid).

Nucleic acids referred to herein as "recombinant" are nucleic adds which have been produced by recombinant DNA methodology, including methods which rely upon artificial recombination, such as cloning into a vector or chromosome using, for example, restriction enzymes, homologous recombination, viruses and the like, and nucleic acids prepared using the polymerase chain reaction (PCR).

The invention also relates to a recombinant host cell e.g. mammalian or microbial, which comprises a (one or more) recombinant nucleic acid or expression construct comprising nucleic acid(s) encoding a composition of the invention as described herein, e.g. a dAb modified to reduce binding to ADAs. There is also provided a method of preparing a composition of the invention as described herein, comprising maintaining a recombinant host cell e.g. mammalian or microbial, of the invention under conditions appropriate for expression of the fusion polypeptide. The method can further comprise the step of isolating or recovering the fusion, if desired.

For example, a nucleic acid molecule (i.e., one or more nucleic acid molecules) encoding a molecule of the invention can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable animal, in suitable culture media supplemented with appropriate salts, growth factors, antibiotics, nutritional supplements, etc.), whereby the encoded peptide or polypeptide is produced. If desired, the encoded peptide or polypeptide can be isolated or recovered (e.g., from the animal, the host cell, medium, milk). This process encompasses expression in a host cell of a transgenic animal (see, e.g., WO 92/03918, GenPharm International).

The molecules of the invention as described herein can also be produced in a suitable in vitro expression system, e.g. by chemical synthesis or by any other suitable method.

As described and exemplified herein, molecules of the invention, generally bind to their target ligands with high affinity.

The molecules of the invention e.g. modified dAbs with reduced binding to ADAs, can be expressed in *E. coli* or in *Pichia* species (e.g., *P. pastoris*). In one embodiment, the dAb is secreted in *E. coli* or in *Pichia* species (e.g., *P. pastoris*); or in mammalian cell culture (e.g. CHO, or HEK 293 cells). Although, the molecules described herein can be secretable when expressed in *E. coli* or in *Pichia* species or mammalian cells they can be produced using any suitable method, such as synthetic chemical methods or biological production methods that do not employ *E. coli* or *Pichia* species. In an embodiment nucleic acid encoding the dAbs of the invention e.g. the TNFR1 dAbs described herein, can be cloned into a suitable expression vector e.g. Pave011 (from Fujifilm Diosynth) and then expressed in a microbial vector such as *E. coli*.

In one embodiment the invention the dAb e.g. the VH, VL or VHH, can be modified to prevent binding to ADAs such that the modification comprises a tag present at the C terminus. This tag can be present as a fusion or conjugate with the molecule. The tag can be any tag known in the art for example affinity tags such as myc-tags, FLAG tags, his-tags, chemical modification such as PEG, or protein domains such as the antibody Fc domain. In particular, the present invention provides a molecule of the invention extended with a tag, a chemical modification or a protein domain for use in a method of reducing side effects as further defined herein.

In another embodiment the invention also provides a molecule e.g. dAb (such as a VH or VL or a VHH) which comprises a modified framework which reduces pre-existing ADA binding for example a dAb (such as a VHH, VH or VL) which comprises an amino acid substitution at any one of positions 14, 41, 108, 110, or 112. For example these substitutions can be one or more modifications selected from: P14A, P14K, P14Q, P14T, P41A, L108A, L108 Q, T110A and S112A.

In one aspect of this embodiment the dAb (e.g. the VHH, VH or VL) comprises one or more modifications selected from: P14A, P14K, P14Q, P14T, P41A, L108A, T110A and S112A; and can further comprise any of the C terminal extensions, additions, deletion or tags as described above. In one embodiment the dAb (e.g. the VHH, VH or VL) which comprises one or more modifications selected from: P14A, P14K, P14Q, P14T P41A, L108A, T110A and S112A also comprises an amino acid extension at the C terminus of the dAb which is selected from: (a) alanine, or (b) an amino acid sequence comprising or consisting of an extension selected from: AS, AST, ASTK, ASTKG, or ASTKGP. Additionally, the dAb molecules described herein and pharmaceutical compositions comprising these molecules may be useful in the prevention or reduction of side effects. The binding of anti-drug antibodies by a dAb may lead to two dAbs being brought together. In some circumstances, this may lead to safety concerns. For example, if the target of a dAb is a receptor or a polymeric target, the bringing together of two dAbs may bring two targets together. This may lead to unexpected pharmacological impacts, for example agonism rather than antagonism e.g. via dimerisation of the receptor. Thus the present invention provides the use of the molecules of the invention in a method of preventing side effects. By prevention is meant that the use of the molecules of the invention abrogates to a complete or partial level binding of pre-existing anti drug antibodies as compared to the equivalent molecule which has not been modified. The reduction in binding of ADAs leads to a reduction in the level of unwanted pharmacological effects. Thus the molecules of the invention can have an enhanced safety profile and fewer side effects than the unmodified molecules e.g. unmodified dAbs, which do not comprise a C terminal extension, addition, deletion or tag and/or other framework modification, to reduce pre-existing ADA binding. Similarly, administration of the modified molecules described herein or of pharmaceutical compositions comprising these modified molecules (which have reduced ability to bind to pre-existing ADA) can lead to modified immunogenicity, this is because when the unmodified molecules bind to ADAs they form immune complexes and such immune complexes could then generate an immune response. In addition administration of the modified molecules described herein or of pharmaceutical compositions comprising these modified molecules can also result in improved efficacy and an improved safety profile and e.g. can be advantageously used for repeat dosing to patients who could develop autoantibodies to the unmodified molecules. In addition, the dAb molecules of the invention are able to be administered to a patient population without the need for pre-screening for ADA titres to remove subjects at risk of an adverse reaction.

In the context of the use of molecules for the prevention of side effects, the present invention provides also for the use of a single immunoglobulin variable domain as defined herein in which X is replaced by Y, wherein Y is selected from the group consisting of: a tag such as an affinity tag, a myc tag, a FLAG tag or a his-tag, a chemical modification such as a PEG group, or a protein, such as the Fc portion of an antibody.

The present invention also provides a method of preventing or reducing side effects in treatment regimen by administration of the molecules of the invention, or molecules of the invention in which X has been replaced by Y as defined above. Also provided is a method of modifying a molecule as described herein to reduce its binding to ADAs and to reduce side effects.

The invention also provides compositions which comprise the modified molecules as described herein e.g. compositions comprising modified VHH, VH or VL. Such compositions can comprise the modified molecules present as a fusion or conjugate with other molecules e.g. other proteins, antibody molecules or antibody fragments. For example a dAb can be present as a formatted dAb (e.g. the dAb can be present as a dAb-fc fusion or conjugate as described in for example WO 2008/149148) or it can be present as a mAbdAb (as described in WO 2009/068649) or the dAb be present as a fusion or conjugate with half life extending proteins or polypeptides e.g., a further dAb e.g., a dAb which binds to serum albumin (AlbudAb™) or e.g., with polyethyleneglygol PEG or further therapeutic or active molecules. In this embodiment the therapeutic molecule(s) when present as a fusion or conjugate with a dAb (e.g. a VHH, VH or VL) can be linked to either the C-terminal extension of the dAb or the N-terminus of the dAb. In one embodiment one or more therapeutic molecules are present as a fusion (or conjugate) at the N terminus of the dAb.

In one embodiment, the dAbs of the invention (and also molecules comprising dAbs such as mAbdAbs which are also part of the invention) which have reduced ability to bind ADAs bind to a target ligand with high affinity, for example they can have a KD as measured by surface plasmon resonance using Biacore™ in the region of 5 micromolar to about 1 pM, e.g. about 500 nM to about 10 pM e.g. about 200 nM to about 10 pM, e.g. 50 nM to about 10 pM e.g. about 10 nm to about 10 pM. In an embodiment the molecule can have a KD of about 10 nM to about 10-30 pM e.g. it can be a TNFR1 dAb with reduced binding to ADAs and which has a KD of about 10-30 pM e.g. about 20 pM.

In an embodiment the dAbs of the invention (and also molecules comprising dAbs such as mAbdAbs which are also part of the invention) which have reduced ability to bind ADAs can have expression levels which are at least 3%, e.g. 5%, 10%, 20%, 30%, 40%, 50%, 60%, 70%, 80%, 90%, 100% of those shown by a dAb of the same or similar amino acid sequence which is not modified as described herein to reduce binding to ADAs. In a further embodiment the molecules of the invention (e.g. dAbs and molecules comprising dAbs such as mAbdAbs) which have reduced ability to bind ADAs can have expression levels of at least 0.1 g/Liter.

In an embodiment the dAbs of the invention (and also molecules comprising dAbs such as mAbdAbs which are also part of the invention) which have reduced ability to bind ADAs have a KD of binding to their target antigen which is about 50 fold higher (or more) (i.e. the dAbs are 50 fold less potent), e.g. at about 40 fold higher, about 30 fold higher, about 20 fold higher, about 10 fold higher, about 5 fold higher, about 4 fold higher than the KD of a dAb of the same or similar amino acid sequence which is not modified as described herein to reduce binding to ADAs. In an embodiment the dAbs of the invention (and also molecules comprising dAbs such as mAbdAbs which are also part of the invention) which have reduced ability to bind ADAs have a KD to their target antigen which is essentially the same (e.g. around 2 fold higher to 2 fold lower) or more than 2 fold lower than the KD of a dAb of the same or similar amino acid sequence which is not modified as described herein to reduce binding to ADAs.

The invention further relates to uses, formulations, compositions comprising such C terminally extended and/or modified molecules and also to methods of production and expression of these molecules.

In an embodiment the invention provides a dAb (VH, VL, or VHH) which has any of the C terminal modifications as described above and which binds to a target selected from: TNFα, TNFR1, VEGF, IL-1R, IL-6R, IL-4, IL-5, IL-13, DC-SIGN, ASGPR, albumin, and TGFβR2.

In one embodiment the invention provides a dAb which is described or disclosed in any one of: WO 2007/049017 (e.g. the anti-TNFR1 dAb designated 2H-131-511 or a dAb which is at least 80% identical to this (e.g. 85%, 90%, 95%, 96%, 97%, 98%, 99%, 100% identical), WO 2008/149144 (e.g. an anti-TNFR1 dAb selected from: 1h-131-201, 1h-131-202, 1h-131-203, 1h-131-204, 1h-131-205 or a dAb which is at least 80% identical to this (e.g. 85%, 90%, 95%, 96%, 97%, 98%, 99%, 100% identical) and WO 2008/149148 (the contents of which are explicitly incorporated herein by reference) e.g. any one of the anti-TNFR1 dAbs therein; and which dAb further comprises at least one of the modifications described herein to reduce binding affinity and/or avidity to ADAs e.g. any one of the C terminal modifications as described above and/or any one of the amino acid substitutions and/or deletions as described above.

In another embodiment the invention provides an unmodified dAb which is described or disclosed in any one of WO 2007/049017, WO 2008/149144, and WO 2008/149148 (e.g. any one of the dAb sequences described above), and which dAb is then modified to comprises one or more framework modifications e.g. selected from: P14A, P14K, P14Q, P14T P41A, L108A, T110A and S112A framework mutations and which can also further optionally comprise any of the C terminal modifications described herein. In one example the unmodified dAb can be any one of the anti-TNFR1dAb sequences described or disclosed in any one of WO 2007/049017, WO 2008/149144, and WO 2008/149148. In an embodiment the unmodified anti-TNFR1 dAb sequence can be one which is at least 80% (e.g. 85%, 90%, 95%, 96%, 97%, 98%, 99%, 100%) identical to the dAb sequence identified as either DOM1h-131-206 (disclosed in WO 2008/149148), DOM 1h-131-511 (disclosed in WO 2007/049017 and 2008/149144) and DOM 1h-131-202 (disclosed in WO 2008/149144).

In another embodiment the invention provides a VEGF dAb which is described or disclosed in WO 2008/149147 e.g. the dAb designated 15-26-593 (amino acid sequence shown in FIG. 5 of WO 2008/149147), (the contents of which are explicitly incorporated herein by reference), and which dAb further comprises any one of the modifications described herein to reduce binding affinity and/or avidity to ADAs e.g. any one of the C terminal modifications as described above and/or any one of the amino acid substitutions and/or deletions as described above. Unmodified dAb amino acid sequences are as follows:

(a) DOM 1H-131-206
(SEQ ID NO 1)
EVQLLESGGGLVQPGGSLRLSCAASGFTFAHETMVWVRQAPGKGLEWVSH

IPPDGQDPFYADSVKGRFTISRDNSKNTLYLQMNSLRAEDTAVYHCALLP

KRGPWFDYWGQGTLVTVSS (b) DOM 1H-131-511
(SEQ ID NO 2)
EVQLLESGGGLVQPGGSLRLSCAASGFTFAHETMVWVRQAPGKGLEWVSH

IPPVGQDPFYADSVKGRFTISRDNSKNTLYLQMNSLRAEDTAVYYCALLP

KRGPWFDYWGQGTLVTVSS (c) DOM 1H-131-202
(SEQ ID NO 3)
EVQLLESGGGLVQPGGSLRLSCAASGFTFAHETMVWVRQAPGKGLEWVSH

IPPDGQDPFYADSVKGRFTISRDNSKNTLYLQMNSLRAEDTAVYYCALLP

KRGPWFDYWGQGTLVTVSS (d) VHH clone 2(d):
(SEQ ID NO 4)
EVQLVESGGGLVQPGGSLRLSCAASGSVFKINVMAWYRQAPGKGRELVAG

IISGGSTSYADSVKGRFTISRDNAKNTLYLQMNSLRPEDTAVYYCAFITT

ESDYDLGRRYWGQGTLVTVSSGGGGSGGGSEVQLVESGGGLVQPGNSLRL

SCAASGFTFSSFGMSWVRQAPGKGLEWVSSISGSGSDTLYADSVKGRFTI

SRDNAKTTLYLQMNSLRPEDTAVYYCTIGGSLSRSSQGTLVTVSS (e) VHH clone 2(e):
(SEQ ID NO 5)
EVQLVESGGGLVQPGGSLRLSCAASGFTFSDYWMYWVRQAPGKGLEWVSE

INTNGLITKYPDSVKGRFTISRDNAKNTLYLQMNSLRPEDTAVYYCARSP

SGFNRGQGTLVTVSSGGGGSGGGSEVQLVESGGGLVQPGNSLRLSCAASG

FTFSSFGMSWVRQAPGKGLEWVSSISGSGSDTLYADSVKGRFTISRDNAK

TTLYLQMNSLRPEDTAVYYCTIGGSLSRSSQGTLVTVSSGGGGSGGGSEV

QLVESGGGLVQPGGSLRLSCAASGFTFSDYWMYWVRQAPGKGLEWVSEIN

TNGLITIMDSVKGRFTISRDNAKNTLYLQMNSLRPEDTAVYYCARSPSGF

NRGQGTLVTVSS (f) VHH clone 2(f)
(SEQ ID NO 6)
EVQLVESGGGLVQPGGSLRLSCAASGRTFSYNPMGWFRQAPGKGRELVAA

ISRTGGSTYYPDSVEGRFTISRDNAKRMVYLQMNSLRAEDTAVYYCAAAG

VRAEDGRVRTLPSEYTFWGQGTQVTVSSAAAEVQLVESGGGLVQPGGSLR

LSCAASGRTFSYNPMGWFRQAPGKGRELVAAISRTGGSTYYPDSVEGRFT

ISRDNAKRMVYLQMNSLRAEDTAVYYCAAAGVRAEDGRVRTLPSEYTFWG

QGTQVTVSS

In another embodiment the invention provides a modified VHH dAb selected from the following sequences:

(a) VHH clone 2(d) + A:
(SEQ ID NO 7)
EVQLVESGGGLVQPGGSLRLSCAASGSVFKINVMAWYRQAPGKGRELVAG

IISGGSTSYADSVKGRFTISRDNAKNTLYLQMNSLRPEDTAVYYCAFITT

ESDYDLGRRYWGQGTLVIVSSGGGGSGGGSEVQLVESGGGLVQPGNSLRL

SCAASGFTFSSFGMSWVRQAPGKGLEVVVSSISGSGSDTLYADSVKGRFT

ISRDNAKTTLYLQMNSLRPEDTAVYYCTIGGSLSRSSQGTLVTVSSA (b) VHH clone 2(e) + A:
(SEQ ID NO 8)
EVQLVESGGGLVQPGGSLRLSCAASGFTFSDYWMYWVRQAPGKGLEVVVS

EINTNGLITKYPDSVKGRFTISRDNAKNTLYLQMNSLRPEDTAVYYCARS

PSGFNRGQGTLVTVSSGGGGSGGGSEVQLVESGGGLVQPGNSLRLSCAAS

GFTFSSFGMSVVVRQAPGKGLEVVVSSISGSGSDTLYADSVKGRFTISRD

NAKTTLYLQMNSLRPEDTAVYYCTIGGSLSRSSQGTLVTVSSGGGGSGGG

SEVQLVESGGGLVQPGGSLRLSCAASGFIFSDYWMYWVRQAPGKGLEVVV

SEININGLITKYPDSVKGRFTISRDNAKNTLYLQMNSLRPEDTAVYYCAR

SPSGFNRGQGTLVTVSSA (c) VHH clone 2(f) + A
(SEQ ID NO 9)
EVQLVESGGGLVQPGGSLRLSCAASGRTFSYNPMGWFRQAPGKGRELVAA

ISRTGGSTYYPDSVEGRFTISRDNAKRMVYLQMNSLRAEDTAVYYCAAAG

VRAEDGRVRTLPSEYTFWGQGTQVTVSSAAAEVQLVESGGGLVQPGGSLR

LSCAASGRTFSYNPMGWFRQAPGKGRELVAAISRTGGSTYYPDSVEGRFT

ISRDNAKRMVYLQMNSLRAEDTAVYYCAAAGVRAEDGRVRTLPSEYTFWG

QGTQVTVSSA

In another embodiment the invention provides a modified DOM1h-131-206 dAb which binds to TNFR1 and which is selected from the following amino acid sequences:

(a) DOM1h-131-206 dAb with an extension of a single alanine at the C terminus:
(SEQ ID NO 16)
EVQLLESGGGLVQPGGSLRLSCAASGFTFAHETMVWVRQAPGKGLEVVVSHIPPDGQDPFYADSVKGR

FTISRDNSKNTLYLQMNSLRAEDTAVYHCALLPKRGPWFDYWGQGTLVTVSSA

(b) DOM1h-131-206 dAb with an extension of a single alanine and a P14A framework mutation:
(SEQ ID NO 17)
EVQLLESGGGLVQAGGSLRLSCAASGFTFAHETMVWVRQAPGKGLEVVVSHIPPDGQDPFYADSVKGR

FTISRDNSKNTLYLQMNSLRAEDTAVYHCALLPKRGPWFDYWGQGTLVTVSSA

(c) DOM1h-131-206 dAb with a P14A framework mutation:
(SEQ ID NO 18)
EVQLLESGGGLVQAGGSLRLSCAASGFTFAHEINVWVRQAPGKGLEVVVSHIPPDGQDPFYADSVKGR

FTISRDNSKNTLYLQMNSLRAEDTAVYHCALLPKRGPWFDYWGQGTLVTVSS (d) DOM1h-131-206 dAb with an ASTKG C terminus extension
(SEQ ID NO 19)
EVQLLESGGGLVQPGGSLRLSCAASGFTFAHETMVWVRQAPGKGLEVVVSHIPPDGQDPFYADSVKGR

FTISRDNSKNTLYLQMNSLRAEDTAVYHCALLPKRGPWFDYWGQGTLVTVSSASTKG

(e) DOM1h-131-206 dAb with an ASTKG C terminus extension and a P14A framework mutation
(SEQ ID NO 20)
EVQLLESGGGLVQAGGSLRLSCAASGFTFAHETMVWVRQAPGKGLEVVVSHIPPDGQDPFYADSVKGR

FTISRDNSKNTLYLQMNSLRAEDTAVYHCALLPKRGPWFDYWGQGTLVTVSSASTKG

The invention also provides nucleic adds encoding the molecules described herein for example nucleic acids encoding the anti-TNFR1 dAbs described above. Also provided are host cells e.g. non-embryonic host cells e.g. prokaryotic or eukaryotic hosts cells such as *E. coli* or yeast host cells or mammalian cells that comprise these nucleic acids.

The invention additionally provides a dAb which has reduced binding to ADA in human sera (e.g. does not bind to pre-existing ADA in human sera) and wherein the epitope on the dAb to which the ADA binds is masked (i.e. the epitope is no longer available to bind to ADA as e.g. it has been covered or masked by another molecule so preventing binding or its steric conformation has been changed so preventing binding). The epitope on the dAb can be masked by any of the modifications described herein to reduce ADA binding, for example adding a chemical entity to the C terminus of the dAb or by framework substitutions, or deletions as described herein. The chemical entity added to the C terminus of the dAb can be an extension (e.g. an amino acid extension) or a tag or it can be a chemical modification such as pegylation or amidation. The modification to the C terminus can be one which either directly or indirectly changes the conformation of the epitope on the dAb which binds to ADAs thereby reducing the ability of the dAb to bind to ADAs.

The skilled person will appreciate that, upon production of a molecule as described herein e.g. a dAb, in particular depending on the cell line used and particular amino acid sequence of the molecule e.g. dAb, post-translational modifications may occur. For example, this may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of such molecules, e.g. dAbs, which have been subjected to, or have undergone, one or more post-translational modifications. Thus an dAb of the invention includes an a dAb which has undergone a post-translational modification such as described as follows: Glycosylation of antibodies at conserved positions in their constant regions is known to have a profound effect on antibody function, particularly effector functioning, see for example, Boyd et al. (1996) Mol. Immunol. 32: 1311-1318. Glycosylation variants of the antigen binding proteins of the invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al. (2001) Biochemistry 40: 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al. (2004) Science 303: 371: Sears et al. (2001) Science 291: 2344; Wacker et al. (2002) Science 298: 1790; Davis et al. (2002) Chem. Rev. 102: 579; Hang et al. (2001) Acc. Chem. Res 34: 727. The antibodies (for example of the IgG isotype, e.g. IgG1) as herein described may comprise a defined number (e.g. 7 or less, for example 5 or less, such as two or a single) of glycoform(s); Deamidation is an enzymatic reaction primarily converting asparagine (N) to iso-aspartic acid and aspartic acid (D) at approximately 3:1 ratio. To a much lesser degree, deamidation can occur with glutamine residues in a similar manner. Deamidation in a CDR results in a change in charge of the molecule, but typically does not result in a change in antigen binding, nor does it impact on PK/PD; Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but occasionally can occur at tryptophan and free cysteine residues; disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling; Isomerization typically occurs during production, purification, and storage (at acidic pH) and usually occurs when aspartic acid is converted to isoaspartic acid through a chemical process; N-terminal glutamine in the heavy chain and/or light chain is likely to form pyroglutamate (pGlu). Most pGlu formation happens in the production bioreactor, but it can be formed non-enzymatically, depending on pH and temperature of processing and storage conditions. pGlu formation is considered as one of the principal degradation pathways for recombinant mAbs; C-terminal lysine clipping is an enzymatic reaction catalyzed by carboxypeptidases, and is commonly observed in recombinant mAbs. Variants of this process include removal of lysine from one or both heavy chains. Lysine clipping does not appear to impact bioactivity and has no effect on mAb effector function.

The invention further provides a method for producing a molecule of the present invention comprising an amino acid extension present as a direct fusion which method comprises maintaining a host cell such as those described above that comprises a recombinant nucleic acid and/or construct that encodes a fusion of the invention under conditions suitable for expression of said recombinant nucleic acid, whereby a fusion is produced.

The invention also provides pharmaceutical compositions comprising the modified molecules of the invention. The invention further provides a pharmaceutical composition of the invention for use in medicine, e.g. for use in the treatment or prevention of e.g. disease or condition or disorder and which comprises administering to said individual a therapeutically effective amount of a pharmaceutical composition of the invention. Generally, the molecules of the invention will be utilised in purified form together with pharmacologically or physiologically appropriate carriers. Typically, these carriers can include aqueous or alcoholic/aqueous solutions, emulsions or suspensions, any including saline and/or buffered media. Parenteral vehicles can include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates. Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The invention also provides a method for treating (therapeutically or prophylactically) a patient or subject having a disease or disorder, such as those described herein, and which comprises administering to said individual a therapeutically effective amount of a pharmaceutical composition of the invention.

The pharmaceutical compositions, of the invention may be administered alone or in combination with other molecules or moieties e.g. polypeptides, therapeutic proteins and/or molecules (e.g., other proteins (including antibodies), peptides, or small molecule drugs.

The invention also provides pharmaceutical compositions of the invention comprising anti-TNFR1 VH or VL dAbs modified as described herein, for example those anti-TNFR1VH or VL dAbs described herein, or anti-TNFR1VHH domains modified as described herein, for use in the treatment of inflammatory diseases or disorders, e.g. psoriasis, arthritis, multiple sclerosis, inflammatory bowel disease (e.g.) Crohn's disease and ulcerative colitis; or for example respiratory or pulmonary diseases or disorders, e.g selected from: chronic obstructive pulmonary disease, chronic bronchitis, chronic obstructive bronchitis and emphysema, lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis and Acute lung injury (ALI) and also Acute Respiratory Distress syndrome (ARDS) and complications thereof such as Acute Kidney Injury.

The invention also provides for use of a pharmaceutical composition of the invention comprising anti-TNFR1 dAbs (VH, VL or VHH) modified as described herein, in the manufacture of a medicament for treatment of any of the specified diseases or disorders described above.

The invention also relates to use of any of the compositions described herein for use in therapy, diagnosis or prophylaxis of any of the inflammatory diseases or disorders or respiratory or pulmonary diseases or disorders as described above. The invention also relates to prophylactic use of any of the compositions described herein to prevent or alleviate any of the inflammatory diseases or disorders or respiratory or pulmonary diseases or disorders described above.

The compositions containing the anti-TNFR1 dAbs as described herein, e.g. DOM 1H-131-206 with a C-terminal alanine extension, can be administered for prophylactic and/or therapeutic treatments and are administered as a "therapeutically-effective dose". Amounts needed to achieve this dosage will depend upon the severity of the disease and the general state of the patient's own immune system, but generally range from 0.005 to 5.0 mg of dAb per kilogram of body weight, with doses of 0.05 to 2.0 mg/kg/dose being more commonly used. For prophylactic applications, similar or slightly lower dosages, to prevent, inhibit or delay onset of disease (e.g., to sustain remission or quiescence, or to prevent acute phase) may be used. The skilled clinician will be able to determine the appropriate dosing interval to treat, suppress or prevent disease. When an anti-TNFR1 dAb as described herein is administered to treat, suppress or prevent a chronic inflammatory disease, it can be administered up to four times per day, twice weekly, once weekly, once every two weeks, once a month, or once every two months, at a dose off, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the anti-TNFR1 dAb can be administered to treat, suppress or prevent a chronic inflammatory disease once every two weeks or once a month at a dose of about 10 µg/kg to about 10 mg/kg (e.g., about 10 µg/kg, about 100 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.)

Treatment or therapy performed using the compositions described herein is considered "effective" if one or more symptoms or signs are reduced or alleviated (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the precise nature of the disease or disorder targeted, but can be measured by an ordinarily skilled clinician or technician.

Similarly, prophylaxis performed using a composition as described herein is "effective" if the onset or severity of one or more symptoms or signs is delayed, reduced or abolished relative to such symptoms in a similar individual (human or animal model) not treated with the composition.

The molecules of the invention can be further formatted to have a larger hydrodynamic size to further extend the half life, for example, by attachment of a PEG group, serum albumin, transferrin, transferrin receptor or at least the transferrin-binding portion thereof, an antibody Fc region, or by conjugation to an antibody domain. For example, the dAb that binds serum albumin can be formatted as a larger antigen-binding fragment of an antibody (e.g., formatted as a Fab, Fab', F(ab)$_2$, F(ab')$_2$, IgG, scFv).

In certain embodiments, the invention provides a composition according to the invention that comprises a dual-specific ligand or multi-specific ligand that comprises a first dAb which is modified according to the invention e.g. by a C terminal extension and/or by a P14A framework mutation and a second dAb that has the same or a different binding specificity from the first dAb and optionally in the case of multi-specific ligands further dAbs. The second dAb (or further dAbs) may optionally bind a different target and may optionally also comprise a C terminal extension and/or a P14A framework mutation according to the invention.

In one aspect, the invention provides the molecules and compositions of the invention for delivery by parenteral administration e.g. by subcutaneous, intramuscular or intravenous injection, inhalation, nasal delivery, transmucossal delivery, oral delivery, delivery to the GI tract of a patient, rectal delivery or ocular delivery. In one aspect, the invention provides the use of the molecules and compositions of the invention in the manufacture of a medicament for delivery by subcutaneous injection, inhalation, intravenous delivery, nasal delivery, transmucossal delivery, oral delivery, delivery to the GI tract of a patient, rectal delivery, transdermal or ocular delivery.

In one aspect, the invention provides a method for delivery to a patient by subcutaneous injection, pulmonary delivery, intravenous delivery, nasal delivery, transmucossal delivery, oral delivery, delivery to the GI tract of a patient, rectal or ocular delivery, wherein the method comprises administering to the patient a pharmaceutically effective amount of a molecule of the invention.

In one aspect, the invention provides an oral, injectable, inhalable, nebulisable formulation comprising a molecule of the invention.

The formulation can be in the form of a tablet, pill, capsule, liquid or syrup.

The term "subject" or "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

The invention also provides a kit for use in administering molecules and compositions according to the invention to a subject (e.g., human patient), comprising a molecule or composition of the invention, a drug delivery device and, optionally, instructions for use. The composition can be provided as a formulation, such as a freeze dried formulation or a slow release formulation. In certain embodiments, the drug delivery device is selected from the group consisting of a syringe, an inhaler, an intranasal or ocular administration device (e.g., a mister, eye or nose dropper), and a needleless injection device.

The molecules and compositions of this invention can be lyophilized for storage and reconstituted in a suitable carrier prior to use. Any suitable lyophilization method (e.g., spray drying, cake drying) and/or reconstitution techniques can be employed. It will be appreciated by those skilled in the art that lyophilisation and reconstitution can lead to varying degrees of antibody activity loss and that use levels may have to be adjusted to compensate. In a particular embodiment, the invention provides a composition comprising a lyophilized (freeze dried) composition as described herein. Preferably, the lyophilized (freeze dried) composition loses no more than about 20%, or no more than about 25%, or no more than about 30%, or no more than about 35%, or no more than about 40%, or no more than about 45%, or no more than about 50% of its activity (e.g., binding activity for serum albumin) when rehydrated. Activity is the amount of composition required to produce the effect of the composition before it was lyophilized. The activity of the composition can be determined using any suitable method before lyophilization, and the activity can be determined using the same method after rehydration to determine amount of lost activity.

The invention also provides sustained or slow release formulations comprising the molecules of the invention, such sustained release formulations can comprise the molecules of the invention in combination with, e.g. hyaluronic acid, microspheres or liposomes and other pharmaceutically or pharmacalogically acceptable carriers, excipients and/or diluents.

In one aspect, the invention provides a pharmaceutical composition comprising a molecule of the invention, and a pharmaceutically or physiologically acceptable carrier, excipient or diluent.

In one embodiment the invention provides the modified TNFR1 dAbs of the present invention which have reduced binding to ADAs e.g. such as a modified DOM1h-131-206 dAb with a modification as described herein to reduce binding to ADAs. For example the invention provides the DOM1h-131-206 dAb with an extension of a single alanine at the C-terminus (SEQ ID NO 16) e.g. as a pharmaceutical composition e.g. for use to treat a disease or disorder, for example to treat a respiratory disease or disorder such as COPD, ALI or ARDS. The DOM1h-131-206 dAb with an extension of a single alanine at the C terminus (SEQ ID NO 16) (or pharmaceutical composition comprising the DOM1h-131-206 dAb with an extension of a single alanine at the C terminus) when used to treat a respiratory disease or disorder such as COPD, AU or ARDS can be administered to a subject, e.g. to a human subject, by injection (e.g. by subcutaneous, intravenous or intramuscular injection) or it alternatively it can be given to the subject, e.g. to a human subject, by pulmonary administration e.g. by nebulisation using a standard nebuliser or by inhalation for example by using a standard inhaler device. The invention further provides sustained release and/or freeze dried formulations comprising the modified TNFR1 dAbs of the present invention with reduced ADA binding, such as the DOM1h-131-206 dAb with an extension of a single alanine at the C-terminus (SEQ ID NO 16). Also provided is a delivery device e.g. an inhaler or a nebuliser device which comprises the modified TNFR1 dAbs of the present invention, such as DOM1h-131-206 dAb with an extension of a single alanine at the C-terminus nucleic acid (SEQ ID NO 22).

In an aspect the invention provides the unmodified DOM1h-131-206 dAb (SEQ ID NO 1) or the DOM1h-131-206 dAb modified in any of the ways described herein to reduce ADA binding e.g. the DOM1h-131-206 dAb with an extension of a single alanine at the C-terminus (SEQ ID NO 16), to treat an inflammatory skin disorder e.g. psoriasis and also provided is any one of the dosage regimens as described below for use of a domain antibody in the treatment of psoriasis. The domain antibody useful for the treatment of psoriasis selectively targets the same domain of human TNFR1 as the natural, human TNF-alpha ligand for this receptor and is a specific, competitive antagonist of TNFR1, but not of TNFR2, and prevents the binding of TNF-alpha to TNFR1 and the signaling of this ligand through TNFR1. Such a domain antibody may comprise any anti-TNFR1 dAb which has been modified to reduce binding to ADAs as disclosed herein. In particular, the domain antibody may be a human domain antibody such as DOM1h-131-206 having the amino acid sequence shown in SEQ ID NO: 1, the DOM1h-131-206 with an C terminal alanine having the amino acid sequences shown in SEQ ID NO: 16, or a DOM1h-131-206 dAb (SEQ ID NO 1) which has then been modified to reduce ADA binding as described herein (i.e. any modification to reduce binding to ADAs) as disclosed herein. The domain antibody may be provided in a vial containing e.g. 100 mg or e.g. 40 mg of a lyophilizate of the domain antibody. The lyophilizate may comprise sucrose, glycine, sodium dihydrogen phosphate and polysorbate 80. This domain antibody lyophilizate can initially be reconstituted in 5 mL of sterile water and then diluted with sterile water, or another pharmaceutically acceptable diluents, to make pharmaceutical compositions comprising 20 mg/mL, 5 mg/mL, and 1 mg/mL of the domain antibody.

The domain antibody may be used to treat human patients identified as having psoriasis. In particular, the domain antibody may be used to treat human patients identified as having chronic mild, moderate, or severe, stable plaque type psoriasis with one or two plaque areas. According to the National Psoriasis Foundation, mild plaque type psoriasis affects less than 3% of a human patient's body surface area, moderate plaque type psoriasis affects between 3% and 10% of a human patient's body surface area and severe psoriasis affects more than 10 percent of a human patient's body surface area. See e.g., Krajacic, 6 (5) Supplement 6, Biotechnology Healthcare, December 2009 and National Psoriasis Foundation, About Psoriasis: Statistics. As a point of reference, a human patient's palm would be considered approximately 1% of the patient's body surface area. The severity of psoriasis can also be determined, as an alternative, according to the Psoriasis Area and Severity Index through the use of the grading system described by Fredrikson which is based on four criteria: redness, thickness, scaliness and the amount of surface area involvement. See e.g., Fredrickson, 157 Dermatologica 238 (1978). The psoriatic plaques to be treated may have a comparable infiltrate thickness of at least 200 µm, as assessed by sonographic measurements, when the domain antibody is first administered. The human patients may be male or female subjects having chronic plaque type psoriasis with stable plaque(s) on the upper extremities, thighs or trunk. These human patients may be from about 18 to about 70 years old. Human patients may also be from 14 to 26 years old as well as 14 or more years old.

The domain antibody can be administered to these human patients by injection into a psoriatic plaque. In particular, 100 µL of a pharmaceutical composition comprising 20 mg/mL, 5 mg/mL, or 1 mg/mL of the domain antibody can be administered by injection into a psoriatic plaque at a depth which targets the epidermis and superficial dermis in the plaque.

The domain antibody can be administered to a human patient with a psoriatic plaque according to a treatment protocol in which 100 µL of a pharmaceutical composition comprising 5 mg/mL of the domain antibody is injected into a psoriatic plaque once a week during a 28 day treatment period. In such a treatment protocol the patient will be administered the pharmaceutical composition four times and will receive 0.5 mg of the domain antibody during each administration such that a total dose of 2 mg of the domain antibody is received during the 28 day treatment period. This means, for example, that in a treatment protocol spanning 28 days the patient would receive the first 100 µL injection containing 0.5 mg of the domain antibody on day one, the second such injection on day eight, the third such injection on day fifteen, and the fourth such injection on day twenty-two. Domain antibody doses (e.g., 100 µL injection containing 0.5 mg of the domain antibody) in this treatment protocol are administered on a mg per patient basis.

The domain antibody can also be administered to a human patient with a psoriatic plaque according to a treatment protocol in which 100 µL of a pharmaceutical composition comprising 20 mg/mL of the domain antibody is injected into a psoriatic plaque once a week during a 28 day treatment period. In such a treatment protocol the patient will be administered the pharmaceutical composition four times and will receive 2 mg of the domain antibody during each administration such that a total dose of 8 mg of the domain antibody is received during the 28 day treatment period. This means, for example, that in a treatment protocol spanning 28 days the patient would receive the first 100 µL injection containing 2 mg of the domain antibody on day one, the second such injection on day eight, the third such injection on day fifteen, and the fourth such injection on day twenty-two. Domain antibody doses (e.g., 100 µL injection containing 2 mg of the domain antibody) in this treatment protocol are administered on a mg per patient basis.

The domain antibody can also be administered to a human patient with a psoriatic plaque according to a treatment protocol in which 100 µL of a pharmaceutical composition comprising 5 mg/mL of the domain antibody is injected into a psoriatic plaque twice a week during a 28 day treatment period. In such a treatment protocol the patient will be administered the pharmaceutical composition eight times and will receive 0.5 mg of the domain antibody during each administration such that a total dose of 4 mg of the domain antibody is received during the 28 day treatment period. This means, for example, that in a treatment protocol spanning 28 days the patient would receive the first 100 µL injection containing 0.5 mg of the domain antibody on day one, the second such injection on day four, the third such injection on day eight, the fourth such injection on day eleven, the fifth such injection on day fifteen, the sixth such injection on day eighteen, the seventh such injection on day twenty-two and the eighth such injection on day twenty-five. Domain antibody doses (e.g., 100 µL injection containing 0.5 mg of the domain antibody) in this treatment protocol are administered on a mg per patient basis.

The domain antibody can also be administered to a human patient with a psoriatic plaque according to a treatment protocol in which 100 µL of a pharmaceutical composition comprising 1 mg/mL of the domain antibody is injected into a psoriatic plaque once a week during a 28 day treatment period. In such a treatment protocol the patient will be administered the pharmaceutical composition four times and will receive 0.1 mg of the domain antibody during each administration such that a total dose of 0.4 mg of the domain antibody is received during the 28 day treatment period. This means, for example, that in a treatment protocol spanning 28 days the patient would receive the first 100 µL injection containing 0.1 mg of the domain antibody on day one, the second such injection on day eight, the third such injection on day fifteen, and the fourth such injection on day twenty-two. Domain antibody doses (e.g., 100 µL injection containing 0.1 mg of the domain antibody) in this treatment protocol are administered on a mg per patient basis. WO 2008/149148 describes methods of testing, isolating and producing the unmodified DOM1h-131-206 dAb and such methods are applicable to the modified TNFR1 dAbs of the present invention with reduced binding to ADAs e.g. to the DOM1h-131-206 dAb with an extension of a single alanine at the C-terminus (SEQ ID NO 16), and this disclosure (including methods of testing, isolating and producing) is incorporated herein.

In additional embodiments 1-36 below the invention also provides:

1. A single immunoglobulin variable domain (dAb) (e.g. VH, VL or a VHH), e.g. which binds to a target, which comprises one or more modifications selected from:
   (a) a C-terminal addition, extension or tag
   (b) one or more amino acid framework substitutions wherein at least one substitution is a substitution selected from: a P14A substitution, a P41A substitution and a L108A substitution;

and which has reduced binding to pre-existing ADAs compared to the unmodified single immunoglobulin variable domain (dAb).
2. A single immunoglobulin variable domain (dAb) according to 1. above, wherein said dAb is selected from a human VH, or VL dAb or a Camelid VHH.
3. A single immunoglobulin variable domain (dAb) according to 1 or 2, which comprises a C-terminal extension of at least one amino acid.
4. A single immunoglobulin variable domain (dAb) according to 3, wherein said C-terminal extension comprises an amino acid extension of from one amino acid to about 6 amino acids.
5. A single immunoglobulin variable domain (dAb) according to 3 or 4, wherein said C-terminal extension comprises an amino acid which is alanine.
6. A single immunoglobulin variable domain (dAb) according to 5, wherein said C-terminal extension consists of a single amino acid which is alanine.
7. A single immunoglobulin variable domain (dAb) according to claim 5, wherein said C terminal extension comprises an amino acid extension selected from: (a) AS, (b) AST (c) ASTK,(d) ASTKG, or (e) ASTKGP.
8. A single immunoglobulin variable domain (dAb) according to any of 1-2, wherein the C terminal has a tag selected from: affinity tag, a myc tag, FLAG tag, his-tags, chemical modification such as PEG, or protein domains such as the antibody Fc domain.
9. A single immunoglobulin variable domain (dAb) according to 6, wherein said dAb is a VH dAb and which further comprises a P14A framework substitution.
10. A single immunoglobulin variable domain (dAb) according to 7, wherein said dAb is a VH dAb and which further comprises a P14A framework substitution.
11. A single immunoglobulin variable domain (dAb) according to any of the preceding claims which binds to a target wherein said is selected from: TNFα, TNFR1, VEGF, IL-1R, IL-6R, IL-4, IL-5, IL-13, DC-SIGN, ASGPR, albumin, TGFβR2.
12. A single immunoglobulin variable domain (dAb) according to 11, which is selected from the following an amino acid sequence identified as: (a) DOM1h-131-206 dAb with an extension of a single alanine (SEQ ID NO 16) (b) DOM1h-131-206 dAb with an extension of a single alanine and a P14A framework mutation (SEQ ID NO 17) (c) DOM1h-131-206 dAb with a P14A framework mutation (SEQ ID NO 18) (d) DOM1h-131-206 dAb with an ASTKG C terminus extension (SEQ ID NO 19) (e) DOM1h-131-206 dAb with an ASTKG C terminus extension and a P14A framework mutation (SEQ ID NO 20).
13. A single immunoglobulin variable domain (dAb) according to 11 or 12, wherein the target is TNFR1 and the unmodified dAb is selected from an amino acid sequence that is 100%, 95%, 90%, 85% or 80% identical to the amino acid identified as: DOM1h-131-206 (SEQ ID NO 1), DOM 1h-131-511 (SEQ ID NO 2), DOM 1h-131-202 (SEQ ID NO 3).
14. A single immunoglobulin variable domain (dAb) according to any preceding claim, wherein the dAb is present as a fusion or conjugate with additional molecules.
15. A single immunoglobulin variable domain (dAb) according to 14, wherein the dAb is present as a fusion or conjugate with one or more additional molecules selected from: an additional dAb, a protein or polypeptide or fragment thereof e.g. which is half life extending or is a further therapeutic or active molecule, a PEG molecule, an antibody or a fragment thereof e.g. an Fc region.
16. A single immunoglobulin variable domain (dAb) according to 15, wherein the dAb is present as a mAbdAb molecule.
17. A pharmaceutical composition comprising a single immunoglobulin variable domain (dAb) according to any of the preceding in combination with a pharmaceutically or physiologically acceptable carrier, excipient or diluent.
18. The pharmaceutical composition according to 17, which comprises further therapeutic or active agents.
19. A pharmaceutical composition according to 17 or 18 which comprises an anti-TNFR1 dAb.
20. A pharmaceutical composition according to 19, which comprises an anti-TNFR1 dAb according to any one of 12-13.
21. A single immunoglobulin variable domain (dAb) according to any of claims 1-16 or a composition according to any of 17-20, for use in medicine.
22. A method of treating or preventing at least one disease or disorder or condition selected from an inflammatory disease or disorder or a respiratory or pulmonary disease or disorder by administering to a subject a therapeutically or prophylactically effective amount of a composition according to any one 19-20 or a dAb according to 11-13.
23. The method of 22, wherein said at least one disease or disorder or condition is selected from: psoriasis, arthritis, multiple sclerosis, inflammatory bowel disease (e.g.) Crohn's disease and ulcerative colitis; or for example respiratory or pulmonary diseases or disorders, e.g selected from: chronic obstructive pulmonary disease, chronic bronchitis, chronic obstructive bronchitis and emphysema, lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis and Acute lung injury (ALI), and Acute Respiratory Distress syndrome (ARDS) and complications thereof.
24. The method according to 23, wherein said disease is ALI and said dAb is a dAb according to claim 13 or said pharmaceutical composition comprises a dAb according to claim 13.

25. The method according to any one of 22-24, wherein said composition or dAb is delivered to a subject by subcutaneous, intravenous or intramuscular injection.
26. The method according to any one of 22-24, wherein said composition or dAb is delivered to a subject via parenteral, oral, rectal, transmucosal, ocular, pulmonary or GI tract delivery.
27. An injectable, oral, inhalable or nebulisable formulation which comprises a composition or a dAb according to any one of 1-20.
28. A sustained release formulation which comprises a composition according to any one of claims 1-20.
29. A freeze dried formulation which comprises a composition according to any one of 1-20.
30. A delivery device comprising a composition according to any one of 1-20.
31. A delivery device comprising a composition according to any one of 1-20, wherein said device is a nebulizer or an inhaler.
32. An isolated or recombinant nucleic acid encoding a dAb according to any of 1-16.
33. An isolated or recombinant nucleic acid encoding a dAb according to any of 12-13.
34. A vector comprising a nucleic acid of 32 or 33.
35. A host cell comprising the nucleic acid of claim 32 or 33 or the vector of 34.
36. A method of producing a polypeptide comprising a dAb according to any of 1-16, wherein said method comprises maintaining a host cell of 35 under conditions suitable for expression of said nucleic acid or vector, whereby a polypeptide is produced.
37. A dAb according to 1-16, wherein the dAb binds to ADA with a KD which is 150% or more of the KD of the unmodified dAb (e.g. 200%, 250%, 300%, 350%, 400%, 450%, 500%, 550%, 600%, 650% or more).

The invention also provides the following embodiments listed as 1b-25b:

1b. A single immunoglobulin variable domain (dAb) which does not bind (or has reduced binding) to pre-existing human ADA in human sera, wherein the epitope on the dAb to which ADA binds is masked.
2b. A dAb according to 1b above, which has a KD of binding to ADA which is 150% or more (e.g. 200%, 250%, 300%, 350%, 400%, 450%, 500%, 550%, 600%, 650% or more) of the KD of an equivalent sequence in which the epitope is not masked.
3b. A dAb according to 1b-2b wherein the epitope is masked by:
  a. Addition of a chemical entity to the C-terminus; and/or
  b. one or more framework substitution(s); and/or
  c. one or more deletions
4b. A dAb according to 3b wherein the chemical entity comprises, one or more amino acid(s), a C-terminal tag, or a chemical modification such as pegylation or amidation.
5b. The dAb according to 3b or 4b wherein (a), (b) and/or (c) has a direct conformational effect on the epitope, an indirect conformation effect on the epitope, and/or sterically hinders the epitope.
6b. The dAb according to any of the preceding wherein said epitope;
  d. Overlaps with Kabat residue 113 at the C-terminus; and/or
  e. Overlaps with Kabat residues 14, 41, 108, 110, 112 and 113; and/or
  f. Comprises the surface exposed Kabat residues 14, 41, 108, 110, 112 and 113, and any other residue within 5 angstroms of these positions; and/or
  g. Comprises framework 4, and the loops between the beta-strands of frameworks 1 and 2.
7b. A dAb according to any preceding embodiment 1b-6b, which comprises one or more amino acid substitutions at Kabat positions 14, 41, 108, 110, or 112 compared to a human germline framework sequence
8b. A humanised single immunoglobulin variable domain (dAb) which has a non-human sequence at one or more of the following residues: Kabat residues 14, 41, 108, 110 and/or 112.
9b. A dAb according to 7b or 8b wherein the amino acid residues at said one or more positions are alanine residues.
10b. A dAb according to any of the preceding embodiments 1b-9b, wherein said masking is achieved by the provision of an amino acid extension to the C-terminus of the dAb.
11b. A dAb according to 10b wherein said extension is between 1 and 8 amino acids.
12b. A dAb according to 10b or 11b wherein said extension comprises an alanine residue.
13b. A dAb according to 12b wherein said extension consists of a single alanine residue.
14b. A dAb according to 12b wherein said extension is selected from the group consisting of: AS, AST, ASTK, ASTKG, and ASTKGP.
15b. A dAb according to any of 1b-14b, wherein said dAb is a VH or VL or a VHH dAb.
16b. A dAb according to any of 1b-15b, wherein the target to which the dAb binds is TNFα, TNFR1, VEGF, IL-1R, IL-6R, IL-4, IL-5, IL-13, DC-SIGN, ASGPR, albumin, and TGFβR2.
17b. A single immunoglobulin variable domain (dAb) according to 16b, which is selected from the following amino acid sequences identified as: (a) DOM1h-131-206 dAb with an extension of a single alanine (SEQ ID NO 16); (b) DOM1h-131-206 dAb with an extension of a single alanine and a P14A framework mutation (SEQ ID NO 17) (c) DOM1h-131-206 dAb with a P14A framework mutation (SEQ ID NO 18); (d) DOM1h-131-206 dAb with an ASTKG C terminus extension (SEQ ID NO 19); and (e) DOM1h-131-206 dAb with an ASTKG C terminus extension and a P14A framework mutation (SEQ ID NO 20).
18b. A single immunoglobulin variable domain (dAb) according to 16b or 17b, wherein the target is TNFR1 and the unmodified dAb is selected from a sequence that is 100%, 95%, 90%, 85% or 80% identical to the amino acid identified as: DOM1h-131-206 (SEQ ID NO 1), DOM 1h-131-511 (SEQ ID NO 2), DOM 1h-131-202 (SEQ ID NO 3).
19b. A method of masking an epitope on a single immunoglobulin variable domain (dAb), which epitope binds to pre-existing human ADA in human sera, comprising the step of modifying the epitope.
20b. A method of reducing binding of a single immunoglobulin variable domain (dAb) to pre-existing human ADA in human sera, comprising masking the epitope on the dAb to which ADA binds.
21b. A method according to 19b or 20b in which said masking causes a reduction in binding to ADA such that the dAb comprising the masked epitope has a KD which is 150% or more of the KD of a dAb in which the epitope is not masked.

22b. A method according to any of 19b-21b wherein the epitope is masked by:
  h. Addition of a chemical entity to the C-terminus; and/or one
  i. or more framework substitution(s); and/or
  j. one or more deletions
23b. A method according to 22b, wherein the chemical entity comprises, one or more amino acid(s), a C-terminal tag, or a chemical modification such as pegylation or amidation.
24b. The method according to 22b or 23b wherein (a), (b) and/or (c) has a direct conformational effect on the epitope, an indirect conformation effect on the epitope, and/or sterically hinders the epitope.
25b. A method according to any of 19b-24b above wherein said epitope;
  k. Overlaps with Kabat residue 113 at the C-terminus;
  l. Overlaps with kabat residues 14, 41, 108, 110, 112 and 113; and/or
  m. Comprises the surface exposed Kabat residues 14, 41, 108, 110, 112 and 113, and any other residue within 5 angstroms of this surface; and/or
  n. Comprises framework 4, and the loops between the beta-strands of frameworks 1 and 2.

In further embodiments 1c-15c below the invention provides:

1c. A humanised VHH single immunoglobulin variable domain which retains one or more camel germline residue(s) at Kabat residues 14 and/or 108.
2c. A single immunoglobulin variable domain according to is above which has a KD of binding to human ADA in human serum which is 150% or more (e.g. 200%, 250%, 300%, 350%, 400%, 450%, 500%, 550%, 600%, 650% or more) of the KD of an equivalent sequence in which residues 14 and/or 108 have been humanised.
3c. A single immunoglobulin variable domain according to is or 2c in which one or more C terminal amino acids has been deleted.
4c. A single immunoglobulin variable domain according to 3c wherein one C terminal amino acid has been deleted.
5c. A single immunoglobulin variable domain according to is or 2c which comprises a C-terminal addition, extension or tag.
6c A single immunoglobulin variable domain according to 5c wherein said addition, extension or tag is selected from the group consisting of: one or more amino acid(s) extension, a C-terminal tag, or a chemical modification such as pegylation or amidation.
7c. A single immunoglobulin variable domain according to 5c or 6c in which said extension is between 1 and 8 amino acids.
8c. A single immunoglobulin variable domain according to 7c wherein said extension comprises an alanine residue.
9c. A single immunoglobulin variable domain according to 8c wherein said extension consists of a single alanine residue.
10c. A single immunoglobulin variable domain according to 8c wherein said extension is selected from the group consisting of: AS, AST, ASTK, ASTKG, ASTKGP, ASTKA, ASTKAP and ASTKAPS.
11c. A single immunoglobulin variable domain according to any of the preceding embodiments 1c-10c which additionally comprises non-human residues at one or more of the following residues: Kabat residues 41, 110 and/or 112.
12c. A single immunoglobulin variable domain according to any of the preceding embodiments wherein the target to which the dAb binds is TNFα, TNFR1, VEGF, IL-1R, IL-6R, IL-4, IL-5, IL-13, DC-SIGN, ASGPR, albumin, and TGFβR2.
13c. A method of humanisation of a Camelid VHH single immunoglobulin variable domain comprising retaining one or more camel germline residue(s) at Kabat residues: 14 and/or 108.
14c. A method of reducing binding of a Camelid VHH single immunoglobulin variable domain (dAb) to pre-existing ADA, comprising retaining a camel germline residue at Kabat residues: 14 and/or 108.
15c. A method according to 13c or 14c, in which said retention causes a reduction in binding to ADA such that the VHH comprising the Camelid residues at positions 14 and/or 108 has a KD of binding to human ADA in human serum which is 150% or more of the KD of a VHH with an equivalent sequence in which these residues have been humanised.

Note that the term dAb as used herein is a registered trademark.

EXAMPLES

Example 1

Frequency of Healthy Subjects with Pre-existing ADA to the dAb Designated DOM1H-131-206

DOM1H-131-206 (VH) ADA Assay Procedure

DOM1H-131-206 (SEQ ID NO 1) is biotinylated at a biotin molar challenge ratio of 8:1. After labelling, biotinylated DOM1H-131-206 (SEQ ID NO 1) is buffer-exchanged and stored in a formulation buffer containing 14 mM Sodium Phosphate, 8.4% sucrose, 0.35% glycine, 0.014% polysorbate 80 at pH 7.4.

DOM1H-131-206 is ruthenium labelled at a Sulfo-Tag molar challenge ratio of 5:1. After labelling, Sulfo-TAG labelled DOM1H-131-206 is buffer-exchanged and stored in a formulation buffer containing 14 mM Sodium Phosphate, 8.4% sucrose, 0.35% glycine, 0.014% polysorbate 80 at pH 7.4.

The anti-drug antibody (ADA) assay is a bridging assay performed on the MSD™ ECL (electrochemiluminescence) technology platform. The MSD™ technology (available from Meso scale Discovery, Matyland, USA) utilizes a ruthenium metal chelate as the ECL label in conjunction with carbon electrodes placed within the wells of a microtiter plate that are coated with streptavidin. The bound Sulfo-Tag™ used in the assay produces a chemiluminescence signal that is triggered when voltage is applied by the instrument (Meso Scale Discovery Sector™ Imager 6000). The resulting luminescence signal is measured in ECL™ units. The intensity of the signal is directly proportional to the quantity of detected antibodies in the sample. Negative (normal human serum; NHS) and positive (PC; mouse anti-DOM1H-131-206 idiotypic antibody spiked in normal human serum) control samples (QCs) are run on each assay plate.

The summary of assay procedures is described below:
1. A MSD™ streptavidin plate is blocked with 150 µL/well blocking Casein in PBS (1%) at room temperature (RD for 1-2 hours. The blocker is removed without washing.
2. After a 1 hour pre-incubation, a homogeneous mixture containing 0.1 pg/mL biotinylated DOM1H-131-206 (drug), 0.1 µg/mL ruthenylated ("Sulfo-Tag"™) DOM1H-131-206 (drug), and 2% serum sample in assay diluent (1% Casein in PBS) is transferred to the MSD™ plate and incubated for 1 hour±5 minutes at RT.
3. The MSD plate is then washed 3 times with PBST.
4. 150 µL/well read buffer is added and the plate is read.

During validation of this specific immunoassay, a panel of 60 healthy human donor serum samples was screened for background reactivity in the assay. It was determined that approximately 45% of serum samples from these subjects had detectable VH-reactive autoantibodies, mostly of the IgG isotype, which were able to bind to DOM1H-131-206 (results shown in FIG. 1).

Free unlabelled DOM1H-131-206 competes for ADA binding in this assay resulting in reduced signal intensity (high % signal inhibition) This 'Confirmation Assay' was used to determine whether modified versions of DOM1H-131-206 and other antibody based molecules could compete with DOM1H-131-206 for ADA binding.

Example 2

Amino Acid Substitutions to the VH Framework of DOM1h-131-206

Free, unlabelled DOM1H-131-206 competes for ADA binding and results in reduced signal intensity in the DOM1H-131-206 ADA assay as described above. This 'Confirmation Assay' was therefore used to determine whether test materials e.g. DOM1H-131-206, modified versions of DOM1H-131-206, or other antibody based molecules ('test material'), could also inhibit ADA binding to DOM1H-131-206.

To investigate whether the binding of ADA to the VH framework could be reduced, a number of amino acid substitutions and other modifications were made to the framework of DOM1h-131-206 by standard site-directed mutagenesis techniques.

Molecules with substitutions (test materials) were assayed using the following method (Confirmation Assay):
DOM1H-131-206 Confirmation Assay Procedure (which can be Used to Screen VH dAbs for ADA Binding):
1. 10 µg/mL DOM1H-131-206 or other test material such as modified dAbs, is pre-incubated for 1 hour±5 minutes at RT with 4% ADA positive human serum in assay diluent (1% casein in PBS).
2. A MSD™ streptavidin plate is blocked with 150 µL/well blocking casein in PBS (1%) at room temperature (RT) for 1-2 hours. The blocker is removed without washing.
3. In a microtitre assay plate, the sample containing ADA positive human serum sample and 10 µg/mL test material such as modified dAbs is added to a homogeneous mixture of biotinylated DOM1H-131-206 (SEQ ID NO 1) (drug) and ruthenylated ("Sulfo-Tag"™) DOM1H-131-206 (SEQ ID NO 1) (drug) in assay diluent (1% casein in PBS) such that the final concentrations are 2% ADA positive human serum, 0.1 µg/mL biotinylated DOM1H-131-206 (SEQ ID NO 1) (drug) and 0.1 µg/mL ruthenylated ("Sulfo-Tag"™) DOM1H-131-206 (SEQ ID NO 1) (drug) and incubated for 1 hour±5 minutes at RT.
4. After the 1 hour incubation, the assay samples are transferred to the blocked MSD plate, and the plate is incubated for 1 hour±5 minutes in the dark at RT.
5. The MSD™ plate is then washed 3 times with PBST
6. 150 µL/well read buffer is added and the plate is read.

For each experiment with a different parental clone (results shown in Table 1) human serum samples from 10 ADA positive subjects were tested in the confirmation assay above (in Example 2): Results are shown in Table 1b as both the (overall) mean % inhibition of signal and also the % subjects with ADA binding. The lower the % inhibition of signal the less the modified compound was able to bind to ADAs. A cut off of about 40.5% in % inhibition of signal was taken to show negligible ADA binding.

Using the confirmation assay, it was determined that amino acid substitutions at the following positions significantly reduced pre-existing ADA binding to DOM1H-131-206 while retaining potency for antigen binding i.e. binding to TNFR1 as determined using a TNFR1 affinity assay procedure shown in Example 5c (results shown in Table 1): P14A, P41A, L108Q.

Example 3

Amino Acid Extensions to the VH Framework of DOM1H-131-206

To determine whether modification of the C-terminus of the VH framework could reduce ADA binding, a number of C-terminal modifications were made to frameworks by standard site-directed mutagenesis techniques. Molecules with substitutions (test materials) were assayed using the 'confirmation assay' as described previously in Example 2) and results are shown below in Table 1.

Extension of the C-terminus DOM1H-131-206 or other molecules tested also significantly reduced pre-existing ADA binding (Table 1, Table 2). Results shown in Table 2 were also obtained using the 'confirmation assay' as described previously in Example 2. This is exemplified by extensions A, AS, AST, ASTK, ASTKG, ASTKGP, AAA, and all longer extensions tested. VHH clones that have not been humanised have generally lower levels of binding to ADAs.

TABLE 1

Assessment of ADA binding to DOM1H-131-206 mutants

| Parental clone | Sequence modification | Mean % inhibition of signal in confirmation assay (mean value—of 10 subjects) | % subjects with ADA binding (10 subjects) |
| --- | --- | --- | --- |
| DOM 1H-131-206 | Unmodified | 99.47 | 100 |
| DOM 1H-131-206 | Q13A | 99.21 | 100 |
| DOM 1H-131-206 | P14A | 58.32 | 100 |
| DOM 1H-131-206 | P41A | 87.35 | 100 |
| DOM 1H-131-206 | K43A | 99.51 | 100 |
| DOM 1H-131-206 | G44E | 99.47 | 100 |
| DOM 1H-131-206 | R83A | 99.32 | 100 |
| DOM 1H-131-206 | H91S | 99.38 | 100 |
| DOM 1H-131-206 | L108Q | 90.92 | 100 |
| DOM 1H-131-206 | P14A, G44E | 61.61 | 100 |
| DOM 1H-131-206 | G44E, H91S | 99.11 | 100 |
| DOM 1H-131-206 | P14A, H91S | 50.23 | 60 |
| DOM 1H-131-206 | G44E, L108Q | 91.29 | 100 |

TABLE 1-continued

Assessment of ADA binding to DOM1H-131-206 mutants

| Parental clone | Sequence modification | Mean % inhibition of signal in confirmation assay (mean value—of 10 subjects) | % subjects with ADA binding (10 subjects) |
|---|---|---|---|
| DOM 1H-131-206 | Unmodified | 96.13 | 100 |
| DOM 1H-131-206 | C-terminal A | 15.74 | 0 |
| DOM 1H-131-206 | C-terminal AS | 16.28 | 0 |
| DOM 1H-131-206 | C-terminal AST | 26.41 | 50 |
| DOM 1H-131-206 | C-terminal ASTK | 19.60 | 40 |
| DOM 1H-131-206 | C-terminal ASTKG | 28.27 | 40 |
| DOM 1H-131-206 | C-terminal ASTKGP | 42.63 | 60 |

% inhibition = ADA binding (% inhibition of signal when the given protein is competed in the ADA bridging assay (confirmation assay)).

TABLE 2

Assessment of ADA binding of VHH molecules and VH domain antibodies with c-terminal extensions

| Parental clone | Sequence modification | Mean % inhibition of signal in confirmation assay (mean value—of 10 subjects) | % subjects with ADA binding (10 subjects) |
|---|---|---|---|
| Pascolizumab-DT04-H-033 | Unmodified | 99.48 | 100 |
| Pascolizumab-DT04-H-033 | C-terminal AAA | 3.46 | 0 |
| Pascolizumab-DT04-H-033 | C-terminal AST | 3.44 | 0 |
| Pascolizumab-DT04-H-033 | C-terminal AS | 4.12 | 0 |
| Pascolizumab-DT04-H-033 | C-terminal A | 7.46 | 0 |
| DOM1h-574-208 | Unmodified | 94.13 | 100 |
| DOM1h-574-208-VL fusion | C-terminal VL dAb | 4.43 | 0 |
| DT04-H-033 | C-terminal AAA | 10.98 | 0 |
| DT04-H-033 | C-terminal AST | 14.00 | 0 |
| DT04-H-033 | C-terminal AS | 8.26 | 0 |
| DT04-H-033 | C-terminal A | 12.48 | 0 |
| DT04-H-033 | C-terminal FLAG (a 6 amino acid peptide sequence) | 12.80 | 0 |
| VHH clone 2-40842 (IL6R) | Unmodified | 18.66 | 20 |
| VHH clone 7-40842 (IL6R) | Unmodified | 21.96 | 20 |
| VHH clone 3-40955 (RANKL-Camelid) | Unmodified | 23.68 | 20 |
| VHH clone 8-41015 (RANKL-Camelid) | Unmodified | 20.08 | 20 |
| VHH clone 9-41016 (RANKL-humanised) | Unmodified | 88.45 | 100 |

% inhibition = ADA binding (% inhibition of signal when the given protein is competed in the ADA bridging assay). The sequence of the FLAG tag can be found in Nature Biotechnology 1988, Vol 16, pp1204-1210.
Note that (mean) 40% inhibition of signal (or less than 40% inhibition of signal) is taken to show negligible ADA binding.

Example 4

Combination of Amino Acid Substitutions and C-terminal Extension to the VH Framework of DOM1H-131-206

To determine whether a combination of amino acid substitutions and modification of the C-terminus of the VH framework could reduce ADA binding, a number of C-terminal modifications and/or amino acid substitutions were made to frameworks by standard site-directed mutagenesis techniques. Molecules with substitutions were assayed using the 'confirmation assay' described previously in Example 2). Results are shown below in Table 3:

TABLE 3

| Parental clone | Sequence modification | Mean % inhibition of signal in confirmation assay (mean value—of 10 subjects) | % subjects with ADA binding (10 subjects) |
|---|---|---|---|
| DOM 1H-131-206 | C-terminal A | 1.12 | 0 |
| DOM 1H-131-206 | C-terminal ASTKG | 1.77 | 0 |
| DOM 1H-131-206 | P14A + C-terminal A | 8.76 | 0 |
| DOM 1H-131-206 | P14A + C-terminal ASTKG | 11.93 | 0 |
| DOM 1H-131-206 | C-terminal AST | 34.96 | 20 |
| DOM 1H-131-206 | C-terminal S deletion (ΔS) | 44.67 | 40 |
| DOM 1H-131-206 | P14E | 47.22 | 60 |
| DOM 1H-131-206 | P14K | 46.70 | 50 |
| DOM 1H-131-206 | P14Q | 52.87 | 60 |
| DOM 1H-131-206 | P14T | 68.86 | 100 |
| DOM 1H-131-206 | L11A | 97.96 | 100 |
| DOM 1H-131-206 | A84T | 90.96 | 100 |
| DOM 1H-131-206 | L108A | 94.30 | 100 |
| DOM 1H-131-206 | T110A | 78.84 | 100 |
| DOM 1H-131-206 | S112A | 77.11 | 80 |
| DOM 1H-131-206 | P14K + C-terminal A | 29.13 | 10 |
| DOM 1H-131-206 | P14K + C-terminal ASTKG | 25.01 | 10 |
| DOM 1H-131-206 | P14Q + C-terminal A | 29.66 | 20 |
| DOM 1H-131-206 | P14Q + C-terminal ASTKG | 21.76 | 10 |
| DOM 1H-131-206 | P14T + C-terminal A | 32.97 | 20 |
| DOM 1H-131-206 | P14T + C-terminal ASTKG | 17.19 | 0 |

Example 5a and 5b

Affinity of DOM1H-131-206 C-terminal Extension

Further studies were undertaken to determine whether modifications to DOM1H-131-206 that reduce binding of pre-existing ADA resulted in any changes to the affinity of this dAb for its target, human TNFR1.

Example 5a Assessment of TNFR1 Binding of DOM1H-131-206 Mutants by ELISA

The ability of modified variants of DOM 1H-131-206 (test dAbs) to bind to human TNFR1 was determined by ELISA. It was observed that framework mutation and C-terminal modifications which were shown to reduce pre-existing ADA binding generally had comparable binding to TNFR1 compared with the parental DOM1H-131-206 dAb. The exception was DOM1H-131-206 with a C-terminal extension of ASTKGP, which had approximately 5-fold lower EC50 for TNFR1 binding compared with the parental dAb DOM1H-131-206.

TNFR1 ELISA Binding Assay Protocol:
1. Recombinant human TNFR1-Fc (R&D Systems) is added to 96-well ELISA plates at a final concentration of 0.1 µg/mL in carbonate-bicarbonate buffer pH9.4 (Pierce).
2. After overnight incubation at 4° C., excess TNFR1:Fc is removed by washing three times with wash buffer (Wash Buffer—0.1% Tween-20/PBS) and three times with PBS.
3. Plates are blocked with 1% BSA in PBS for 1 hour at room temperature. Block is removed by washing as above and then test dAb samples diluted in assay diluent (0.1% BSA+0.05% Tween-20/PBS) are added to the plate and incubated for 1 hour at room temperature.
4. After washing as above, a polyclonal rabbit anti-human Ig (Vh specific) at a dilution of 1:1000 in assay diluent is added and incubated for 1 hour at room temperature.
5. After washing as above, a mouse anti-Rabbit HRP conjugate antibody is added at a dilution of 1:10,000 in assay diluent and incubated for 1 hour at room temperature.
6. After washing as above 100 uL of SureBlue TMB substrate is added to each well. Once sufficient blue colour has developed, the enzymatic reaction is stopped with 100 µL of 1M HCl and the plate is read plate at 450 nm.
7. Dose response curves for each test dAb are prepared by plotting concentration against absorbance values. EC50 values for dAb binding to TNFR1 are determined using Graphpad Prism.

TABLE 4a

Assessment of binding to TNFR1 for DOM1H-131-206 mutants

| Parental clone | Sequence modification | Mean EC50 for TNFR1 binding (nM) |
|---|---|---|
| DOM 1H-131-206 | Unmodified | 1.99 |
| DOM 1H-131-206 | Q13A | 1.75 |
| DOM 1H-131-206 | P14A | 1.22 |
| DOM 1H-131-206 | P41A | 0.59 |
| DOM 1H-131-206 | K43A | 0.67 |
| DOM 1H-131-206 | G44E | 0.86 |
| DOM 1H-131-206 | R83A | 0.76 |
| DOM 1H-131-206 | H91S | 0.96 |
| DOM 1H-131-206 | L108Q | 0.85 |
| DOM 1H-131-206 | P14A, G44E | 2.03 |
| DOM 1H-131-206 | G44E, H91S | 3.50 |
| DOM 1H-131-206 | P14A, H91S | 0.75 |
| DOM 1H-131-206 | G44E, L108Q | 1.64 |
| DOM 1H-131-206 | Unmodified | 1.99 |
| DOM 1H-131-206 | C-terminal A | 1.21 |
| DOM 1H-131-206 | C-terminal ASTK | 1.59 |
| DOM 1H-131-206 | C-terminal ASTKG | 1.11 |
| DOM 1H-131-206 | C-terminal ASTKGP | 11.89 |

TABLE 4b

Assessment of binding to TNFR1 for DOM1H-131-206 mutants

| Parental clone | Sequence modification | Mean EC50 for TNFR1 binding (nM) |
|---|---|---|
| DOM 1H-131-206 | Unmodified | 0.67 |
| DOM 1H-131-206 | P14A + C-terminal A | 0.57 |
| DOM 1H-131-206 | P14A + C-terminal ASTKG | 1.47 |
| DOM 1H-131-206 | C-terminal AST | 1.99 |
| DOM 1H-131-206 | C-terminal S deletion (ΔS) | 0.50 |
| DOM 1H-131-206 | P14E | 0.64 |
| DOM 1H-131-206 | P14K | 0.72 |
| DOM 1H-131-206 | P14Q | 0.91 |
| DOM 1H-131-206 | P14T | 0.77 |
| DOM 1H-131-206 | L11A | 0.51 |
| DOM 1H-131-206 | A84T | 0.79 |
| DOM 1H-131-206 | L108A | 0.70 |
| DOM 1H-131-206 | T110A | 0.29 |
| DOM 1H-131-206 | S112A | 1.19 |
| DOM 1H-131-206 | P14K + C-terminal A | 0.46 |
| DOM 1H-131-206 | P14K + C-terminal ASTKG | 0.48 |
| DOM 1H-131-206 | P14Q + C-terminal A | 0.46 |
| DOM 1H-131-206 | P14Q + C-terminal ASTKG | 1.10 |
| DOM 1H-131-206 | P14T + C-terminal A | 0.66 |
| DOM 1H-131-206 | P14T + C-terminal ASTKG | 0.72 |

TABLE 4c

Assessment of binding to TNFR1 for DOM1H-131-206 mutants

| Parental clone | Sequence modification | Mean EC50 for TNFR1 binding (nM) |
|---|---|---|
| DOM 1H-131-206 | Unmodified | 1.97 |
| DOM 1H-131-206 | C-terminal A | 2.71 |
| DOM 1H-131-206 | P14A + C-terminal A | 2.22 |
| DOM 1H-131-206 | C-terminal ASTKG | 1.90 |
| DOM 1H-131-206 | P14A + C-terminal ASTKG | 4.64 |

Example 4b

TNFR1 Affinity Assay Procedure Using Biacore™

Affinity of a modified DOM1H-131-206 dAb with a C terminal A extension was determined by surface Plasmon resonance using a Biacore™ T100. Anti-human IgG antibody was immobilised to a CM4 chip, and human TNFR1:Fc was captured on this surface to a level of approximately 60 relative units. Test materials diluted in buffer to final concentrations of 25 nM to 0.024 nM (in a 4 fold dilution range) were injected over the TNFR1:Fc. Binding curves generated were double referenced using a 0 nM test material curve, and data fitted to a 1:1 binding model to generate kinetic data. Binding of test material to cynomolgus monkey TNFR1 was determined in the same way. Binding kinetic data are shown below in Table 4d below.

In conclusion the binding kinetics of modified (i.e. with addition of a C terminal A) and unmodified TNFR1dAbs were similar.

TABLE 4d

| DOM1H-131-206 modification | | Binding kinetics | |
|---|---|---|---|
| | Ka (M−1·s−1) (×10$^6$) | Kd (s−1) (×10$^{-4}$) | KD (M) (×10$^{-11}$) |
| Human TNFR1 | | | |
| C-terminal A | 9.02 | 2.29 | 2.53 |
| Unmodified | 9.94 | 1.42 | 1.43 |
| Cynomolgus monkey TNFR1 | | | |
| Unmodified | 10.10 | 1.51 | 1.50 |
| C-terminal A | 9.60 | 1.89 | 1.97 |

(no errors calculated for above data)

Example 6

Pharmacokinetics of DOM1H-131-206 C-terminal Extension

Further studies were undertaken to determine whether modifications to DOM1H-131-206 that reduce binding of pre-existing ADA resulted in any changes to the pharmacokinetics of this dAb.

Pharmacokinetic Procedure

The systemic exposure of DOM 1H-131-206 and DOM 1H-131-206 with a C-terminal alanine extension was determined in Cynomolgus monkeys. Separate groups of 5 Cynomolgus monkeys were dosed with test materials by a 30 minute intravenous infusion. Plasma samples were collected up to 48 hours post dosing and the levels of the two test materials determined by immunoassay. Briefly, biotinylated antibody specific to the test material was added to a streptavidin-coated 96-well microtitre plate, following which the monkey plasma samples were added. Digoxiginin-labelled human TNFR1:Fc was added, after which a horseradish peroxidase conjugated anti-digoxiginin antibody was added. Finally TMB substrate (available from R+D systems) was added and the amount of test material determined by back calculation of colourimetric signal from a test material standard curve.

No notable (>2-fold) changes gender-averaged systemic exposure parameters were observed when DOM-1H131-206 was compared with DOM-1H131-206 +A in cynomolgus monkeys after intravenous infusion. We conclude that modifications to DOM1H-131-206 by the addition of a C-terminal extension (+A) did not affect the pharmacokinetics of the dAb (shown in Table 5).

TABLE 5

Pharmacokinetics of DOM1H-131-206 mutants after a single intravenous dose in Cynomolgus monkeys

| Parental clone | Sequence modification | Plasma-half life ± standard deviation | Clearance (mL/min/kg) | Volume of distribution ± standard deviation |
|---|---|---|---|---|
| DOM 1H-131-206 | Unmodified | 2.80 ± 0.32 | 1.48 ± 0.21 | 0.25 ± 0.05 |
| DOM 1H-131-206 | C-terminal A | 2.57 ± 0.64 | 2.31 ± 0.49 | 0.34 ± 0.04 |

Example 7a

Expression of DOM1H-131-206 variants

To determine whether modifications to the VH framework which reduce pre-existing ADA binding have an impact on expression of the anti-TNFR1 dAb, the yield of a panel of modified variants of anti-TNFR1DOM1H 131-206 dAbs was compared with the parental clone after growth in 1 liter fermentation vessels. The test dAbs incorporated a C-terminal extension (+A or +ASTKG), with or without a framework substitution (P14A). The test dAbs were expressed in the same E. Coli strain, using the same microbial expression vector (pave011 (Aveda)) as the unmodified DOM1H 131-206 (SEQ ID NO 1). At small scale expression level (1 L), the overall yield for the dAbs with the C-terminal extensions +A or +ASTKG was similar to the unmodified parental clone. The yield for dAbs with the P14A substitution and C-terminal extension (+A or +ASTKG) was reduced compared with the unmodified parental clone (Table 6a).

Expression Procedure

A 'seed expansion' stage was completed by inoculating a 100 ml shake flask with a vial of E. Coli cells expressing the dAb construct in a microbial expression vector.

After approximately 10 hours of growth the seed flask is used to inoculate a 1 L fermenter. The production process is made up of three stages, batch, fed-batch and induction. The initial batch phase lasts for approximately 13 hours during which time the culture is growing exponentially at 37° C. (stepped-down to 30° C. for the last 4 hours) until the primary carbon source, glycerol, is depleted. At the time of glycerol depletion a spike in dissolved oxygen (DO) occurs and the nutrient feed commences (fed-batch stage). Around 5 hours after the start of the nutrient feed (at an OD$_{600}$ of 75) the culture is induced with IPTG (induction stage) and during this phase of the process product is made and released into the medium. The batch is stopped approximately 48 hours after induction and the amount of dAb in the supernatant was quantified by HPLC.

TABLE 6a

Expression of titres of DOM1H-131-206 variants

| Parental clone | Sequence modification | Harvest supernatant titre (g/L) |
|---|---|---|
| DOM1H-131-206 | Unmodified | 2.71 |
| DOM1H-131-206 | C-terminal A | 3.15 |
| DOM1H-131-206 | C-terminal ASTKG | 2.22 |
| DOM1H-131-206 | P14A + C-terminal A | 0.29 |
| DOM1H-131-206 | P14A + C-terminal ASTKG | 0.18 |

Conclusions from this experiment were as follows:
1) DOM1H-131-206 +A, DOM1H-131-206 +ASTKG and wild type mutants exhibited very good dAb expression. The highest titre was about 3000 mg/L.
2) DOM1H-131-206 P14 +A, and DOM1H-131-206 p14 +ASTKG mutants couldn't express dAb in the process.
3) In general, DOM1H-131-206 +A and DOM1H-131-206+ ASTKG were comparable with wild type in terms of dAb expression level Example 7b Stability of DOM1H-131-206 with a C-terminal Alanine The stability of the C-terminal alanine extension of DOM 1H-131-206 +A was determined in human serum, lung homogenate or liver homogenate measured using a validated immunoassay for DOM 1H-131-206 (described below) which detects DOM 1H-131-206 but is very weakly cross-reactive to DOM 1H-131-206+A. This is due to the fact that the detection antibody M2.3G10.1G06 binds strongly to DOM 1H-131-206 but poorly to DOM 1H-131-206 +A. The assay format uses human TNFR1:Fc as a capture reagent and therefore is considered to be specific for intact, functional dAb.

It was observed that plasma spiked with 2 µg/mL of DOM 1H-131-206 +A gave a reading of ~6.4 ng/mL in this assay, while buffer spiked with 2 µg/mL of GSK2862277 gave a reading of 11.3 ng/mL. Thus cross reactivity of DOM 1H-131-206 +A in the DOM 1H-131-206 assay was estimated at between 0.25-0.5%.

To study conversion, human whole blood, human lung homogenate (10 mg protein/ml), or human liver homogenate (10 mg protein/ml) were spiked with 1 µg/ml of either DOM 1H-131-206, DOM 1H-131-206 +A or buffer (no drug added). Following incubation for either 0, 3 h, 6 h or 24 h, plasma/supernatant was collected by centrifugation and samples frozen prior to assay for DOM 1H-131-206 using the validated immunoassay (working range of 0.1 to 10 ng/ml).

Over 24 h there was no evidence of significant conversion of DOM 1H-131-206 +A to DOM 1H-131-206 in either matrix, which would have been evidenced by increasing signal in the immunoassay (due to formation of DOM 1H-131-206). This suggests that the additional C-terminal alanine is not prone to rapid proteolytic cleavage.

Protocol for DOM 11H-131-206 Validated Immunoassay

Biotinylated anti-VH mAb (M2.3G10.1G06) is diluted in assay buffer (10 mM Tris, 150 mM NaCl, 0.1% BSA, 0.1% Tween20, pH 7.5) and 100 µL added at a final concentration of 10 ng/ml to each well of a Neutravidin-coated plate (Pierce). The plate is sealed and incubated for 1 hour at 37° C.

The microtiter plate is washed 5 times with 300 µL of wash buffer (10 mM Tris, 150 mM NaCl, 0.1% Tween 20, pH 7.5) using a plate washer.

100 µL per well of standards, and samples diluted in matrix are added and the plate sealed and incubated with constant shaking for approximately 2 hours at 37° C.

The microtiter plate is washed 5 times with 300 µL of wash buffer.

100 µL per well of digoxigenin-labelled hTNFR1:Fc (1:40,000) is added and the plate sealed and incubated with constant shaking for approximately 2 hours at 37° C.

The microtiter plate is washed 5 times with 300 µL of wash buffer.

100 µL per well of HRP-labelled mouse anti-digoxigenin antibody (Abcam) (1:20,000) is added and solution, seal with aseptic sealing tape, and the plate sealed and incubated with constant shaking for approximately 2 hours at 37° C.

The microtiter plate is washed 5 times with 300 µL of wash buffer.

100 µL per well of TMB substrate (Thermo) is added and the plate is incubated with constant shaking for approximately 5 minutes at room temperature.

100 µL per well of TMB substrate stop solution (Sigma) is added, and the absorbance at 450 nm for each well is read using a plate reader. The standard curve is fitted fit to a 1/x weighted four parameter logistic algorithm using SMS2000 and the unknown samples are interpolated from the curve.

Example 7c

Ability of DOM1H-131-206 with a C-terminal Alanine Extension (+A) to Inhibit TNFR1 Signal Transduction TNFα signals through the NFκB pathway and results in the secretion of various cytokines including IL-8. In unstimulated cells, IL-8 mRNA is rapidly degraded. However, in the presence of TNFα, activation of the NFκB pathway leads to the stabilisation of IL-8 mRNA. This stabilisation results in an increase in mRNA and contributes to induction of IL-8 secretion. Hence, in this assay induction of secreted IL-8 is to determine whether the addition of a C-terminal extension affects the ability of DOM1H-131-206 or DOM1H-131-206+A (i.e. a C terminal alanine extension) to inhibit TNFR1 signal transduction. These studies were carried out in human and Cynomolgus monkey cell lines, and also in human and Cynomolgus monkey whole blood. Comparison of $IC_{50}$ values indicates that extension of the C-terminus of DOM1H-131-206 which reduced pre-existing ADA binding did not negatively impact the ability of DOM1H-131-206 to inhibit signal transduction via TNFR1 in either human or Cynomolgus monkey cells (Table 6b).

Protocol to Determine Inhibition of TNFα-induced IL-8 in Human Lung Fibroblasts

The ability of DOM1H-131-206 or DOM1H-131-206+A to prevent human TNFα binding to human TNFR1 and to inhibit IL-8 secretion was determined using human lung fibroblast MRC-5 cells (ATCC). MRC-5 cells were incubated with the test samples for one hour after which TNFα (220 pg/ml) was added. Following incubation at 37° C. and 5% $CO_2$ for 24 hours the supernatants were harvested and stored at −20° C. until the MSD™ assay for IL-8 was performed according to the manufacturer's protocol for tissue culture samples. The supernatants were diluted 1 in 12 in the supplied Calibrator Diluent prior to assay. Curve fitting was conducted in GraphPad Prism in order to determine the $IC_{50}$.

Protocol to Determine Inhibition of TNFα-induced IL-8 in A549 Cells

A549 cells were seeded into 96-well plates at a density of $2 \times 10^4$ cells/well and incubated overnight at 37° C. and 5% $CO_2$ to allow adherence. The cells were then incubated for one hour in the presence of DOM1H-131-206 or DOM1H-131-206+A at various concentrations in the range 0.01 nM-1000 nM. Each concentration was tested in duplicate wells. Following incubation at 37° C. and 5% $CO_2$ for 24 hours the supernatants were harvested and stored at −20° C. until the MSD™ assay for IL-8 was performed according to the manufacturer's protocol for tissue culture samples. The supernatants were diluted 1 in 5 in the supplied Calibrator Diluent prior to assay. Curve fits and $IC_{50}$ values were calculated using XLFit.

Protocol to Determine Inhibition of TNFα-induced IL-8 in CYNOM-K1 Cells

CYNOM-K1 cells were incubated for one hour in the presence of DOM1H-131-206 or DOM1H-131-206+A at various concentrations starting at 100 nM. This was followed by stimulation with TNFα at a final concentration of 1 ng/ml. Following incubation at 37° C. and 5% $CO_2$ for 24 hours the supernatants were harvested and stored at −20° C. until the MSD™ assay for IL-8 was performed according to the manufacturer's protocol for tissue culture samples. The supernatants were diluted 1 in 12 in the supplied Calibrator Diluent prior to assay. Curve fitting was conducted in GraphPad Prism order to determine the $IC_{50}$.

Protocol to Determine Inhibition of TNFα-induced IL-8 in Human Whole Blood

Blood from healthy volunteer donors (with appropriate consent compliant with the UK Human Tissue Act) was collected into sodium heparin. Assay medium was prepared by adding 1% BSA to RPMI-1640 media (without phenol red). DOM1H-131-206 or DOM1H-131-206+A and $V_H$ dummy dAb were diluted in 96-well plates in assay medium such that the final concentration after addition of blood would be 800 nM, and serially diluted 1 in 2 down to 0.01 nM. 130 μl of blood was added per well and the plates were incubated for one hour (37° C., 5% $CO_2$) to allow binding to TNFR1. Blood samples were then stimulated with 10 μl of TNFα diluted in assay medium such that the final concentration was 10 ng/ml. Each condition was tested in duplicate. Following a further 24 hours incubation (37° C., 5% $CO_2$), 110 μl of PBS was added per well to increase the volume of the samples, which were then agitated on a plate shaker for 10 minutes at 500 rpm and centrifuged at 1500 rpm for 5 minutes. The plasma was transferred to a new plate and stored at −80° C. until the IL-8 MSD™ assay was performed according to the manufacturer's protocol for serum and plasma samples. Curve fits and $IC_{50}$ values were calculated using XLFit.

Protocol to Determine Inhibition of LPS-induced IL-8 in Whole Blood from Cynomolgus Monkey 12 mls blood from 4 Cynomolgus monkeys was collected into sodium heparin. Assay medium was prepared by adding 1% BSA to RPMI-1640 media (without phenol red). DOM1H-131-206 or DOM1H-131-206+A and $V_H$ dummy dAb were diluted in 96-well plates in assay medium to 15× final concentration. Each concentration was tested in triplicate. 130 μl blood was added per well and the plates were incubated for one hour (37° C., 5% $CO_2$) before stimulation with 10 μl of LPS diluted in assay medium such that the final concentration was 94 ng/ml. The plates were then incubated for a further 24 hrs (37° C., 5% $CO_2$). Following the incubation, 110 μl of PBS was added per well to increase the volume of the samples, which were then agitated on a plate shaker for 10 minutes at 500 rpm and centrifuged at 2000 rpm for 5 minutes. The plasma was transferred to a new plate and stored at −80° C. until the IL-8 was measured using the MSD™ assay for human IL-8 performed according to the manufacturer's protocol for serum and plasma samples. The plasma was undiluted in the assay. Curve fits and $IC_{50}$ values were calculated using XLFit.

TABLE 6b

Summary of the potency of DOM1H-131-206 compared with DOM1H-131-206 + A in human and monkey cell-based assays:

| | $IC_{50}$ (nM) ± Standard Deviation | |
|---|---|---|
| | DOM1H-131-206 | DOM1H-131-206 + A |
| MRCS human lung fibroblast (n = 3) | 4.8 ± 2.4 | 3.5 ± 2.5 |
| A549 human lung epithelium (n = 2) | 1.0 ± 0.23 | 1.0 ± 0.28 |
| CYNOMK1 Cynomolgus monkey skin fibroblasts (n = 2) | 4.8 ± 0.4 | 4.7 ± 0.7 |
| Human whole blood (n = 3-5) | 1.6 ± 1.0 | 0.9 ± 0.3 |
| Cynomolgus monkey whole blood (n = 3) | 0.5 ± 0.4 | 0.4 ± 0.3 |

Example 7d

Use of DOM1h-131-206 Domain Antibody for Treatment of Psoriasis

In these studies, the DOM1h-131-206 domain antibody (having the amino acid sequence shown in SEQ ID NO: 1) was utilized as well as rodent orthologs of this domain antibody. Data obtained with these molecules was used to select the doses and treatment protocols described herein to be used for treatment of psoriasis, and psoriatic plaques, in human patients to be administered either DOM1h-131-206 (having the amino acid sequence shown in SEQ ID NO: 1), or the DOM1h-131-206 ADA fix molecule with a terminal alanine (having the amino acid sequences shown in SEQ ID NO: 16), or a DOM1h131206 ADA fixed molecule comprising any ADA fix (i.e. any modification to decrease binding of a dAb to ADAs) as is disclosed herein.

For example, pharmacokinetics derived from in vivo studies with Cynomolgus monkeys showed the DOM1h-131-206 domain antibody (with the amino acid sequence shown in SEQ ID NO: 1) to have a plasma clearance of 2.4 mL/min/kg, which approximates to the glomerular filtration rate (GFR) in monkeys and gives an elimination half-life of approximately 3 hours. The volume of distribution for this domain antibody was 0.26 L/kg which equates approximately to the extravascular volume and suggested distribution outside of the central/plasma compartment. When the DOM1h-131-206 domain antibody was administered to an extravascular compartment (for example when inhaled into lungs) there is only a small change in the observed elimination half-life which reflects absorption rate limiting kinetics.

Furthermore, following intradermal dosing of a rodent orthologue anti-TNFR1 dAb ("Dom1m-15-12") to mice, an even longer absorption lag was observed. This may have been due to a larger difference between the GFR and absorption rate clearance following dosing via the intradermal route. The observed terminal elimination rate in mouse plasma was approx 40 minutes which was longer than that following intravenous delivery (approx 20 minutes). The slower elimination rate (Ke) seen in plasma following intradermal delivery was corroborated by the dermal tissue PK that showed a terminal elimination rate of 5-7 hours (Ke 0.1-0.14 $h^{-1}$), although the fraction of the dose driving the apparently prolonged elimination rate was estimated to be small (0.5%). Dermal absorption rate (Ka) into plasma was defined from a rat study with intradermal dosing of a rodent ortholog dAb and was relatively rapid (Ka=4.1 $h^{-1}$) resulting in an observed $T_{max}$ at approximately 1 hour post dose. It was estimated that 10% of the domain antibody was retained within the dermal compartment in rat with an assumed elimination rate from the skin similar to mouse. Thus, it appears that following intradermal injection, the DOM1h-131-206 domain antibody distributes to vascularized tissues in the skin (e.g., the dermis) where it is rapidly extracted into plasma and is eliminated via renal filtration. The initial distribution and absorption phase through the tissues of the skin is reflected in the absorption lag time before plasma exposures become measurable. Given the anatomical differences between rodent and human skin, the absorption rate in humans was expected to be longer, which in turn would lead to lower/unmeasurable plasma exposure of the DOM1h-131-206 domain antibody. This means that human plasma exposure predictions are based on observations from rodent studies and therefore serve as a conservative estimate of plasma exposure in humans.

The DOM1h-131-206 domain antibody (having the amino acid sequence shown in SEQ ID NO: 1) was also dosed to healthy volunteers via intravenous infusion (up to 3 hours duration) up to 2 mg/kg and in an ongoing trial via inhalation in healthy volunteers. Derived pharmacokinetic parameters were generally in very good agreement with pre-clinical data in cynomolgus monkeys. Following intravenous administration clearance was between 0.6-1.5 mL/min/kg (GFR in human approx 1.8 mL/min/kg) with a resulting elimination half-life of 5 hours. Volume of distribution, approx 0.3 L/kg, was similar to extravascular volume. Rapid distribution of the DOM1h-131-206 domain antibody into the extravascular compartment was confirmed via a bronchoalveolar lavage measurement (lung epithelial lining fluid) following IV administration. Levels in the lung extravascular fluid were approximately 4-14% of plasma levels measured at 5 hours from start of dosing following a 3 hour infusion.

Predictions of efficacy in humans have been estimated based on the observed and predicted exposure estimates within the dermal compartment and human in vitro cell line data. $IC_{50}$ ranges (8-40 ng/mL) in these in vitro systems (varying complexity and cell type) have been used as target trough levels within the dermal compartment and facilitated selection of the domain antibody doses and treatment protocols for the treatment of psoriasis, and psoriatic plaques, in human patients described here. For example, the starting dose of 0.5 mg was chosen to achieve a plasma exposure, assuming a worst case systemic exposure, lower than those achieved in the FTIH intravenous study were agonism was observed in ADA positive subjects. At this initial starting dose it is expected that TNFR1 mediated signaling is inhibited within a discreet zone around the injection site (<2 cm² surface area) to a level of ≥90% immediately after dosing. TNFR1 inhibition over time is dependent on the amount of drug delivered, retained and then eliminated from the dermal compartment. Assuming a minimum (10% dermal retention and Ke 0.1-0.14 h$^{-1}$ as in rat) it was expected that levels will be maintained ≥$IC_{50}$ (within an injection/test zone) for a minimum of 3 days following an intradermal injection of 0.5 mg of the DOM1h-131-206 domain antibody.

For selection of domain antibody doses and treatment protocols predictions of human plasma exposure following intradermal dosing of the DOM1h-131-206 domain antibody were made. These predictions assumed the maximum possible exposure that could be achieved for an intradermal injection. Actual human plasma concentration-time data from intravenously administered DOM1h-131-206 domain antibody was used in a human dermal PK model with a fixed absorption rate (scaled from rodent dermal absorption) and a bioavailability of 100%. The human plasma concentration-time profile for the maximum domain dose(s) and treatment protocols described here (2 mg weekly+0.5 mg biweekly) was then examined. This revealed predicted peak plasma concentrations reach $T_{max}$ rapidly within 30 min post dose, and levels drop rapidly to levels below the current plasma assay lower limit of quantification (0.1 ng/mL) within 24 hours. No accumulation on repeat dosing was expected in plasma even using this maximum possible exposure prediction. However, this prediction represents the highest possible plasma exposure and it is possible exposures could be significantly lower than predicted and even so low that plasma exposure may not be measurable. Using target levels of inhibition (based on in vitro cell based assays) it was predicted that at $IC_{90}$ (immediately post dose) or $IC_{50}$ (trough) levels in the skin in the treatment protocols described here will be in the range of 30-80 ng/mL or 8-40 n/mL respectively.

Based on the above information the predicted plasma exposures ($C_{max}$ and AUC) for the first dose, maximum daily dose and cumulative dose, over 28 days, is shown in the following Table 6b together with the safety margins over pre-clinical safety.

TABLE 6b

|  |  | Safety Multiple[1] |
|---|---|---|
| First dose—0.5 mg weekly | | |
| $C_{max}$ | 52 ng/mL | 933 |
| $AUC_{(0-48h)}$ | 117 ng · h/mL | 2137 |
| $AUC_{(0-28d)}$ | 464 ng · h/mL | 537 |
| Maximum dose—2 mg weekly + 0.5 mg biweekly | | |
| Cmax | 260 ng/mL | 187 |
| $AUC_{(0-48h)}$ | 583 ng · h/mL | 427 |
| $AUC_{(0-7d)}$ | 700 ng · h/mL | 356 |
| $AUC_{(0-28d)}$ | 2800 ng · h/mL | 89 |

Over 14 day repeat dose cynomologus good laboratory practices toxicology study in male monkeys (20 mg/kg/day) based on male mean (days 1, 4 and 14) exposures ($C_{max}$ and $AUC_{(0-24\ h)}$ of 48.5 ug/mL and 249 ug·h/mL respectively).

Finally, the information presented above from the in vitro studies, in vivo studies and the related analyses was used to select the domain antibody doses and treatment protocols useful in the treatment of psoriasis in human patients.

Administration of the domain antibodies according to a treatment protocol as disclosed herein is useful in the treatment of psoriasis. The efficacy of the domain antibody for treating psoriasis, such as in a particular treatment protocol, can be confirmed by either measurement of plaques with sonography and/or clinical assessments.

Sonographic, high frequency ultrasound based measurements can be performed using a 20 MHz high frequency sonograph (DUB USB, Taberna pro Medicum, Lueneburg). Serial A-scans can be composed and presented on a monitor as a section of the skin. A lateral resolution of approximately 200 μm and an axial resolution of 80 μm are possible and preferred. Dependent on the echo patterns, components of the epidermis, dermis and subcutis are presented and exact measurement of skin thickness is possible. The inflammatory psoriatic infiltrate at the psoriatic plaque site is seen as a clearly definable echo lucent band below the entrance echo. The thickness of the echo lucent psoriatic band can be determined and documented prior to administration of a domain antibody and after administration of a domain antibody. This thickness can be measured in μm. A decrease in thickness of the echolucent psoriatic band after administration of a domain antibody demonstrates administration of a domain antibody, such as according to a treatment protocol disclosed herein, has been efficacious in the treatment of psoriasis, and a psoriatic plaque, in a human patient. See e.g., Bangha et al., 9 Skin Pharmacol. 298 (1996).

Clinical assessment can be performed using a 5-point score determined by comparison in the clinic of a treated psoriatic plaque into which a domain antibody has been injected with at least one untreated plaque near the treated psoriatic plaque. According to this comparison the following clinical assessment scores are assigned (clinical assessment scores are 0 by definition prior to the first administration of a domain antibody):
- −1=worsened
- 0=unchanged (no effect)
- 1=slight improvement
- 2=clearly improvement but not completely healed
- 3=completely healed Thus, on this basis, an increased clinical assessment score after the administration of a domain antibody according to a treatment protocol as disclosed herein indicates efficacy in the treatment of psoriasis, and a psoriatic plaque, in a human patient.

Example 8

Single Alanine Extensions to VHH Clones

ADA binding to VHH was observed using the confirmation assay used in Example 2 (for DOM1H-131-206). In order to confirm that similar inhibition of ADA binding could be achieved by modifying VHH sequences, three VHH clones with amino acid sequences as shown in FIGS. 2 (d), (e) and (f) were tested:

Clone VHH2(d) is a bispecific format, having an IL6R binding module linked by GGGGSGGGS to a human serum albumin binding module as described in WO2010100135. (The amino acid sequence is shown in FIG. 2 d: SEQ ID NO 4)

Clone VHH2(e) is a bispecific format, having TNF binding module linked to a serum albumin binding module in turn linked to a TNF binding module, using GGGGSGGGS as linker as described in WO2010077422. (The amino acid sequence is shown in FIG. 2 e: SEQ ID NO 5)

Clone VHH2(f) is a bivalent mono-specific format comprising two identical modules linked by an Ala-Ala-Ala linker, each module is a dAb which can bind the A1 domain of the Von-Willebrand factor, as shown in WO2009115614A2. (The amino acid sequence is shown in FIG. 2 f: SEQ ID NO 6)

All three clones above were modified by the addition of a C terminal alanine to the end serine residue, and the modified and unmodified clones were compared using the assay of Example 2. As can be seen below in Table 7 and FIG. 4, the results show that C-terminal extension by a single alanine amino acid residue reduces ADA binding.

TABLE 7

| | Sample | | | | | |
|---|---|---|---|---|---|---|
| | VHH2(d) | VHH2(d) + A | VHH2(e) | VHH2(e) + A | VHH2(f) | VHH2(f) + A |
| Mean % Inhibition | 93.23 | 18.86 | 94.93 | 16.95 | 94.15 | 17.46 |

Example 9

Frequency of Healthy Subjects with Pre-existing ADA to a Range of $V_H$ and $V_L$ dAb-based Molecules ADA Assay Procedure Similarly to the procedure described in Example 1 for DOM1H-131-206, test molecules (DOM 1H-131-206 (SEQ ID NO 1), DOM 1H-131-206 +C terminal alanine extension (SEQ ID NO 16), mAb-VH (SEQ ID NO), a Peptide-VL sequence, VH-VL (SEQ ID NO 11), the '735 molecule (SEQ ID NO 30 and 31), were biotinylated, buffer-exchanged and stored in formulation buffer. These test molecules were also ruthenium labelled and then buffer-exchanged and stored in formulation buffer.

The anti-drug antibody (ADA) for each molecule is a bridging assay performed on the MSD™ ECL (electro-chemiluminescence) technology platform as described earlier. The summary of assay procedure used in this experiment is described below:

1. A MSD™ streptavidin plate is blocked with 150 μL/well blocking Casein in PBS (1%) at room temperature (RD for 1-2 hours. The blocker is removed without washing.
2. After a 1 hour pre-incubation, a homogeneous mixture containing 0.1 μg/mL biotinylated test molecule, 0.1 μg/mL ruthenylated ("Sulfo-Tag"™) test molecule, and 2% serum sample in assay diluent (1% Casein in PBS) is transferred to the MSD™ plate and incubated for 1 hour±5 minutes at RT.
3. The MSD plate is then washed 3 times with PBST.
4. 150 μL/well read buffer is added and the plate is read.

The above concentrations and incubation times were used for DOM1H-131-206 molecules.

The skilled person will understand that the precise concentrations and times of incubations will be optimised e.g. the DOM1H-131-206 (and modified versions) may have slightly different concentrations and times of incubations as compared to e.g. a DOM10H-53-567 or a Peptide-VL sequence.

A panel of 100 healthy human donor serum samples was screened for reactivity in the assay. Pre-existing antibodies (ADA) against the variable light chain (Vl), framework were also detected in normal human serum samples, although at lower magnitude and frequency than what was previously observed against $V_H$ and $V_{HH}$ domains (see FIG. 4). The results are shown in FIG. 5 where the Y axis shows levels of binding to ADA s and $V_H$ dAbs had the highest incidence of ADA binding.

Conclusions were: results shown in FIG. 5 show the level of pre-existing ADAs binding to DOM 1H-131-206 and the effect of adding a C terminal extension on binding of the modified DOM 1H-131-206 to ADAs. It can also be observed from FIG. 5 that pre-existing ADAs binding to a VH dAb were also observed when it is fused to a mAb (mAb-VH). FIG. 5 also shows that there are pre-existing ADAs binding to V kappa (Vk) (VL) dAbs and examples shown include peptide:VL, VH-VL fusions and a mAb-VL fusion Example 10

Amino Acid Extensions to the VL Framework

Since pre-existing antibodies against the VL (VK) framework were also detected in normal human serum samples although at a generally lower level than was observed to the VH framework (see FIG. 5), it was determined whether modifications of the C-terminal region of VK dAbs could reduce pre-existing ADA binding, as had been proven for VH containing molecules.

Based on a mAb:linker: $V_L$ molecule (designated '735— this molecule is "mAbdAb"—it is a IL-13mAb:linker:IL-4 (v Kappa) dAb), a panel of test mAb:linker: $V_L$ molecules were generated by standard site-directed mutagenesis, and which contained the same VL dAb sequence, but have various C-terminal modifications to the VL dAb. These test materials designated '15014', '15019', '15020' and '15021' were engineered to have a C-terminal extension (+AAA, +T or +TV), or to have a C-terminal deletion (—R) (shown below in Table 8).

Test materials were assayed using a 'confirmation assay' as described below, similar to that described previously for $V_H$ dAbs. Compound testing was performed by evaluating the ability of individual compounds to compete with labelled assay-specific compounds for binding to pre-existing antibodies. Any potential reductions in assay signal were reported as % inhibition. Percent inhibition levels greater than the previously determined confirmatory cutpoint for that particular assay suggests that the test compound competes with the assay specific compound for binding to anti-VK antibodies, and thus may share epitope(s) with the assay specific compound.

'735 ADA Confirmation Assay Procedure Used for Measuring the Frequency of Pre-existing ADA to V Kappa:
1. In a microtitre assay plate, 2% ADA positive serum sample in assay diluent (1% casein in PBS) is incubated for 1 hour±5 minutes at RT with a final concentration of 10 µg/mL '735 or other test material such as modified dAbs.
2. After the 1 hour pre-incubation, a homogeneous mixture containing 0.05 µg/mL Biotinylated '735 and 0.05 µg/mL ruthenylated ("Sulfo-Tag"™) '735, in assay diluent (1% casein in PBS) is added to the assay plate and incubated overnight at RT.
3. After the incubation, the MSD plate is then washed 3 times with PBST, the assay samples are transferred to the MSD plate, and the plate is incubated for 1 hour±5 minutes in the dark at RT.
4. The MSD™ plate is then washed 3 times with PBST
5. 150 µL/well read buffer is added and the plate is read.

The results of these compound screenings are presented in Table 8. All of the C-terminal modifications tested (+AAA, +T, +TV and —R) showed reduced inhibition in the '735 confirmation assay. This suggests that C-terminal modifications to VL dAbs ablate the binding of pre-existing antibodies (ADAs) in a similar manner to VH dAbs.

TABLE 8

Assessment of ADA binding of mAb: VL '735 mutants

| Clone | Sequence modification (made to the dAb component of the mAbdAb molecule) | % inhibition in confirmation assay (mean value from 7 donor subjects) | % subjects with ADA binding |
|---|---|---|---|
| '735 | Unmodified | 74.92 | 100 |
| 15014 | +AAA | −4.40 | 14.29 |
| 15019 | +T | 12.88 | 14.29 |
| 15020 | +TV | 8.53 | 0 |
| 15021 | −R | 20.08 | 0 |

Example 11

Amino Acid Extensions to the VH Framework of DOM10H-53-567 (Anti-IL-13 dAb)

Since C-terminal modifications to the anti-TNFR1VH dAb DOM 1H-131-206 reduced pre-existing ADA binding, it was determined whether modification of the C-terminus could reduce ADA binding to a different VH molecule. C-terminal modifications were made to the VH framework of DOM10H-53-567 by standard site-directed mutagenesis techniques. Molecules with substitutions (test materials) were assayed using the 'confirmation assay' described previously.

Extension of the C-terminus of DOM10H-53-567 also significantly reduced pre-existing ADA binding (results shown below in Table 9). This is exemplified by extensions A, AS, AST, ASTK, ASTKG and ASTKG. These modifications did not negatively impact the ability of DOM10H-53-567 clones to bind and inhibit its target antigen IL-13 as confirmed by the IL-13 dAb activity assay described below and results shown in Table 9b.

TABLE 9a

Assessment of ADA binding of DOM10H-53-567 mutants

| Parental clone | Sequence modification | % inhibition in confirmation assay (mean value from 10 donor subjects) | % subjects with ADA binding |
|---|---|---|---|
| DOM 10H-53-567 | Unmodified | 95.06 | 100 |
| DOM 10H-53-567 | C-terminal A | 12.84 | 10 |
| DOM 10H-53-567 | C-terminal AS | 14.79 | 10 |
| DOM 10H-53-567 | C-terminal AST | 29.02 | 20 |
| DOM 10H-53-567 | C-terminal ASTK | 27.67 | 20 |
| DOM 10H-53-567 | C-terminal ASTKG | 13.39 | 10 |

IL-13 dAb Activity Assay Protocol:
A bioassay was used to measure the ability of variants of DOM10H-53-567 molecules to inhibit recombinant human IL-13-stimulated alkaline phosphatase production in HEK-Blue-STAT6 cells in vitro. HEK-STAT6 cells (Invivogen) (which express secreted embryonic alkaline phosphatase (SEAP) under the control of a STAT6-dependent promoter) were plated into 96 well plates. Human IL-13 at 3 ng/mL concentration and a dilution series of DOM1-H-53-567 molecules were pre-equilibrated for 1 hour at room temperature and then added to the cells for 24 hours at 37° C. Following incubation, supernatant concentrations of SEAP produced by the cells as a result of IL-13 stimulation, were determined by addition of Quanti-Blue (Invivogen) and obtaining an optical density reading at 640 nm. IC50 values were calculated from the dose response curves using Graphpad Prism.

TABLE 9b

Assessment of activity for DOM10H-53-567 mutants

| Parental Clone | Sequence Modification | Mean IC50 (nM) for inhibition of IL-13 induced SEAP (mean value of between 2 and 4 experiments) |
|---|---|---|
| DOM 10H-53-567 | Unmodified | 0.56 |
| DOM 10H-53-567 | C-terminal A | 0.59 |
| DOM 10H-53-567 | C-terminal AS | 0.56 |
| DOM 10H-53-567 | C-terminal AST | 0.68 |
| DOM 10H-53-567 | C-terminal ASTK | 0.75 |
| DOM 10H-53-567 | C-terminal ASTKG | 0.40 |

Extension of the C-terminus of DOM10H-53-567 which reduced pre-existing ADA binding did not negatively impact the ability of DOM10H-53-567 dAbs to bind and inhibit their target antigen (human IL-13).

Example 12a

Cloning of Anti-VEGF VH/Vk dAb-Fc-dAb Molecules with Modified C-termini

The Vh-Vk dAb-Fc-dAbs with modifications made to the C-terminus of the Vk dAb portion: DMS30047-30054 were engineered by generating the variant Vk dAb sequences by PCR and then by re-cloning into DMS30045 (SEQ ID NO 40) and DMS30046 (SEQ ID NO 41), respectively to generate the modified mammalian expression vectors. From DMS30045: (i) the C-terminal arginine residue was removed to generate DMS30047 (DMS30037-R), (ii) a C-terminal alanine was added to generate DMS30048 (which is DMS30037+A) (SEQ ID NO 43), (iii) three C-terminal alanines were added to generate DMS30049 (DMS30037+AAA) (SEQ ID NO 44), and a C-terminal threonine was added to generate DMS30050 (DMS30037+T) (SEQ ID NO 45). From DMS30046 (SEQ ID NO 41): (i) the C-terminal arginine residue was removed to generate DMS30051 (DMS30038-R) (SEQ ID NO 46), (ii) a C-terminal alanine was added to generate DMS30052 ((DMS30038+A) (SEQ ID NO 47), (iii) three C-terminal alanines were added to generate DMS30053 (DMS30038+AAA) (SEQ ID NO 48), and a C-terminal threonine was added to generate DMS30054 (DMS30038+T) (SEQ ID NO 43).

Descriptions of the molecules above are as follows:

DMS30045: DOM15-26-597 dAb N-(VEPKSSDK linker) & C-terminal K-044-085 dAb ((TGLDSP)×4), DMS30046: DMS1576 with C-terminal K-044-085 dAb ((TGLDSP)×4), DMS30047 (contains modified C terminus): DOM15-26-597 dAb N-(VEPKSSDK linker) & C-terminal K-044-085 dAb minus C-term R ((TGLDSP)×4), DMS30048 (contains modified C terminus): DOM15-26-597 dAb N-(VEPKSSDK linker) & C-terminal K-044-085 dAb+A ((TGLDSP)×4), DMS30049 (contains modified C terminus): DOM15-26-597 dAb N-(VEPKSSDK linker) & C-terminal K-044-085 dAb +AAA ((TGLDSP)×4), DMS30050 (contains modified C terminus): DOM15-26-597 dAb N-(VEPKSSDK linker) & C-terminal K-044-085 dAb +T ((TGLDSP)×4), DMS30051 (contains modified C terminus): DMS1576 with C-terminal K-044085 dAb minus C-term R ((TGLDSP)×4), DMS30052 (contains modified C terminus): DMS1576 with C-terminal K-044-085 dAb +A ((TGLDSP)×4), DMS30053 (contains modified C terminus): DMS1576 with C-terminal K-044-085 dAb +AAA ((TGLDSP)×4), DMS30054 (contains modified C terminus): DMS1576 with C-terminal K-044-085 dAb +T ((TGLDSP)×4) (amino acid sequences of the molecules are shown in FIG. 12 and SEQ ID NO 40-49).

Example 12B

Modifications to the C-Terminal Region of the VEGF $V_K$ dAb Dumbbell Molecules DMS30037 and DMS30038 have Reduced Binding to Pre-existing Antibodies V Kappa ADA Confirmation Assay Procedure Used for Measuring the Frequency of Pre-existing ADA to V Kappa:

1. In a microtitre assay plate, 10% ADA positive serum sample in assay diluent (1% casein in PBS) is incubated for 1 hour±5 minutes at RT with a final concentration of 10 μg/mL of the test material such as modified dAbs.
2. After the 1 hour pre-incubation, The ADA positive serum/test material is added to an assay plate with a homogeneous mixture containing Biotinylated V kappa dAb (unmodified) and ruthenylated ("Sulfo-Tag"™) 'V kappa dAb (unmodified) for a final concentration of about 0.025 μg/mL Biotinylated dAb, about 0.0125 μg/mL ruthenylated ("Sulfo-Tag"™) dAb, and 5% ADA positive serum in assay diluent (1% casein in PBS). The plate is incubated for 1 hour±5 minutes at RT.
3. A MSD™ streptavidin plate is blocked with 150 μL/well blocking casein in PBS (1%) at room temperature (RD for 1-2 hours. The blocker is removed without washing.
4. After the 1 hour pre-incubation, the homogeneous mixture is added to an MSD™ streptavidin assay plate and incubated for 1 hour±5 minutes at RT.
5. After the 1 hour incubation, the MSD plate is then washed 3 times with PBST, the assay samples are transferred to the MSD plate, and the plate is incubated for 1 hour±5 minutes in the dark at RT.
6. The MSD™. plate is then washed 3 times with PBST
7. 150 μL/well read buffer is added and the plate is read.

The skilled person will understand that the precise concentrations and times of incubations in the confirmation assays will be optimised e.g. the 1H-131-206 (and modified versions) may have slightly different concentrations and times of incubations as compared to a DOM10H-53-567.

The results of these compound screenings are presented in Table 9B below. All of the C-terminal modifications tested on the V kappa dAbs (+T, +A, +AAA and −R) showed reduced inhibition in the above '697 confirmation assay. This suggests that C-terminal modifications to these V kappa dAbs reduce the binding of pre-existing antibodies (ADAs) in a similar manner to Vh dAbs.

TABLE 9b

Assessment of ADA binding of DMS3007 and DMS3008 mutants

| Parental clone | Sequence modification | Mean % inhibition of signal in confirmation assay (mean value-of 6 subjects) | % subjects with ADA binding (mean value-of 6 subjects) |
|---|---|---|---|
| DMS30037 | Unmodified | 60.46 | 100 |
| DMS30050 | C-terminal T addition | 20.97 | 16.67 |
| DMS30048 | C-terminal A addition | 12.86 | 16.67 |
| DMS30049 | C-terminal AAA addition | 8.36 | 16.67 |
| DMS30047 | C-terminal −R deletion | 6.17 | 16.67 |
| DMS30038 | Unmodified | 70.65 | 100 |
| DMS30054 | C-terminal T addition | 14.66 | 16.67 |
| DMS30051 | C-terminal −R deletion | −5.91 | 16.67 |

Example 13

Expression of Anti-VEGF VH/Vk dAb-Fc-dAb Molecules with Modified C-termini (DMS30047-30054)

Expression plasmids encoding the relevant anti-VEGF dAb-Fc-dAb molecules described above in Example 12a were transiently transfected into HEK293 6E cells and expressed at 500 ml scale to produce the antibody fragment molecules using the method described below in this example. Expression levels of >30 mg/L supernatant were routinely achieved.

The dAb sequences were cloned onto the N- or C-terminus of a generic Fc of the human IgG1 isotype in a mammalian expression vector. The dAbs were linked to the Fc using a linker sequence: the N-terminal linker was either AAAS, or TVAAPS and the C-terminal linker was either ((GS(TVAAPSGS)×3), or Albumin Domain 3.

Example 14

Purification of Anti-VEGF VH/Vk dAb-Fc-dAb Molecules with Modified C-termini

The dAb-Fc-dAb molecules were affinity purified from the supernatants, as described for the Example above.

Example 15

Molecular Analysis by Size-Exclusion Chromatography (SEC) of Anti-VEGF Vh/Vk dAb-Fc-dAb Molecules with Modified C-termini The molecular integrity, homogeneity and % purity of the anti-VEGF dAb-Fc-dAb molecules which had been purified were then analysed by SDS-PAGE and analytical size-exclusion chromatography (SEC). The proteins were thus confirmed to be >95% pure target protein by SDS-PAGE and SEC prior to further analysis in biology assays.

Example 16

Binding of Anti-VEGF Vh/Vk dAb-Fc-dAb Molecules with Modified C-termini to VEGF on Biacore The binding affinity of certain anti-VEGF dAb-Fc-dAb molecules, (with small C-terminal modifications), for $VEGF_{165}$ was determined by Surface Plasmon resonance (SPR) using a Biacore T100. Protein A was immobilised on a C1 chip by primary amine coupling and this surface was then used to capture the anti-VEGF constructs. Human recombinant $VEGF_{165}$ (sourced 'in house' from transient transfection of HEK293 cells) was used as the analyte at 32 nM to 0.03125 nM in a 4 fold dilution series. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer. The data obtained is shown in Tables 10A, 10B & 10C. From the data in Table 10A, the behaviour of DMS30037 and several variants modified at the C-terminus: DMS30037+A (DMS30048), DMS30037+AAA (DMS30049), and DMS30037+T (DMS30050) (see Example 12a for further details of these molecules) seems comparable on Biacore and the C-terminal modifications do not appear to reduce potency over parental.

A further data set is shown in Table 10B where the performance of both DMS30037 and DMS30038 were compared with variants modified at the C-terminus: DMS30037-R, (labelled as +R (DMS30047), DMS30037+T (DMS30050) and DMS30038-R, (labelled as +R (DMS30051) and Bevacizumab (Avastin) in the Biacore. In this data set again the behaviour of all the molecules seems comparable on Biacore and the C-terminal modifications do not appear to reduce potency over parental. Meaningful data could not be captured other than to view the curve for Avastin. A further data set is displayed in Table 10C where the molecules DMS30037 and DMS30038 were compared with variants modified at the C-terminus: DMS30037-R, (DMS30047), DMS30037+T (DMS30050), DMS30038-R, (DMS30051) and DMS30038+T (DMS30054) and Bevacizumab (Avastin). Again the behaviour of all the dAb-Fc-dAb molecules seem comparable on Biacore and the C-terminal modifications do not appear to reduce potency over parental. In this data set, see Table 10C, the Bevacizumab (Avastin) data could not be properly measured due to the off-rate being too tight.

Example 17

VEGF R2 Receptor Binding Assay of Anti-VEGF Vh/Vk dAb-Fc-dAb Molecules with Modified C-termini The potencies of anti-VEGF_Vh/Vk dAb-Fc-dAb molecules based upon DMS30037 and DMS30038, but with C-terminal modifications, were compared both to the wild type molecule and Bevacizumab (Avastin), in the VEGF receptor 2, (R2), binding assay using the modified method, i.e. with no pre-incubation, as described below in this example. The data is shown in Table 11A, all the tested dAb-Fc-dAb molecules: DMS30037, DMS30037+T (DMS30050), DMS30037-R (DMS30047), DMS30038, DMS30038-R (DMS30051), appeared to be of comparable potency and considerably more potent than Bevacizumab (Avastin), Table 11A. There was little variation in the maximal percentage inhibition achieved by the molecules in the assay with all molecules achieving >93-98% maximal inhibition, (data not shown).

Further data was generated comparing the dAb-Fc-dAbs: DMS30038, DMS30038+T, (DMS30050) and DMS30038-R, (DMS30051) with Bevacizumab (Avastin), in the same assay format, the data is displayed in Table 11B. From the data DMS30038 and its C-terminal variants, (Table 11B), have similar potencies judged by EC50 values in the RBA assay and appear to be considerably more potent than Bevacizumab (Avastin) by this criteria. There was little variation in the maximal percentage inhibition achieved by the molecules in the assay with all molecules achieving >94% maximal inhibition, (data not shown).

VEGF R2 Receptor Binding Assay: The potencies were analysed in the VEGF receptor binding assay in comparison to that of Bevacizumab (Avastin). This assay measures the binding of VEGF165 to either VEGF R1 or VEGF R2 and the ability of the test molecules to block this interaction. A MSD standard bind 96 well plate (L11XA-3) was coated with 0.25 µg/ml VEGF R1 (R&D Systems 321-FL) or VEGF R2 (R&D 357-KD) in bicarbonate buffer (50 µl/well), covered with a plate sealer and incubated overnight at 4° C. The next day the MSD plate was washed 3×300 µl/well with Tris wash buffer and blotted over a pad of tissue to remove excess wash buffer from the wells. The MSD plate was then blocked with 3% BSA in PBS (250 µl/well) and incubated shaking (750 RPM) at room temperature for 1 hour. The MSD plate was washed again before the addition of a 2×concentration of anti-VEGF molecule (25 µl/well) and incubated with shaking (750 RPM) at room temperature for 10 minutes before the addition of a 2× concentration of rhVEGF, 25 µl/well, R&D Systems (293-VE/CF, made in insect cells using Baculovirus) or a GSK 'in house' source of VEGF (made from HEK293 mammalian cells, latter data not shown except Table 3A). The anti-VEGF molecules and the VEGF were prepared using 0.1% BSA in PBS. The initial assay was performed with a step in which the anti-VEGF molecule was pre-incubated with VEGF. The pre-incubations were prepared by adding an equal volume of a 2×concentration of anti-VEGF molecule to an equal volume of a 2×concentration of VEGF (R&D, 293-VE/CF) for 30 minutes at room temperature. The final VEGF concentration used was 10 ng/ml. No VEGF and VEGF alone controls were also included. The MSD plate was incubated with shaking (750 RPM) at room temperature for 2 hours after which it was washed again before the addition of the detection reagent (50 µL/well, goat anti-human VEGF biotinylated antibody—R&D Systems BAF293) at 0.25 µg/ml in 1% BSA in PBS and incubated with shaking (750 RPM) at room temperature for 1 hour. The MSD plate was washed again before the addition of the streptavidin sulfo-TAG (50 µl/well, MSD R32AD-1) at 2 pg/ml in 1% BSA in PBS and incubated with shaking (750 RPM) at room temperature for 30 minutes. Prior to measurement of the electrochemiluminescence in a MSD Sector Imager 6000, the MSD plate was washed and 150 µl/well of 2×Read Buffer T (MSD R92TC-1) was added. Curve fitting and EC50 calculations were performed using GraphPad Prism. The ability of the test anti-VEGF molecules and Bevacizumab (Avastin) to inhibit VEGF binding to VEGFR1 and VEGFR2 was determined as described. Modified method: A second assay was performed whereby the anti-VEGF agent and the VEGF were not pre-incubated prior to the addition to the VEGF Receptor coated MSD plate. This assay was carried out and only used VEGF sourced from R&D Systems, (293-VE/CF). The ability of the anti-VEGF molecules and Bevacizumab (Avastin) to inhibit VEGF binding to VEGFR1 and VEGFR2 was determined as described above but without the pre-incubation step Example 18

Human Umbilical Vein Endothelial Cell (HUVEC) Proliferation Assay: Inhibition with Anti-VEGF Vh/Vk dAb-Fc-dAb Molecules Containing C-terminal Modifications The abilities of dAb-Fc-dAb molecules based upon DMS30037 and DMS30038 but with C-terminal modifications: DMS30037-R (DMS30047) & DMS30037+T (DMS30050), DMS30038-R (DMS30051) & DMS30038+T (DMS30054) to suppress proliferation of human umbilical vein endothelial cells were compared to Bevacizumab (Avastin) using the method described below with the following deviations (i) rather than leaving the outer wells free of cells, the whole 96 well plate was used and (ii) the data was analysed using GraphPad Prism using a Sigmodial curve fit, variable slope cf a non-linear regression (variable slope). The test compounds were independently assessed on individual plates against the comparator molecule, Bevacizumab (Avastin); the assay was carried out on at least three separate occasions, with a total data set per molecule of Bevacizumab (Avastin): 15; DMS30037: 7; DMS30038: 8; DMS30037-R (DMS30047): 3; DMS30037+T (DMS30050): 4; DMS30038-R (DMS30051): 4 & DMS30038+T (DMS30054): 4, (data not shown). The focus was upon analysing both the degree of maximum inhibition and the relative EC50 values in the assay generated by certain molecules compared to that of Bevacizumab (Avastin).

The data was analysed using GraphPad Prism using a Sigmodial curve fit, variable slope cf a non-linear regression (variable slope). Individual curve fits were fitted for each molecule and at each day. Due to some poor fitting, it was decided to introduce constraints for the curve where a plateau was not observed at the lower concentration. One plate was excluded from the analysis due to poor curve fitting despite constraints. This constraint would be equal to the mean of the points at the lowest concentration. Data was manually selected as to whether the minimum was constrained or not, and the curve fit and parameters were automatically updated based upon this criteria selection. Estimates of the curve maxima and the standard error were analysed using a weighted mixed model analysis of variance, using $1/(\text{standard error})^2$, $[SE]^2$, as a weighting. The analysis adjusted for variability between plates and days using random effects terms. From this analysis, the predicted means were estimated and comparisons were made back to Avastin (control) (See Table 12A). The same analysis was then performed on the log 10 scale for the 1050, and the results back transformed. From this, estimates of the geometric means were generated and comparisons were made back to Avastin in the form of a ratio to Avastin (control) i.e. a ratio of 0.5 would indicate a 50% drop from Avastin (See Table 12B).

Human Umbilical Cord Endothelial Cell (HUVEC) Proliferation Assay:

Anti-VEGF molecules were assayed for their ability to suppress proliferation of human umbilical vein endothelial cells compared to that of Bevacizumab (Avastin). This assay measures the extent of endothelial cell proliferation induced by a defined concentration of $VEGF_{165}$ and the ability of VEGF antagonists to block this effect. HUVECs were seeded at 5000 cells per well in 96-well gelatine-coated plates, leaving outer wells free of cells, and incubated for several hours to permit adherence. Test molecules were assayed at equimolar concentrations (max $3.33 \times 10^{-08}$ M)

with a 2-fold serial dilution, each in triplicate. The $VEGF_{165}$ was prepared in basal medium to achieve 75 ng/ml final concentration. Medium was removed manually from the cell monolayers and 50 μl basal media was added to prevent the cells from drying out. 25 μl $VEGF_{165}$-containing medium and 25 μl basal medium or test antibody-containing medium was added as appropriate. Cells were incubated for 72 hrs, after which time the total number of cells was determined using Cell Titre Glo. Treatment of HUVECs with $VEGF_{165}$ resulted in the expected increase in the total number of cells after 72 hrs, when compared with $VEGF_{165}$-untreated cells (data not shown). This VEGF-mediated increase is interpreted as representing the cumulative effects of VEGF on both HUVEC proliferation and prevention of HUVEC cell death. The test compounds were independently assessed on individual plates against the comparator molecule, Bevacizumab (Avastin).

TABLE 12A

Predicted geometric means of maximum percentage inhibition of C-terminally modified anti-VEGF dAb-Fc-dAbs with 95% confidence intervals (CI) compared to parental and Bevacizumab (Avastin) in the HUVEC Assay: Predicted Means for Max % Inhibition

| mAb | Estimate | Lower 95% CI | Upper 95% CI |
| --- | --- | --- | --- |
| Avastin | 71.0316 | 61.6741 | 80.3891 |
| DMS30037 | 85.4759 | 74.9164 | 96.0354 |
| DMS30037 + T | 89.9852 | 78.2698 | 101.70 |
| DMS30037 − R | 82.2693 | 69.9929 | 94.5457 |
| DMS30038 | 73.5602 | 63.7180 | 83.4023 |
| DMS30038 + T | 79.0343 | 67.1904 | 90.8782 |
| DMS30038 − R | 77.6519 | 65.5487 | 89.7550 |

From this analysis, molecules DMS30037, DMS30037+T and DMS30037-R seem to lead to the most maximal inhibition in the HUVEC assay and they out-performed the Avastin group, the confidence interval did not overlap the zero reference so the data was statistically significant from that of Avastin, data not shown (see Table 12A).

TABLE 12B

Geometric means of IC50 for C-terminally modified anti-VEGF dAb-Fc-dAbs with 95% confidence intervals (CI) compared to parental and Bevacizumab (Avastin) in the HUVEC Assay: Geometric Means for IC50

| mAb | Estimate | Lower 95% CI | Upper 95% CI |
| --- | --- | --- | --- |
| Avastin | 3.829E−9 | 3.119E−9 | 4.7E−9 |
| DMS30037 | 1.903E−9 | 1.473E−9 | 2.46E−9 |
| DMS30037 + T | 2.332E−9 | 1.758E−9 | 3.092E−9 |
| DMS30037 − R | 7.365E−9 | 2.06E−10 | 2.639E−7 |
| DMS30038 | 2.163E−9 | 1.723E−9 | 2.715E−9 |
| DMS30038 + T | 2.649E−9 | 1.877E−9 | 3.738E−9 |
| DMS30038 − R | 2.234E−9 | 1.699E−9 | 2.936E−9 |

A similar analysis of the geometric means of the IC50 values with 95% confidence intervals, (CI), showed that almost all the dAb-Fc-dAb molecules DMS30037, DMS30037+T, DMS30038, DMS30038+T and DMS30038-R had statistically significantly lower IC50 values than Avastin, data not shown (see Table 18B). The data set from DMS30037-R was highly variable with a low n number (3).

Overall the data suggest that C-terminal modifications to both dAb-Fc-dAbs: DMS30037 & DMS30038 have very similar $IC_{50}$ values and levels of maximal inhibition in the HUVEC assay to parental molecules and appear more potent, than Bevacizumab (Avastin), both in terms of maximal percentage inhibition and lower $IC_{50}$, (see Tables 12A and 12B).

Example 19 (Tool mAb)

The Use of an Anti-VH mAb to Define the Epitope for Binding of Pre-existing Anti-VH ADA A monoclonal antibody (anti-VH mAb M2.3G10.1G06) binds to the VH framework of DOM1H-131-206 and it was determined that this mAb has much reduced binding to DOM1H-131-206 +A; therefore this antibody appears to bind a similar epitope to the pre-existing human anti-VH ADA.

CDR Sequences of Anti-VH mAb M2.3G10.1G06: The CDR sequences of the anti-VH mAb M2.3G10.1G06 were amplified and sequenced from the hybridoma cell line. The heavy and light chain sequences for mAb M2.3G10.1G06 are shown in [the amino acid sequences are shown in FIGS. 6a and 6b]. Sequences were cloned into a human IgG1 mAb expression vector and transfected into mammalian cells to express the identified mAb. The resulting antibody was purified from the cell supernatant and tested for its ability to bind the VH dAb framework.

Specificity of Anti-VH mAb M2.3G10.1G06: The specificity of mAb M2.3G10.1G06 for binding to the VH dAb framework (with or without a modification which abrogates pre-existing ADA binding) was determined by measuring binding of mAb M2.3G10.1G06 in a TNFR1:dAb binding assay performed on the MSD™ platform (see Example 1 for details of MSD™ platform). The TNFR1:dAb binding assay is detailed below. It was demonstrated that ruthenylated anti-VH mAb M2.3G10.1G06 has a reduced binding to the VH framework by up to 85% when the C-terminus is modified by extension with alanine (1 to 15% residual binding) (results shown in Table 13).

Competition Between Pre-existing Anti-VH ADA and mAb M2.3G10.1G06: To confirm that anti-VH mAb M2.3G10.1G06 binds the same epitope as pre-existing serum anti-VH ADA, a competition assay was carried out. It was determined that serum from a range of human donors with pre-existing anti-VH ADA could compete with anti-VH mAb M2.3G10.1G06 for binding to DOM1H-131-206 (data shown in FIG. 7). We conclude that pre-existing human anti-VH ADA and anti-VH mAb M2.3G10.1G06 share an overlapping epitope on the VH framework.

Modifications to VH dAbs which disrupt the epitope for pre-existing ADA binding may be predicted based on the binding of anti-VH mAb M2.3G10.1G06. The binding of anti-VH mAb M2.3G10.1G06 can therefore be used to assay for modifications which lead to reduced pre-existing ADA binding.

Methods Used:
TNFR1:dAb Binding Assay Protocol
1. TNFR1:Fc is captured onto a hi-bind MSD plate overnight at 4° C. The MSD plate is then washed 3 times with MSD/TRIS wash buffer.
2. The plate is blocked with 3% BSA in PBS for 1.5 hours at room temperature. The MSD plate is then washed 3 times with MSD/TRIS wash buffer.
3. The dilutions series of the test dAb (DOM 1H-131-206 (SEQ ID NO 1) or DOM 1H-131-206 with a C terminal alanine extension (SEQ ID NO 16)) is added for 2 h at RT. The MSD plate is then washed 3 times with MSD/TRIS wash buffer.

4. Ruthenylated mAb M2.3G10.1G06 at a final concentration of 1 µg/ml is added for 1 hour at room temperature. The MSD plate is then washed 3 times with MSD/TRIS wash buffer.

5. 150 µL/well read buffer is added and the plate is read.

Competition Assay Protocol for Pre-existing Anti-VH ADA and mAb M2.3G10.1G06

1. 0.2 µg/mL biotinylated test molecule (dAb) which was DOM 1H-131-206 (SEQ ID NO 1) and 20% serum sample in assay diluent (1% Casein in PBS) are incubated in a round-bottom assay plate for 1 hour±5 minutes at RT.
2. Ruthenylated anti-VH mAb M2.3G10.1G06 at a final concentration of 0.5 µg/mL is added for 1 hour at room temperature.
3. A MSD™ streptavidin plate is blocked with 150 µL/well blocking Casein in PBS (1%) at room temperature (RT) for 1-2 hours.
4. Samples are transferred to the MSD™ streptavidin plate and incubated at room temperature (RT) for 1-2 hours.
5. The MSD plate is then washed 3 times with PBST.
6. 150 µL/well read buffer is added and the plate is read.

TABLE 13

Differential binding of anti-VH mAb to DOM1H-131-206 or DOM1H-131-206 modified with a C-terminal extension

| Test dAb concentration (pg/mL) | Binding assay signal Mean ECL value ± SD | | Relative binding to DOM1H131- 206 + C-Terminal A (%) |
|---|---|---|---|
| | DOM1H- 131-206 | DOM1H- 131-206 + C-terminal A | |
| 270000 | 1168024 ± 3643 | 81489 ± 4537 | 7 |
| 90000 | 1078743 ± 17931 | 66020 ± 3207 | 6 |
| 30000 | 377493 ± 9653 | 11300 ± 266 | 3 |
| 10000 | 108173 ± 3413 | 1507 ± 69 | 1 |
| 3333 | 34479 ± 1397 | 743 ± 14 | 2 |
| 1111 | 12026 ± 243 | 847 ± 226 | 7 |
| 370 | 4387 ± 41 | 669 ± 13 | 15 |
| 0 | 623 ± 2 | 621 ± 5 | |

This mAb binds the framework of VH dAbs e.g. DOM 1H-131-206 (SEQ ID NO 1), but binding is highly reduced in dAbs with a +A C-terminal modification e.g. DOM 1H-131-206 with a C terminal alanine extension (SEQ ID NO 16). H & L chain sequences have been determined from the hybridoma deposited in Biocat. There was only one LC sequence but two HC sequences: one functional (see below) and one non-functional sequence including stop codons and frameshifts.

Expression of the mAb and confirmation of binding against the two molecules above based on the predicted functional sequence below will allow us to confirm that we have the correct mAb sequence for the filing. The way the pTT5 constructs were assembled means that only the sequence in non-italic is from the hybridoma, the italic is chimeric from the pTT vector it was cloned into (this is not required for the binding assay).

Light Chain

DIVIATQSQKFIASPTVGDRVSITCKASQNVGTAVAWYQQKPGQSPKLLI

YSASNRYTGVPDRFTGSGSGMFTLTINNMQSEDLADYFCQQYGSYPLTFG

GGTKLEIKRT*VAAPSVFIFPPSDEQLKSGTASWCUNNFYPREAKVQWKVD*

*NALQSGNSQESVTEQDSKDSTYSLSSTLTLSICADYEKHKVYACEVTHQG*

*LSSPVTIGFNRGEC*

Heavy Chain

EVQLQQSGPVLVKPGASVKMSCKASGYTLTESYMHVVVKQSHGKSLEWIG

VISPYNGGTSYNQKFKDKATLTVDKSSSTAYMELNSLTSEDSAVYYCTRR

GIYYDPSWFAYWGQGTLVTVSAAKTTP*PSVFPLAPSSKSTSGGTAALGCL*

*VKDYFPEPVTVSWNSGALTSGVHTFPAVLQSSGLYSLSSVVTVPSSSLGT*

*QTYICNVNHKPSNTKVDKKVEPKSCDKTHTCPPCPAPELLGGPSVFLFPP*

*KPKDTLMISRTPEVTCVWDVSHEDPEVKFNWYVDGVEVHNAKTKPREEQY*

*NSTYRWSVLTVLHQDWLNGKEYKCKVSNKALPAPIEKTISKAKGQPREPQ*

*VYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGK*

Variable region in normal type.
CDRs underlined/bold
Chimeric sequence for Fc in italics.
Fc is human IgG1.
Sequences for the Tool mAb are shown in FIG. 6 (SEQ ID NOs 14 and 15).

The material in the ASCII text file named "PB64743NatlSeqList.txt," created on Feb. 6, 2014 and having a size of 115,737 bytes is incorporated herein by reference in its entirety.

The invention claimed is:

1. A single immunoglobulin variable domain comprising the amino acid sequence shown in SEQ ID NO: 16.

2. A pharmaceutical composition comprising a single immunoglobulin variable domain according to claim 1 and a pharmaceutically or physiologically acceptable carrier, excipient or diluent.

3. An injectable, oral, inhalable, nebulisable, sustained release or freeze dried formulation which comprises a single immunoglobulin variable domain according to claim 1.

4. A single immunoglobulin variable domain consisting of the amino acid sequence shown in SEQ ID NO: 16.

5. A pharmaceutical composition comprising a single immunoglobulin variable domain according to claim 4 and a pharmaceutically or physiologically acceptable carrier, excipient or diluent.

6. An injectable, oral, inhalable, nebulisable, sustained release or freeze dried formulation which comprises a single immunoglobulin variable domain according to claim 4.

* * * * *

SEQUENCE LISTING

<160> NUMBER OF SEQ ID NOS: 53

<210> SEQ ID NO 1
<211> LENGTH: 119
<212> TYPE: PRT
<213> ORGANISM: Artificial Sequence
<220> FEATURE:
<223> OTHER INFORMATION: Unmodified dAb DOM 1H-131-206 (anti-TNFR1)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu

```
                20                  25                  30
Thr Met Val Trp Val Arg Gln Ala Pro Gly Lys Gly Leu Glu Trp Val
             35                  40                  45

Ser His Ile Pro Pro Asp Gly Gln Asp Pro Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 2
<211> LENGTH: 119
<212> TYPE: PRT
<213> ORGANISM: Artificial Sequence
<220> FEATURE:
<223> OTHER INFORMATION: Unmodified dAb DOM 1H-131-511 (anti-TNFR1)

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
             35                  40                  45

Ser His Ile Pro Pro Val Gly Gln Asp Pro Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 3
<211> LENGTH: 119
<212> TYPE: PRT
<213> ORGANISM: Artificial Sequence
<220> FEATURE:
<223> OTHER INFORMATION: Unmodified dAb DOM 1H-131-202 (anti-TNFR1)

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
             35                  40                  45

Ser His Ile Pro Pro Asp Gly Gln Asp Pro Phe Tyr Ala Asp Ser Val
         50                  55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                    85                  90                  95

Ala Leu Leu Pro Lys Arg Gly Pro Trp Phe Asp Tyr Trp Gly Gln Gly
                100                 105                 110

Thr Leu Val Thr Val Ser Ser
        115

<210> SEQ ID NO 4
<211> LENGTH: 245
<212> TYPE: PRT
<213> ORGANISM: Artificial Sequence
<220> FEATURE:
<223> OTHER INFORMATION: VHH2

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly Gly
            115                 120                 125

Gly Ser Glu Val Gln Leu Val Glu Ser Gly Gly Gly Leu Val Gln Pro
        130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
        210                 215                 220

Tyr Cys Thr Ile Gly Gly Ser Leu Ser Arg Ser Ser Gln Gly Thr Leu
225                 230                 235                 240

Val Thr Val Ser Ser
            245

<210> SEQ ID NO 5
<211> LENGTH: 363
<212> TYPE: PRT
<213> ORGANISM: Artificial Sequence
<220> FEATURE:
<223> OTHER INFORMATION: VHH2

<400> SEQUENCE: 5

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
         20                  25                  30

Trp Met Tyr Trp Val Arg Gln Ala Pro Gly Lys Gly Leu Glu Trp Val
         35                  40                  45

Ser Glu Ile Asn Thr Asn Gly Leu Ile Thr Lys Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
             85                  90                  95

Ala Arg Ser Pro Ser Gly Phe Asn Arg Gly Gln Gly Thr Leu Val Thr
             100                 105                 110

Val Ser Ser Gly Gly Gly Gly Ser Gly Gly Gly Ser Glu Val Gln Leu
         115                 120                 125

Val Glu Ser Gly Gly Gly Leu Val Gln Pro Gly Asn Ser Leu Arg Leu
 130                 135                 140

Ser Cys Ala Ala Ser Gly Phe Thr Phe Ser Ser Phe Gly Met Ser Trp
145                 150                 155                 160

Val Arg Gln Ala Pro Gly Lys Gly Leu Glu Trp Val Ser Ser Ile Ser
             165                 170                 175

Gly Ser Gly Ser Asp Thr Leu Tyr Ala Asp Ser Val Lys Gly Arg Phe
             180                 185                 190

Thr Ile Ser Arg Asp Asn Ala Lys Thr Thr Leu Tyr Leu Gln Met Asn
             195                 200                 205

Ser Leu Arg Pro Glu Asp Thr Ala Val Tyr Tyr Cys Thr Ile Gly Gly
         210                 215                 220

Ser Leu Ser Arg Ser Ser Gln Gly Thr Leu Val Thr Val Ser Ser Gly
225                 230                 235                 240

Gly Gly Ser Gly Gly Gly Ser Glu Val Gln Leu Val Glu Ser Gly
                 245                 250                 255

Gly Gly Leu Val Gln Pro Gly Gly Ser Leu Arg Leu Ser Cys Ala Ala
         260                 265                 270

Ser Gly Phe Thr Phe Ser Asp Tyr Trp Met Tyr Trp Val Arg Gln Ala
         275                 280                 285

Pro Gly Lys Gly Leu Glu Trp Val Ser Glu Ile Asn Thr Asn Gly Leu
         290                 295                 300

Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Arg Pro
                 325                 330                 335

Glu Asp Thr Ala Val Tyr Tyr Cys Ala Arg Ser Pro Ser Gly Phe Asn
             340                 345                 350

Arg Gly Gln Gly Thr Leu Val Thr Val Ser Ser
         355                 360
```

<210> SEQ ID NO 6
<211> LENGTH: 259
<212> TYPE: PRT
<213> ORGANISM: Artificial Sequence
<220> FEATURE:
<223> OTHER INFORMATION: VHH2

<400> SEQUENCE: 6

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 7
<211> LENGTH: 364
<212> TYPE: PRT
<213> ORGANISM: Artificial Sequence
<220> FEATURE:
<223> OTHER INFORMATION: VHH2

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Ser Pro Ser Gly Phe Asn Arg Gly Gln Gly Thr Leu Val Thr
            100                 105                 110

Val Ser Ser Gly Gly Gly Ser Gly Gly Ser Glu Val Gln Leu
        115                 120                 125

Val Glu Ser Gly Gly Gly Leu Val Gln Pro Gly Asn Ser Leu Arg Leu
130                 135                 140

Ser Cys Ala Ala Ser Gly Phe Thr Phe Ser Ser Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Ser Asp Thr Leu Tyr Ala Asp Ser Val Lys Gly Arg Phe
                180                 185                 190

Thr Ile Ser Arg Asp Asn Ala Lys Thr Thr Leu Tyr Leu Gln Met Asn
            195                 200                 205

Ser Leu Arg Pro Glu Asp Thr Ala Val Tyr Tyr Cys Thr Ile Gly Gly
        210                 215                 220

Ser Leu Ser Arg Ser Ser Gln Gly Thr Leu Val Thr Val Ser Ser Gly
225                 230                 235                 240

Gly Gly Gly Ser Gly Gly Gly Ser Glu Val Gln Leu Val Glu Ser Gly
                245                 250                 255

Gly Gly Leu Val Gln Pro Gly Gly Ser Leu Arg Leu Ser Cys Ala Ala
            260                 265                 270

Ser Gly Phe Thr Phe Ser Asp Tyr Trp Met Tyr Trp Val Arg Gln Ala
        275                 280                 285

Pro Gly Lys Gly Leu Glu Trp Val Ser Glu Ile Asn Thr Asn Gly Leu
    290                 295                 300

Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Arg Pro
                325                 330                 335

Glu Asp Thr Ala Val Tyr Tyr Cys Ala Arg Ser Pro Ser Gly Phe Asn
            340                 345                 350

Arg Gly Gln Gly Thr Leu Val Thr Val Ser Ser Ala
        355                 360

<210> SEQ ID NO 8
<211> LENGTH: 364
<212> TYPE: PRT
<213> ORGANISM: Artificial Sequence
<220> FEATURE:
<223> OTHER INFORMATION: VHH2

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser Gly Gly Gly Gly Ser Gly Gly Gly Ser Glu Val Gln Leu
            115                 120                 125

Val Glu Ser Gly Gly Gly Leu Val Gln Pro Gly Asn Ser Leu Arg Leu
            130                 135                 140

Ser Cys Ala Ala Ser Gly Phe Thr Phe Ser Ser Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Ser Asp Thr Leu Tyr Ala Asp Ser Val Lys Gly Arg Phe
            180                 185                 190

Thr Ile Ser Arg Asp Asn Ala Lys Thr Thr Leu Tyr Leu Gln Met Asn
            195                 200                 205

Ser Leu Arg Pro Glu Asp Thr Ala Val Tyr Tyr Cys Thr Ile Gly Gly
            210                 215                 220

Ser Leu Ser Arg Ser Ser Gln Gly Thr Leu Val Thr Val Ser Ser Gly
225                 230                 235                 240

Gly Gly Gly Ser Gly Gly Gly Ser Glu Val Gln Leu Val Glu Ser Gly
                245                 250                 255

Gly Gly Leu Val Gln Pro Gly Gly Ser Leu Arg Leu Ser Cys Ala Ala
            260                 265                 270

Ser Gly Phe Thr Phe Ser Asp Tyr Trp Met Tyr Trp Val Arg Gln Ala
            275                 280                 285

Pro Gly Lys Gly Leu Glu Trp Val Ser Glu Ile Asn Thr Asn Gly Leu
            290                 295                 300

Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Arg Pro
                325                 330                 335

Glu Asp Thr Ala Val Tyr Tyr Cys Ala Arg Ser Pro Ser Gly Phe Asn
            340                 345                 350

Arg Gly Gln Gly Thr Leu Val Thr Val Ser Ser Ala
            355                 360

<210> SEQ ID NO 9
<211> LENGTH: 260
<212> TYPE: PRT
<213> ORGANISM: Artificial Sequence
<220> FEATURE:
<223> OTHER INFORMATION: VHH2

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Ala
        260

<210> SEQ ID NO 10
<211> LENGTH: 119
<212> TYPE: PRT
<213> ORGANISM: Artificial Sequence
<220> FEATURE:
<223> OTHER INFORMATION: Dom 1h-574-208

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 11
<211> LENGTH: 230
<212> TYPE: PRT
<213> ORGANISM: Artificial Sequence
<220> FEATURE:
<223> OTHER INFORMATION: Dom 1h-574-208-VL fusion

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

```
Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
                100                 105                 110

Thr Leu Val Thr Val Ser Ser Ala Ser Thr Asp Ile Gln Met Thr Gln
            115                 120                 125

Ser Pro Ser Ser Leu Ser Ala Ser Val Gly Asp Arg Val Thr Ile Thr
    130                 135                 140

Cys Arg Ala Ser Arg Pro Ile Gly Thr Thr Leu Ser Trp Tyr Gln Gln
145                 150                 155                 160

Lys Pro Gly Lys Ala Pro Lys Leu Leu Ile Leu Trp Asn Ser Arg Leu
                165                 170                 175

Gln Ser Gly Val Pro Ser Arg Phe Ser Gly Ser Gly Ser Gly Thr Asp
                180                 185                 190

Phe Thr Leu Thr Ile Ser Ser Leu Gln Pro Glu Asp Phe Ala Thr Tyr
            195                 200                 205

Tyr Cys Ala Gln Ala Gly Thr His Pro Thr Thr Phe Gly Gln Gly Thr
    210                 215                 220

Lys Val Glu Ile Lys Arg
225                 230

<210> SEQ ID NO 12
<211> LENGTH: 119
<212> TYPE: PRT
<213> ORGANISM: Artificial Sequence
<220> FEATURE:
<223> OTHER INFORMATION: DT04-H-033 (parental IL-13 dAb)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Gly Met Ala Trp Val Arg Gln Ala Pro Gly Lys Gly Leu Glu Trp Val
        35                  40                  45

Ser Thr Ile Ser Tyr Asn Gly Leu Tyr Thr Tyr Tyr Ala Asp Ser Val
    50                  55                  60

Lys Gly Arg Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Tyr Glu Tyr Ser Pro Glu Ser Asp Phe Asp Tyr Trp Gly Gln Gly
                100                 105                 110

Thr Leu Val Thr Val Ser Ser
            115

<210> SEQ ID NO 13
<211> LENGTH: 118
<212> TYPE: PRT
<213> ORGANISM: Artificial Sequence
```

```
<220> FEATURE:
<223> OTHER INFORMATION: Dom 10h-53-567

<400> SEQUENCE: 13

Gly Val Gln Leu Leu Glu Ser Gly Gly Gly Leu Val Gln Pro Gly Gly
1               5                   10                  15

Ser Leu Arg Leu Ser Cys Ala Ala Ser Gly Phe Val Phe Ala Trp Tyr
            20                  25                  30

Asp Met Gly Trp Val Arg Gln Ala Pro Gly Lys Gly Leu Glu Trp Val
        35                  40                  45

Ser Ser Ile Asp Trp His Gly Glu Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ala Glu Asp Glu Pro Gly Tyr Asp Tyr Trp Gly Gln Gly Thr
            100                 105                 110

Leu Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: anti-VH mAb M2.3G10.1G06

<400> SEQUENCE: 14

Asp Ile Val Met Thr Gln Ser Gln Lys Phe Met Ser Pro Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Gln Gln Tyr Gly Ser Tyr Pro Leu
                85                  90                  95

Thr Phe Gly Gly Gly Thr Lys Leu Glu Ile Lys
            100                 105

<210> SEQ ID NO 15
<211> LENGTH: 121
<212> TYPE: PRT
<213> ORGANISM: Artificial Sequence
<220> FEATURE:
<223> OTHER INFORMATION: anti-VH mAb M2.3G10.1G06

<400> SEQUENCE: 15

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Leu Thr Glu Ser
            20                  25                  30

Tyr Met His Trp Val Lys Gln Ser His Gly Lys Ser Leu Glu Trp Ile
        35                  40                  45
```

```
Gly Val Ile Ser Pro Tyr Asn Gly Gly Thr Ser Tyr Asn Gln Lys Phe
        50                  55                  60

Lys Asp Lys Ala Thr Leu Thr Val Asp Lys Ser Ser Thr Ala Tyr
 65                  70                  75                  80

Met Glu Leu Asn Ser Leu Thr Ser Glu Asp Ser Ala Val Tyr Tyr Cys
                 85                  90                  95

Thr Arg Arg Gly Ile Tyr Tyr Asp Pro Ser Trp Phe Ala Tyr Trp Gly
                100                 105                 110

Gln Gly Thr Leu Val Thr Val Ser Ala
            115                 120

<210> SEQ ID NO 16
<211> LENGTH: 120
<212> TYPE: PRT
<213> ORGANISM: Artificial Sequence
<220> FEATURE:
<223> OTHER INFORMATION: DOM1h-131-206 dAb

<400> SEQUENCE: 16

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
            35                  40                  45

Ser His Ile Pro Pro Asp Gly Gln Asp Pro Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Leu Leu Pro Lys Arg Gly Pro Trp Phe Asp Tyr Trp Gly Gln Gly
                100                 105                 110

Thr Leu Val Thr Val Ser Ser Ala
            115                 120

<210> SEQ ID NO 17
<211> LENGTH: 120
<212> TYPE: PRT
<213> ORGANISM: Artificial Sequence
<220> FEATURE:
<223> OTHER INFORMATION: DOM1h-131-206 dAb

<400> SEQUENCE: 17

Glu Val Gln Leu Leu Glu Ser Gly Gly Gly Leu Val Gln Ala Gly Gly
 1               5                  10                  15

Ser Leu Arg Leu Ser Cys Ala Ala Ser Gly Phe Thr Phe Ala His Glu
                20                  25                  30

Thr Met Val Trp Val Arg Gln Ala Pro Gly Lys Gly Leu Glu Trp Val
            35                  40                  45

Ser His Ile Pro Pro Asp Gly Gln Asp Pro Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Leu Leu Pro Lys Arg Gly Pro Trp Phe Asp Tyr Trp Gly Gln Gly
                100                 105                 110
```

```
Thr Leu Val Thr Val Ser Ser Ala
        115                 120

<210> SEQ ID NO 18
<211> LENGTH: 119
<212> TYPE: PRT
<213> ORGANISM: Artificial Sequence
<220> FEATURE:
<223> OTHER INFORMATION: DOM1h-131-206 dAb

<400> SEQUENCE: 18

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 19
<211> LENGTH: 124
<212> TYPE: PRT
<213> ORGANISM: Artificial Sequence
<220> FEATURE:
<223> OTHER INFORMATION: DOM1h-131-206 dAb

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser Ala Ser Thr Lys Gly
        115                 120

<210> SEQ ID NO 20
<211> LENGTH: 124
<212> TYPE: PRT
<213> ORGANISM: Artificial Sequence
<220> FEATURE:
<223> OTHER INFORMATION: DOM1h-131-206 dAb
```

```
<400> SEQUENCE: 20

Glu Val Gln Leu Leu Glu Ser Gly Gly Gly Leu Val Gln Ala Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser Ala Ser Thr Lys Gly
        115                 120

<210> SEQ ID NO 21
<211> LENGTH: 357
<212> TYPE: DNA
<213> ORGANISM: Artificial Sequence
<220> FEATURE:
<223> OTHER INFORMATION: DOM1h-131-206 dAb

<400> SEQUENCE: 21
gaagtacaac tgctggagag cggtggcggc ctggttcaac cgggtggttc cctgcgcctg      60
tcctgtgcgg catctggttt caccttcgca cacgaaacga tggtgtgggt tcgccaagct     120
ccgggcaaag gcctggaatg gtaagccac attcctccag atggccagga cccattctat     180
gcggattccg ttaagggtcg ctttaccatt tctcgtgata actccaaaaa caccctgtac     240
ctgcagatga actccctgcg cgccgaggat actgcggtgt accattgtgc gctgctgcct     300
aaacgtggcc gtggttcga ttactggggt cagggtactc tggtcaccgt aagcagc         357

<210> SEQ ID NO 22
<211> LENGTH: 360
<212> TYPE: DNA
<213> ORGANISM: Artificial Sequence
<220> FEATURE:
<223> OTHER INFORMATION: Dom1h-131-206

<400> SEQUENCE: 22
gaagtacaac tgctggagag cggtggcggc ctggttcaac cgggtggttc cctgcgcctg      60
tcctgtgcgg catctggttt caccttcgca cacgaaacga tggtgtgggt tcgccaagct     120
ccgggcaaag gcctggaatg gtaagccac attcctccag atggccagga cccattctat     180
gcggattccg ttaagggtcg ctttaccatt tctcgtgata actccaaaaa caccctgtac     240
ctgcagatga actccctgcg cgccgaggat actgcggtgt accattgtgc gctgctgcct     300
aaacgtggcc gtggttcga ttactggggt cagggtactc tggtcaccgt aagcagcgcg     360

<210> SEQ ID NO 23
<211> LENGTH: 372
<212> TYPE: DNA
<213> ORGANISM: Artificial Sequence
<220> FEATURE:
<223> OTHER INFORMATION: Dom1h-131-206
```

<400> SEQUENCE: 23

```
gaagtacaac tgctggagag cggtggcggc ctggttcaac cgggtggttc cctgcgcctg    60
tcctgtgcgg catctggttt caccttcgca cacgaaacga tggtgtgggt tcgccaagct   120
ccgggcaaag gcctggaatg gtaagccac attcctccag atggccagga cccattctat   180
gcggattccg ttaagggtcg ctttaccatt tctcgtgata actccaaaaa caccctgtac   240
ctgcagatga actccctgcg cgccgaggat actgcggtgt accattgtgc gctgctgcct   300
aaacgtggcc gtggttcga ttactggggt cagggtactc tggtcaccgt aagcagcgcg   360
tctaccaaag gt                                                      372
```

<210> SEQ ID NO 24
<211> LENGTH: 735
<212> TYPE: DNA
<213> ORGANISM: Artificial Sequence
<220> FEATURE:
<223> OTHER INFORMATION: anti-IL6 VHH

<400> SEQUENCE: 24

```
gaagtgcagc tggttgaatc tggcggtggt ctggttcagc cgggtggttc tctgcgtctg    60
tcttgcgcag cgtctggtag cgtttttcaaa atcaacgtga tggcgtggta tcgtcaggct   120
ccgggtaaag gtcgtgaact ggttgcgggt atcatttctg gcggtagcac ttcctacgcg   180
gactccgtta aggtcgtttt caccatcagc cgcgacaacg cgaaaaacac cctgtacctg   240
cagatgaact ctctgcgtcc ggaagatacc gcggtttact attgcgcgtt catcaccacc   300
gaatctgact acgacctggg tcgtcgttat tgggtcagg gtactctggt aaccgtatcc   360
tctggtggtg gtggttctgg tggtggttcc gaagtacagc tggtggaatc tggcggtggt   420
ctggtacagc cgggtaactc tctgcgtctg tcttgtgcgg cttctggttt caccttctcc   480
agcttcggta tgtcttgggt tcgtcaggca ccgggtaaag gtctggaatg ggtgtctagc   540
atctctggca gcggttctga taccctgtac gctgactccg tgaaaggtcg tttcactatc   600
tcccgcgaca acgcgaaaac caccctgtac ctgcagatga actctctgcg tccggaagac   660
accgctgttt actactgcac catcggtggt agcctgtccc gttcttctca gggtaccctg   720
gttactgtga gctct                                                  735
```

<210> SEQ ID NO 25
<211> LENGTH: 1089
<212> TYPE: DNA
<213> ORGANISM: Artificial Sequence
<220> FEATURE:
<223> OTHER INFORMATION: anti-TNF alpha VHH

<400> SEQUENCE: 25

```
gaagtgcagc tggtagaatc tggcggtggt ctggtacagc cgggtggttc tctgcgtctg    60
tcttgcgcag cttctggctt caccttctcc gactactgga tgtattgggt tcgtcaggcg   120
ccgggtaaag gtcgtgaatg ggtgtctgaa atcaaccacca acggcctgat caccaaatac   180
ccggactccg tgaaaggtcg tttcaccatc tcccgcgaca acgcgaaaaa caccctgtac   240
ctgcagatga actctctgcg tccggaagat accgcggttt actattgtgc gcgttctccg   300
tctggttttca accgtggtca gggtactctg gttaccgtaa gctctggtgg tggtggatcc   360
ggcggtggtt ctgaagttca gctggttgaa agcggtggtg gtctggtaca gccgggtaac   420
tctctgcgtc tgtcttgtgc ggcttctggc ttcaccttct cctctttcgg tatgtcttgg   480
gttcgtcagg caccgggtaa aggcctggaa tgggtttcct ctatctctgg tagcggttct   540
```

-continued

```
gacaccctgt acgctgactc tgttaaaggc cgcttcacca tctcccgtga caacgcgaaa      600
accaccctgt atctgcagat gaactccctg cgtccggaag ataccgctgt atactactgc      660
accatcggtg gctctctgtc tcgttcttct cagggtaccc tggttaccgt atctagcggt      720
ggtggtggat ccggtggcgg tagcgaagtt cagctggttg aatctggcgg tggtctggtt      780
cagccgggtg gttctctgcg tctgtcttgt gcagcgtctg gcttcacctt cagcgattac      840
tggatgtact gggttcgtca ggcaccgggt aaaggtctgg aatgggtgtc tgaaatcaac      900
accaacggtc tgatcaccaa ataccccggac agcgtgaaag tcgtttcac catcagccgt      960 gacaacgcga aaaacaccct gtacctgcag atgaactctc tgcgtccgga agacactgcg     1020
gtttattact gcgcacgttc tccgtctggt ttcaaccgtg gtcagggtac cctggttact     1080
gtatcctct                                                              1089
```

<210> SEQ ID NO 26
<211> LENGTH: 777
<212> TYPE: DNA
<213> ORGANISM: Artificial Sequence
<220> FEATURE:
<223> OTHER INFORMATION: anti-Von Willebrand VHH

<400> SEQUENCE: 26

```
gaggtacagc tggtggaaag cggtggtggt ctggttcagc cgggtggttc tctgcgtctg       60
tcttgcgcag cttctggccg taccttcagc tacaacccga tgggttggtt ccgtcaggct      120
ccgggtaaag gtcgtgaact ggttgcggcg atctctcgta ccggtggctc tacctactat      180
ccggactccg tggaaggtcg tttcaccatc tcccgcgaca cgcgaaacg tatggtatac      240 ctgcagatga acagcctgcg cgctgaagac accgcggttt actattgtgc tgcagcgggt      300
gttcgtgctg aagacggtcg tgttcgtacc ctgccgtccg aatacacctt ctggggtcag      360
ggtacccagg ttaccgtttc ttctgcagcg gcggaagtgc agctggttga atctggcggt      420
ggtctggtac agccgggtgg ttctctgcgt ctgtcttgtg ctgcgtctgg tcgcaccttc      480
tcctacaacc cgatgggttg gttccgtcag gcaccgggta aaggtcgtga actggtagcg      540
gcaatctctc gcactggtgg ctctacctac tacccggact ctgttgaagg ccgcttcacc      600
atctctcgtg acaacgcgaa acgtatggta tacctgcaga tgaactccct gcgtgcggaa      660
gacaccgcag tttattactg cgcggcagct ggtgttcgtg cagaagacgg tcgtgttcgt      720
accctgccga gcgaatacac cttctggggt cagggtaccc aggtaaccgt atcttct        777
```

<210> SEQ ID NO 27
<211> LENGTH: 738
<212> TYPE: DNA
<213> ORGANISM: Artificial Sequence
<220> FEATURE:
<223> OTHER INFORMATION: anti-IL6 VHH

<400> SEQUENCE: 27

```
gaagtgcagc tggttgaatc tggcggtggt ctggttcagc cgggtggttc tctgcgtctg       60
tcttgcgcag cgtctggtag cgttttcaaa atcaacgtga tggcgtggta tcgtcaggct      120
ccgggtaaag gtcgtgaact ggttgcgggt atcatttctg gcggtagcac ttcctacgcg      180
gactccgtta aggtcgtttt caccatcagc cgcgacaacg cgaaaaacac cctgtacctg      240
cagatgaact ctctgcgtcc ggaagatacc gcggtttact attgcgcgtt catcaccacc      300
gaatctgact acgacctggg tcgtcgttat tggggtcagg gtactctggt aaccgtatcc      360
```

| | |
|---|---|
| tctggtggtg gtggttctgg tggtggttcc gaagtacagc tggtggaatc tggcggtggt | 420 |
| ctggtacagc cgggtaactc tctgcgtctg tcttgtgcgg cttctggttt caccttctcc | 480 |
| agcttcggta tgtcttgggt tcgtcaggca ccgggtaaag gtctggaatg ggtgtctagc | 540 |
| atctctggca gcggttctga taccctgtac gctgactccg tgaaaggtcg tttcactatc | 600 |
| tcccgcgaca acgcgaaaac caccctgtac ctgcagatga actctctgcg tccggaagac | 660 |
| accgctgttt actactgcac catcggtggt agcctgtccc gttcttctca gggtaccctg | 720 |
| gttactgtga gctctgcg | 738 |

<210> SEQ ID NO 28
<211> LENGTH: 1092
<212> TYPE: DNA
<213> ORGANISM: Artificial Sequence
<220> FEATURE:
<223> OTHER INFORMATION: anti-TNF alpha VHH

<400> SEQUENCE: 28

| | |
|---|---|
| gaagtgcagc tggtagaatc tggcggtggt ctggtacagc cgggtggttc tctgcgtctg | 60 |
| tcttgcgcag cttctggctt caccttctcc gactactgga tgtattgggt tcgtcaggcg | 120 |
| ccgggtaaag gtctggaatg ggtgtctgaa atcaacacca acggcctgat caccaaatac | 180 |
| ccggactccg tgaaaggtcg tttcaccatc tcccgcgaca acgcgaaaaa caccctgtac | 240 |
| ctgcagatga actctctgcg tccggaagat accgcggttt actattgtgc gcgttctccg | 300 |
| tctggtttca accgtggtca gggtactctg gttaccgtaa gctctggtgg tggtggatcc | 360 |
| ggcggtggtt ctgaagttca gctggttgaa agcggtggtg gtctggtaca gccgggtaac | 420 |
| tctctgcgtc tgtcttgtgc ggcttctggc ttcaccttct cctctttcgg tatgtcttgg | 480 |
| gttcgtcagg caccgggtaa aggcctgaa tgggtttcct ctatctctgg tagcggttct | 540 |
| gacaccctgt acgctgactc tgttaaaggc cgcttcacca tctcccgtga caacgcgaaa | 600 |
| accaccctgt atctgcagat gaactccctg cgtccggaag ataccgctgt atactactgc | 660 |
| accatcggtg gctctctgtc tcgttcttct cagggtaccc tggttaccgt atctagcggt | 720 |
| ggtggtggat ccggtggcgg tagcgaagtt cagctggttg aatctggcgg tggtctggtt | 780 |
| cagccgggtg gttctctgcg tctgtcttgt gcagcgtctg gcttcacctt cagcgattac | 840 |
| tggatgtact gggttcgtca ggcaccgggt aaaggtctgg aatgggtgtc tgaaatcaac | 900 |
| accaacggtc tgatcaccaa ataccctggac agcgtgaaag gtcgtttcac catcagccgt | 960 |
| gacaacgcga aaacacccct gtacctgcag atgaactctc tgcgtccgga agacactgcg | 1020 |
| gtttattact gcgcacgttc tccgtctggt ttcaaccgtg gtcagggtac cctggttact | 1080 |
| gtatcctctg cg | 1092 |

<210> SEQ ID NO 29
<211> LENGTH: 780
<212> TYPE: DNA
<213> ORGANISM: Artificial Sequence
<220> FEATURE:
<223> OTHER INFORMATION: anti-Von Willebrand VHH

<400> SEQUENCE: 29

| | |
|---|---|
| gaggtacagc tggtggaaag cggtggtggt ctggttcagc cgggtggttc tctgcgtctg | 60 |
| tcttgcgcag cttctggccg taccttcagc tacaacccga tgggttggtt ccgtcaggct | 120 |
| ccgggtaaag gtcgtgaact ggttgcggcg atctctcgta ccggtggctc tacctactat | 180 |
| ccggactccg tggaaggtcg tttcaccatc tcccgcgaca acgcgaaacg tatggtatac | 240 |

```
ctgcagatga acagcctgcg cgctgaagac accgcggttt actattgtgc tgcagcgggt    300
gttcgtgctg aagacggtcg tgttcgtacc ctgccgtccg aatacacctt ctggggtcag    360
ggtacccagg ttaccgtttc ttctgcagcg gcggaagtgc agctggttga atctggcggt    420
ggtctggtac agccgggtgg ttctctgcgt ctgtcttgtg ctgcgtctgg tcgcaccttc    480
tcctacaacc cgatgggttg gttccgtcag gcaccgggta aggtcgtga actggtagcg    540 gcaatctctc gcactggtgg ctctacctac tacccggact ctgttgaagg ccgcttcacc    600
atctctcgtg acaacgcgaa acgtatggtg tacctgcaga tgaactccct gcgtgcggaa    660
gacaccgcag tttattactg cgcggcagct ggtgttcgtg cagaagacgg tcgtgttcgt    720
accctgccga gcgaatacac cttctggggt cagggtaccc aggtaaccgt atcttctgcg    780
```

<210> SEQ ID NO 30
<211> LENGTH: 581
<212> TYPE: PRT
<213> ORGANISM: Artificial Sequence
<220> FEATURE:
<223> OTHER INFORMATION: mAb-VL '735 molecule (IL-13mAb: IL-4Vkappa dAb)
      '735 molecule

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
```

Asp Val Ser His Glu Asp Pro Glu Val Lys Phe Asn Trp Tyr Val Asp
260                 265                 270

Gly Val Glu Val His Asn Ala Lys Thr Lys Pro Arg Glu Glu Gln Tyr
    275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
            325                 330                 335

Glu Pro Gln Val Tyr Thr Leu Pro Pro Ser Arg Asp Glu Leu Thr Lys
340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Met His Glu Ala Leu His Asn His Tyr Thr Gln Lys Ser
420                 425                 430

Leu Ser Leu Ser Pro Gly Lys Gly Ser Thr Val Ala Ala Pro Ser Gly
    435                 440                 445

Ser Thr Val Ala Ala Pro Ser Gly Ser Asp Ile Gln Met Thr Gln Ser
450                 455                 460

Pro Ser Ser Leu Ser Ala Ser Val Gly Asp Arg Val Thr Ile Thr Cys
465                 470                 475                 480

Arg Ala Ser Arg Pro Ile Ser Asp Trp Leu His Trp Tyr Gln Gln Lys
            485                 490                 495

Pro Gly Lys Ala Pro Lys Leu Leu Ile Ala Trp Ala Ser Ser Leu Gln
500                 505                 510

Gly Gly Val Pro Ser Arg Phe Ser Gly Ser Gly Ser Gly Thr Asp Phe
    515                 520                 525

Thr Leu Thr Ile Ser Ser Leu Gln Pro Glu Asp Phe Ala Thr Tyr Tyr
530                 535                 540

Cys Gln Gln Glu Gly Trp Gly Pro Pro Thr Phe Gly Gln Gly Thr Lys
545                 550                 555                 560

Val Glu Ile Lys Arg
            565                 570                 575

<210> SEQ ID NO 31
<211> LENGTH: 219
<212> TYPE: PRT
<213> ORGANISM: Artificial Sequence
<220> FEATURE:
<223> OTHER INFORMATION: 735 molecule

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ile
            20                  25                  30

Asn Gly Asn Thr Tyr Leu Glu Trp Tyr Leu Gln Lys Pro Gly Gln Ser

```
            35                  40                  45
Pro Arg Leu Ile Tyr Lys Ile Ser Asp Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Ile Tyr Tyr Cys Phe Gln Gly
                 85                  90                  95

Ser His Val Pro Trp Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 32
<211> LENGTH: 571
<212> TYPE: PRT
<213> ORGANISM: Artificial Sequence
<220> FEATURE:
<223> OTHER INFORMATION: 15014

<400> SEQUENCE: 32

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Gly Val Ser Trp Ile Arg Gln Pro Pro Gly Lys Gly Leu Glu
             35                  40                  45

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

-continued

```
                180             185             190
        Pro Ser Ser Ser Leu Gly Thr Gln Thr Tyr Ile Cys Asn Val Asn His
            195                 200                 205
        Lys Pro Ser Asn Thr Lys Val Asp Lys Lys Val Glu Pro Lys Ser Cys
            210                 215                 220
        Asp Lys Thr His Thr Cys Pro Pro Cys Pro Ala Pro Glu Leu Leu Gly
        225                 230                 235                 240
        Gly Pro Ser Val Phe Leu Phe Pro Pro Lys Pro Lys Asp Thr Leu Met
                        245                 250                 255
        Ile Ser Arg Thr Pro Glu Val Thr Cys Val Val Val Asp Val Ser His
                    260                 265                 270
        Glu Asp Pro Glu Val Lys Phe Asn Trp Tyr Val Asp Gly Val Glu Val
                275                 280                 285
        His Asn Ala Lys Thr Lys Pro Arg Glu Glu Gln Tyr Asn Ser Thr Tyr
            290                 295                 300
        Arg Val Val Ser Val Leu Thr Val Leu His Gln Asp Trp Leu Asn Gly
        305                 310                 315                 320
        Lys Glu Tyr Lys Cys Lys Val Ser Asn Lys Ala Leu Pro Ala Pro Ile
                        325                 330                 335
        Glu Lys Thr Ile Ser Lys Ala Lys Gly Gln Pro Arg Glu Pro Gln Val
                    340                 345                 350
        Tyr Thr Leu Pro Pro Ser Arg Asp Glu Leu Thr Lys Asn Gln Val Ser
                355                 360                 365
        Leu Thr Cys Leu Val Lys Gly Phe Tyr Pro Ser Asp Ile Ala Val Glu
            370                 375                 380
        Trp Glu Ser Asn Gly Gln Pro Glu Asn Asn Tyr Lys Thr Thr Pro Pro
        385                 390                 395                 400
        Val Leu Asp Ser Asp Gly Ser Phe Phe Leu Tyr Ser Lys Leu Thr Val
                        405                 410                 415
        Asp Lys Ser Arg Trp Gln Gln Gly Asn Val Phe Ser Cys Ser Val Met
                    420                 425                 430
        His Glu Ala Leu His Asn His Tyr Thr Gln Lys Ser Leu Ser Leu Ser
                435                 440                 445
        Pro Gly Lys Gly Ser Thr Val Ala Ala Pro Ser Thr Asp Ile Gln Met
            450                 455                 460
        Thr Gln Ser Pro Ser Ser Leu Ser Ala Ser Val Gly Asp Arg Val Thr
        465                 470                 475                 480
        Ile Thr Cys Arg Ala Ser Arg Pro Ile Ser Asp Trp Leu His Trp Tyr
                        485                 490                 495
        Gln Gln Lys Pro Gly Lys Ala Pro Lys Leu Leu Ile Ala Trp Ala Ser
                    500                 505                 510
        Ser Leu Gln Gly Gly Val Pro Ser Arg Phe Ser Gly Ser Gly Ser Gly
                515                 520                 525
        Thr Asp Phe Thr Leu Thr Ile Ser Ser Leu Gln Pro Glu Asp Phe Ala
            530                 535                 540
        Thr Tyr Tyr Cys Gln Gln Gly Trp Gly Pro Pro Thr Phe Gly Gln
        545                 550                 555                 560
        Gly Thr Lys Val Glu Ile Lys Arg Ala Ala Ala
                        565                 570

<210> SEQ ID NO 33
<211> LENGTH: 218
<212> TYPE: PRT
<213> ORGANISM: Artificial Sequence
```

<220> FEATURE:
<223> OTHER INFORMATION: 15014

<400> SEQUENCE: 33

Asp Ile Val Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Pro Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 34
<211> LENGTH: 569
<212> TYPE: PRT
<213> ORGANISM: Artificial Sequence
<220> FEATURE:
<223> OTHER INFORMATION: mAb-VL 15019

<400> SEQUENCE: 34

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser

```
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys Gly Ser Thr Val Ala Ala Pro Ser Thr Asp Ile Gln Met
                450                 455                 460
Thr Gln Ser Pro Ser Ser Leu Ser Ala Ser Val Gly Asp Arg Val Thr
465                 470                 475                 480
Ile Thr Cys Arg Ala Ser Arg Pro Ile Ser Asp Trp Leu His Trp Tyr
                485                 490                 495
Gln Gln Lys Pro Gly Lys Ala Pro Lys Leu Leu Ile Ala Trp Ala Ser
                500                 505                 510
Ser Leu Gln Gly Gly Val Pro Ser Arg Phe Ser Gly Ser Gly Ser Gly
                515                 520                 525
Thr Asp Phe Thr Leu Thr Ile Ser Ser Leu Gln Pro Glu Asp Phe Ala
530                 535                 540
```

```
Thr Tyr Tyr Cys Gln Gln Glu Gly Trp Gly Pro Pro Thr Phe Gly Gln
545                 550                 555                 560

Gly Thr Lys Val Glu Ile Lys Arg Thr
                565

<210> SEQ ID NO 35
<211> LENGTH: 218
<212> TYPE: PRT
<213> ORGANISM: Artificial Sequence
<220> FEATURE:
<223> OTHER INFORMATION: mAb-VL 15019

<400> SEQUENCE: 35

Asp Ile Val Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Pro Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 36
<211> LENGTH: 570
<212> TYPE: PRT
<213> ORGANISM: Artificial Sequence
<220> FEATURE:
<223> OTHER INFORMATION: mAb-VL 15020

<400> SEQUENCE: 36

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
```

```
            50                  55                  60
Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys Gly Ser Thr Val Ala Ala Pro Ser Thr Asp Ile Gln Met
                450                 455                 460

Thr Gln Ser Pro Ser Ser Leu Ser Ala Ser Val Gly Asp Arg Val Thr
465                 470                 475                 480
```

```
Ile Thr Cys Arg Ala Ser Arg Pro Ile Ser Asp Trp Leu His Trp Tyr
            485                 490                 495

Gln Gln Lys Pro Gly Lys Ala Pro Lys Leu Leu Ile Ala Trp Ala Ser
        500                 505                 510

Ser Leu Gln Gly Gly Val Pro Ser Arg Phe Ser Gly Ser Gly Ser Gly
        515                 520                 525

Thr Asp Phe Thr Leu Thr Ile Ser Ser Leu Gln Pro Glu Asp Phe Ala
        530                 535                 540

Thr Tyr Tyr Cys Gln Gln Glu Gly Trp Gly Pro Pro Thr Phe Gly Gln
545                 550                 555                 560

Gly Thr Lys Val Glu Ile Lys Arg Thr Val
                565                 570

<210> SEQ ID NO 37
<211> LENGTH: 218
<212> TYPE: PRT
<213> ORGANISM: Artificial Sequence
<220> FEATURE:
<223> OTHER INFORMATION: mAb-VL 15020

<400> SEQUENCE: 37

Asp Ile Val Leu Thr Gln Ser Pro Ser Ser Leu Ser Ala Ser Val Gly
1               5                  10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Pro Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 38
<211> LENGTH: 530
<212> TYPE: PRT
<213> ORGANISM: Artificial Sequence
<220> FEATURE:
<223> OTHER INFORMATION: mAb-VL 15021
```

```
<400> SEQUENCE: 38

Trp Ile Arg Gln Pro Gly Lys Gly Leu Glu Trp Leu Ala His Ile
1               5                   10                  15

Tyr Trp Asp Asp Asp Lys Arg Tyr Asn Pro Ser Leu Lys Ser Arg Leu
                20                  25                  30

Thr Ile Ser Lys Asp Thr Ser Arg Asn Gln Val Val Leu Thr Met Thr
                35                  40                  45

Asn Met Asp Pro Val Asp Thr Ala Thr Tyr Tyr Cys Ala Arg Arg Glu
            50                  55                  60

Thr Val Phe Tyr Trp Tyr Phe Asp Val Trp Gly Arg Gly Thr Leu Val
65              70                  75                  80

Thr Val Ser Ser Ala Ser Thr Lys Gly Pro Ser Val Phe Pro Leu Ala
                85                  90                  95

Pro Ser Ser Lys Ser Thr Ser Gly Gly Thr Ala Ala Leu Gly Cys Leu
            100                 105                 110

Val Lys Asp Tyr Phe Pro Glu Pro Val Thr Val Ser Trp Asn Ser Gly
            115                 120                 125

Ala Leu Thr Ser Gly Val His Thr Phe Pro Ala Val Leu Gln Ser Ser
        130                 135                 140

Gly Leu Tyr Ser Leu Ser Ser Val Val Thr Val Pro Ser Ser Ser Leu
145                 150                 155                 160

Gly Thr Gln Thr Tyr Ile Cys Asn Val Asn His Lys Pro Ser Asn Thr
                165                 170                 175

Lys Val Asp Lys Lys Val Glu Pro Lys Ser Cys Asp Lys Thr His Thr
            180                 185                 190

Cys Pro Pro Cys Pro Ala Pro Glu Leu Leu Gly Gly Pro Ser Val Phe
        195                 200                 205

Leu Phe Pro Pro Lys Pro Lys Asp Thr Leu Met Ile Ser Arg Thr Pro
210                 215                 220

Glu Val Thr Cys Val Val Val Asp Val Ser His Glu Asp Pro Glu Val
225                 230                 235                 240

Lys Phe Asn Trp Tyr Val Asp Gly Val Glu Val His Asn Ala Lys Thr
                245                 250                 255

Lys Pro Arg Glu Glu Gln Tyr Asn Ser Thr Tyr Arg Val Val Ser Val
            260                 265                 270

Leu Thr Val Leu His Gln Asp Trp Leu Asn Gly Lys Glu Tyr Lys Cys
        275                 280                 285

Lys Val Ser Asn Lys Ala Leu Pro Ala Pro Ile Glu Lys Thr Ile Ser
290                 295                 300

Lys Ala Lys Gly Gln Pro Arg Glu Pro Gln Val Tyr Thr Leu Pro Pro
305                 310                 315                 320

Ser Arg Asp Glu Leu Thr Lys Asn Gln Val Ser Leu Thr Cys Leu Val
                325                 330                 335

Lys Gly Phe Tyr Pro Ser Asp Ile Ala Val Glu Trp Glu Ser Asn Gly
            340                 345                 350

Gln Pro Glu Asn Asn Tyr Lys Thr Thr Pro Pro Val Leu Asp Ser Asp
        355                 360                 365

Gly Ser Phe Phe Leu Tyr Ser Lys Leu Thr Val Asp Lys Ser Arg Trp
370                 375                 380

Gln Gln Gly Asn Val Phe Ser Cys Ser Val Met His Glu Ala Leu His
385                 390                 395                 400

Asn His Tyr Thr Gln Lys Ser Leu Ser Leu Ser Pro Gly Lys Gly Ser
                405                 410                 415
```

```
Thr Val Ala Ala Pro Ser Thr Asp Ile Gln Met Thr Gln Ser Pro Ser
            420                 425                 430

Ser Leu Ser Ala Ser Val Gly Asp Arg Val Thr Ile Thr Cys Arg Ala
            435                 440                 445

Ser Arg Pro Ile Ser Asp Trp Leu His Trp Tyr Gln Gln Lys Pro Gly
            450                 455                 460

Lys Ala Pro Lys Leu Leu Ile Ala Trp Ala Ser Ser Leu Gln Gly Gly
465                 470                 475                 480

Val Pro Ser Arg Phe Ser Gly Ser Gly Ser Gly Thr Asp Phe Thr Leu
            485                 490                 495

Thr Ile Ser Ser Leu Gln Pro Glu Asp Phe Ala Thr Tyr Tyr Cys Gln
            500                 505                 510

Gln Glu Gly Trp Gly Pro Pro Thr Phe Gly Gln Gly Thr Lys Val Glu
            515                 520                 525

Ile Lys
    530

<210> SEQ ID NO 39
<211> LENGTH: 218
<212> TYPE: PRT
<213> ORGANISM: Artificial Sequence
<220> FEATURE:
<223> OTHER INFORMATION: mAb-VL 15021

<400> SEQUENCE: 39

Asp Ile Val Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Pro Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 40
```

<211> LENGTH: 481
<212> TYPE: PRT
<213> ORGANISM: Artificial Sequence
<220> FEATURE:
<223> OTHER INFORMATION: DMS30045: DOM15-26-597 dAb N-(VEPKSSDK linker) & C-terminal K-044-085 dAb ((TGLDSP)x4)

<400> SEQUENCE: 40

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125

Pro Pro Cys Pro Ala Pro Glu Leu Leu Gly Gly Pro Ser Val Phe Leu
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
            340                 345                 350

Asp Ser Pro Thr Gly Leu Asp Ser Pro Thr Gly Leu Asp Ser Pro Thr
        355                 360                 365

Gly Leu Asp Ser Pro Asp Ile Gln Met Thr Gln Ser Pro Ser Ser Leu
```

```
                370                 375                 380
Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
                420                 425                 430

Ser Arg Phe Ser Gly Ser Gly Ser Gly Thr Asp Phe Thr Leu Thr Ile
                435                 440                 445

Ser Ser Leu Gln Pro Glu Asp Phe Ala Thr Tyr Tyr Cys Gln Gln Tyr
450                 455                 460

Met Tyr Tyr Pro His Thr Phe Gly Gln Gly Thr Lys Val Glu Ile Lys
465                 470                 475                 480

Arg

<210> SEQ ID NO 41
<211> LENGTH: 475
<212> TYPE: PRT
<213> ORGANISM: Artificial Sequence
<220> FEATURE:
<223> OTHER INFORMATION: DMS30046: DMS1576 with C-terminal K-044-085 dAb
      ((TGLDSP)x4)

<400> SEQUENCE: 41

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
                20                  25                  30

Pro Met Met Trp Val Arg Gln Ala Pro Gly Lys Gly Leu Glu Trp Val
                35                  40                  45

Ser Glu Ile Ser Pro Ser Gly Ser Asn Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
                100                 105                 110

Thr Val Ser Ser Ala Ser Thr His Thr Cys Pro Pro Cys Pro Ala Pro
                115                 120                 125

Glu Leu Leu Gly Gly Pro Ser Val Phe Leu Phe Pro Pro Lys Pro Lys
                130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
                195                 200                 205

Trp Leu Asn Gly Lys Glu Tyr Lys Cys Lys Val Ser Asn Lys Ala Leu
                210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
```

```
                    245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
                275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
                340                 345                 350

Asp Ser Pro Thr Gly Leu Asp Ser Pro Thr Gly Leu Asp Ser Pro Asp
                355                 360                 365

Ile Gln Met Thr Gln Ser Pro Ser Ser Leu Ser Ala Ser Val Gly Asp
                370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
                420                 425                 430

Gly Ser Gly Thr Asp Phe Thr Leu Thr Ile Ser Ser Leu Gln Pro Glu
                435                 440                 445

Asp Phe Ala Thr Tyr Tyr Cys Gln Gln Tyr Met Tyr Tyr Pro His Thr
                450                 455                 460

Phe Gly Gln Gly Thr Lys Val Glu Ile Lys Arg
465                 470                 475

<210> SEQ ID NO 42
<211> LENGTH: 480
<212> TYPE: PRT
<213> ORGANISM: Artificial Sequence
<220> FEATURE:
<223> OTHER INFORMATION: DMS30047 (contains modified C terminus) :
      DOM15-26-597 dAb N-(VEPKSSDK linker) & C-terminal
      K-044-085 dAb minus C-term R ((TGLDSP)x4)

<400> SEQUENCE: 42

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
                20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125
```

```
Pro Pro Cys Pro Ala Pro Glu Leu Leu Gly Gly Pro Ser Val Phe Leu
        130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
            165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
        210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
            340                 345                 350

Asp Ser Pro Thr Gly Leu Asp Ser Pro Thr Gly Leu Asp Ser Pro Thr
        355                 360                 365

Gly Leu Asp Ser Pro Asp Ile Gln Met Thr Gln Ser Pro Ser Ser Leu
        370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
            420                 425                 430

Ser Arg Phe Ser Gly Ser Gly Ser Gly Thr Asp Phe Thr Leu Thr Ile
        435                 440                 445

Ser Ser Leu Gln Pro Glu Asp Phe Ala Thr Tyr Tyr Cys Gln Gln Tyr
450                 455                 460

Met Tyr Tyr Pro His Thr Phe Gly Gln Gly Thr Lys Val Glu Ile Lys
465                 470                 475                 480
```

<210> SEQ ID NO 43
<211> LENGTH: 482
<212> TYPE: PRT
<213> ORGANISM: Artificial Sequence
<220> FEATURE:
<223> OTHER INFORMATION: DMS30048 (contains modified C terminus):
    DOM15-26-597 dAb N-(VEPKSSDK linker) & C-terminal
    K-044-085 dAb + A ((TGLDSP)x4

<400> SEQUENCE: 43

```
Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
                115                 120                 125

Pro Pro Cys Pro Ala Pro Glu Leu Leu Gly Gly Pro Ser Val Phe Leu
            130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
                180                 185                 190

Pro Arg Glu Glu Gln Tyr Asn Ser Thr Tyr Arg Val Val Ser Val Leu
            195                 200                 205

Thr Val Leu His Gln Asp Trp Leu Asn Gly Lys Glu Tyr Lys Cys Lys
            210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
            275                 280                 285

Pro Glu Asn Asn Tyr Lys Thr Thr Pro Pro Val Leu Asp Ser Asp Gly
            290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
            340                 345                 350

Asp Ser Pro Thr Gly Leu Asp Ser Pro Thr Gly Leu Asp Ser Pro Thr
            355                 360                 365

Gly Leu Asp Ser Pro Asp Ile Gln Met Thr Gln Ser Pro Ser Ser Leu
            370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
```

```
                420           425           430
Ser Arg Phe Ser Gly Ser Gly Ser Gly Thr Asp Phe Thr Leu Thr Ile
            435               440           445

Ser Ser Leu Gln Pro Glu Asp Phe Ala Thr Tyr Tyr Cys Gln Gln Tyr
450                 455               460

Met Tyr Tyr Pro His Thr Phe Gly Gln Gly Thr Lys Val Glu Ile Lys
465                 470               475               480

Arg Ala

<210> SEQ ID NO 44
<211> LENGTH: 484
<212> TYPE: PRT
<213> ORGANISM: Artificial Sequence
<220> FEATURE:
<223> OTHER INFORMATION: DMS30049 (contains modified C terminus):
      DOM15-26-597 dAb N-(VEPKSSDK linker) & C-terminal
      K-044-085 dAb +AAA ((TGLDSP)x4)

<400> SEQUENCE: 44

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285
```

-continued

```
Pro Glu Asn Asn Tyr Lys Thr Thr Pro Val Leu Asp Ser Asp Gly
    290                 295                 300

Ser Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
                340                 345                 350

Asp Ser Pro Thr Gly Leu Asp Ser Pro Thr Gly Leu Asp Ser Pro Thr
            355                 360                 365

Gly Leu Asp Ser Pro Asp Ile Gln Met Thr Gln Ser Pro Ser Ser Leu
        370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
                420                 425                 430

Ser Arg Phe Ser Gly Ser Gly Ser Gly Thr Asp Phe Thr Leu Thr Ile
            435                 440                 445

Ser Ser Leu Gln Pro Glu Asp Phe Ala Thr Tyr Tyr Cys Gln Gln Tyr
450                 455                 460

Met Tyr Tyr Pro His Thr Phe Gly Gln Gly Thr Lys Val Glu Ile Lys
465                 470                 475                 480

Arg Ala Ala Ala
```

<210> SEQ ID NO 45
<211> LENGTH: 482
<212> TYPE: PRT
<213> ORGANISM: Artificial Sequence
<220> FEATURE:
<223> OTHER INFORMATION: DMS30050 (contains modified C terminus):
    DOM15-26-597 dAb N-(VEPKSSDK linker) & C-terminal
    K-044-085 dAb +T ((TGLDSP)x4)

<400> SEQUENCE: 45

```
Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160
```

Val Thr Cys Val Val Val Asp Val Ser His Glu Asp Pro Glu Val Lys
            165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
            195                 200                 205

Thr Val Leu His Gln Asp Trp Leu Asn Gly Lys Glu Tyr Lys Cys Lys
            210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
            245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
            275                 280                 285

Pro Glu Asn Asn Tyr Lys Thr Thr Pro Pro Val Leu Asp Ser Asp Gly
            290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
            325                 330                 335

His Tyr Thr Gln Lys Ser Leu Ser Leu Ser Pro Gly Lys Thr Gly Leu
            340                 345                 350

Asp Ser Pro Thr Gly Leu Asp Ser Pro Thr Gly Leu Asp Ser Pro Thr
            355                 360                 365

Gly Leu Asp Ser Pro Asp Ile Gln Met Thr Gln Ser Pro Ser Ser Leu
            370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
            405                 410                 415

Pro Lys Leu Leu Ile Tyr His Gly Ser Ile Leu Gln Ser Gly Val Pro
            420                 425                 430

Ser Arg Phe Ser Gly Ser Gly Ser Gly Thr Asp Phe Thr Leu Thr Ile
            435                 440                 445

Ser Ser Leu Gln Pro Glu Asp Phe Ala Thr Tyr Tyr Cys Gln Gln Tyr
450                 455                 460

Met Tyr Tyr Pro His Thr Phe Gly Gln Gly Thr Lys Val Glu Ile Lys
465                 470                 475                 480

Arg Thr

<210> SEQ ID NO 46
<211> LENGTH: 474
<212> TYPE: PRT
<213> ORGANISM: Artificial Sequence
<220> FEATURE:
<223> OTHER INFORMATION: DMS30051 (contains modified C terminus):
      DMS1576 with C-terminal K-044-085 dAb minus C-term R
      ((TGLDSP)x4)

<400> SEQUENCE: 46

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr

```
                20                  25                  30
Pro Met Met Trp Val Arg Gln Ala Pro Gly Lys Gly Leu Glu Trp Val
            35                  40                  45
Ser Glu Ile Ser Pro Ser Gly Ser Asn Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Pro Arg Lys Leu Asp Tyr Trp Gly Gln Gly Thr Leu Val
            100                 105                 110
Thr Val Ser Ser Ala Ser Thr His Thr Cys Pro Pro Cys Pro Ala Pro
        115                 120                 125
Glu Leu Leu Gly Gly Pro Ser Val Phe Leu Phe Pro Pro Lys Pro Lys
    130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
            180                 185                 190
Asn Ser Thr Tyr Arg Val Val Ser Val Leu Thr Val Leu His Gln Asp
        195                 200                 205
Trp Leu Asn Gly Lys Glu Tyr Lys Cys Lys Val Ser Asn Lys Ala Leu
    210                 215                 220
Pro Ala Pro Ile Glu Lys Thr Ile Ser Lys Ala Lys Gly Gln Pro Arg
225                 230                 235                 240
Glu Pro Gln Val Tyr Thr Leu Pro Pro Ser Arg Asp Glu Leu Thr Lys
                245                 250                 255
Asn Gln Val Ser Leu Thr Cys Leu Val Lys Gly Phe Tyr Pro Ser Asp
            260                 265                 270
Ile Ala Val Glu Trp Glu Ser Asn Gly Gln Pro Glu Asn Asn Tyr Lys
        275                 280                 285
Thr Thr Pro Pro Val Leu Asp Ser Asp Gly Ser Phe Phe Leu Tyr Ser
    290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys Thr Gly Leu Asp Ser Pro Thr Gly Leu
            340                 345                 350
Asp Ser Pro Thr Gly Leu Asp Ser Pro Thr Gly Leu Asp Ser Pro Asp
        355                 360                 365
Ile Gln Met Thr Gln Ser Pro Ser Ser Leu Ser Ala Ser Val Gly Asp
    370                 375                 380
Arg Val Thr Ile Thr Cys Arg Ala Ser Gln Trp Ile Gly Pro Glu Leu
385                 390                 395                 400
Lys Trp Tyr Gln Gln Lys Pro Gly Lys Ala Pro Lys Leu Leu Ile Tyr
                405                 410                 415
His Gly Ser Ile Leu Gln Ser Gly Val Pro Ser Arg Phe Ser Gly Ser
            420                 425                 430
Gly Ser Gly Thr Asp Phe Thr Leu Thr Ile Ser Ser Leu Gln Pro Glu
        435                 440                 445
```

```
Asp Phe Ala Thr Tyr Tyr Cys Gln Gln Tyr Met Tyr Tyr Pro His Thr
            450                 455                 460

Phe Gly Gln Gly Thr Lys Val Glu Ile Lys
465                 470

<210> SEQ ID NO 47
<211> LENGTH: 476
<212> TYPE: PRT
<213> ORGANISM: Artificial Sequence
<220> FEATURE:
<223> OTHER INFORMATION: DMS30052 (contains modified C terminus):
      DMS1576 with C-terminal K-044-085 dAb +A ((TGLDSP)x4)

<400> SEQUENCE: 47

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
```

```
                      325                 330                 335
Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
            355                 360                 365

Ile Gln Met Thr Gln Ser Pro Ser Ser Leu Ser Ala Ser Val Gly Asp
            370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
            435                 440                 445

Asp Phe Ala Thr Tyr Tyr Cys Gln Gln Tyr Met Tyr Tyr Pro His Thr
            450                 455                 460

Phe Gly Gln Gly Thr Lys Val Glu Ile Lys Arg Ala
465                 470                 475

<210> SEQ ID NO 48
<211> LENGTH: 478
<212> TYPE: PRT
<213> ORGANISM: Artificial Sequence
<220> FEATURE:
<223> OTHER INFORMATION: DMS30053 (contains modified C terminus):
      DMS1576 with C-terminal K-044-085 dAb +AAA ((TGLDSP)x4)

<400> SEQUENCE: 48

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205
```

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
        355                 360                 365

Ile Gln Met Thr Gln Ser Pro Ser Ser Leu Ser Ala Ser Val Gly Asp
    370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gln Gln Tyr Met Tyr Tyr Pro His Thr
    450                 455                 460

Phe Gly Gln Gly Thr Lys Val Glu Ile Lys Arg Ala Ala Ala
465                 470                 475

<210> SEQ ID NO 49
<211> LENGTH: 476
<212> TYPE: PRT
<213> ORGANISM: Artificial Sequence
<220> FEATURE:
<223> OTHER INFORMATION: DMS30054 (contains modified C terminus):
      DMS1576 with C-terminal K-044-085 dAb +T ((TGLDSP)x4)

<400> SEQUENCE: 49

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
                195                 200                 205

Trp Leu Asn Gly Lys Glu Tyr Lys Cys Lys Val Ser Asn Lys Ala Leu
            210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
            355                 360                 365

Ile Gln Met Thr Gln Ser Pro Ser Ser Leu Ser Ala Ser Val Gly Asp
            370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
            435                 440                 445

Asp Phe Ala Thr Tyr Tyr Cys Gln Gln Tyr Met Tyr Tyr Pro His Thr
            450                 455                 460

Phe Gly Gln Gly Thr Lys Val Glu Ile Lys Arg Thr
465                 470                 475

<210> SEQ ID NO 50
<211> LENGTH: 6
<212> TYPE: PRT
<213> ORGANISM: artificial sequence
<220> FEATURE:
```

```
-continued

<223> OTHER INFORMATION: C terminal sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 50

Val Thr Val Ser Ser Xaa
1               5

<210> SEQ ID NO 51
<211> LENGTH: 5
<212> TYPE: PRT
<213> ORGANISM: artificial sequence
<220> FEATURE:
<223> OTHER INFORMATION: C terminal sequence

<400> SEQUENCE: 51

Val Thr Val Ser Ser
1               5

<210> SEQ ID NO 52
<211> LENGTH: 4
<212> TYPE: PRT
<213> ORGANISM: artificial sequence
<220> FEATURE:
<223> OTHER INFORMATION: C terminal extension

<400> SEQUENCE: 52

Ala Ser Thr Lys
1

<210> SEQ ID NO 53
<211> LENGTH: 5
<212> TYPE: PRT
<213> ORGANISM: artificial sequence
<220> FEATURE:
<223> OTHER INFORMATION: C terminal extension

<400> SEQUENCE: 53

Ala Ser Thr Lys Gly
1               5
```

UNITED STATES PATENT AND TRADEMARK OFFICE
CERTIFICATE OF CORRECTION

PATENT NO. : 10,808,040 B2
APPLICATION NO. : 14/239196
DATED : October 20, 2020
INVENTOR(S) : Claire Ashman et al.

Page 1 of 1

It is certified that error appears in the above-identified patent and that said Letters Patent is hereby corrected as shown below:

On the Title Page

Column 1 (Title), Line 2, Below "PEPTIDES", insert (72) as follows:
-- Applicant: Glaxo Group Limited, Brentford (GB) --.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*